(12) United States Patent
Mazed

(10) Patent No.: US 11,723,449 B2
(45) Date of Patent: *Aug. 15, 2023

(54) ARTIFICIAL INTELLIGENCE (AI) AND AUGMENTED REALITY (AR) ENHANCED PERSONAL CARE DEVICES/APPARATUSES

(71) Applicant: Sayeeda Mazed, Yorba Linda, CA (US)

(72) Inventor: Sayeeda Mazed, Yorba Linda, CA (US)

( * ) Notice: Subject to any disclaimer, the term of this patent is extended or adjusted under 35 U.S.C. 154(b) by 497 days.

This patent is subject to a terminal disclaimer.

(21) Appl. No.: 16/873,522

(22) Filed: Apr. 25, 2020

(65) Prior Publication Data
US 2020/0305587 A1    Oct. 1, 2020

Related U.S. Application Data

(63) Continuation-in-part of application No. 15/330,358, filed on Sep. 12, 2016, now Pat. No. 10,646,027, (Continued)

(51) Int. Cl.
*A46B 9/02*    (2006.01)
*G06N 3/08*    (2023.01)
(Continued)

(52) U.S. Cl.
CPC .............. *A46B 9/023* (2013.01); *A61Q 5/002* (2013.01); *G06N 3/08* (2013.01); *G06T 19/006* (2013.01);
(Continued)

(58) Field of Classification Search
CPC .............. A46B 9/023; A46B 2200/102; A46B 2200/104; A46B 7/04; A46B 15/00;
(Continued)

(56) References Cited

U.S. PATENT DOCUMENTS

| | | | |
|---|---|---|---|
| 6,283,930 B1 * | 9/2001 | Purvis | A46B 5/0041 601/72 |
| 7,384,405 B2 * | 6/2008 | Rhoades | A61H 7/005 601/138 |

(Continued)

FOREIGN PATENT DOCUMENTS

| | | | |
|---|---|---|---|
| CN | 110935014 | * | 3/2020 |
| WO | WO2017082539 | * | 5/2017 |

*Primary Examiner* — Robert J Scruggs

(57) ABSTRACT

Personal care devices (or apparatuses) are described to deliver/activate a bioactive compound/botanical compound/biologically active molecule (including a regulatory protein/growth factor) or a mixture of bioactive compounds/botanical compounds/biologically active molecules (including regulatory proteins/growth factors) for growth and protection of hair or rejuvenation and protection of skin, which utilizes nanoencapsulation/nanoemulsion and/or activation/photoactivation. Such devices (or apparatuses) utilize a light low intensity module/x-ray and nanooptical elements/three-dimensionally (3-D) printed micro/nanostructures. Furthermore, the personal care devices (or apparatuses) can be enhanced with an artificial intelligence (AI) algorithm and/or augmented reality (AR) application (app).

27 Claims, 50 Drawing Sheets

Related U.S. Application Data which is a continuation-in-part of application No. 14/121,398, filed on Aug. 29, 2014, now Pat. No. 9,439,491.

(60) Provisional application No. 61/959,634, filed on Aug. 29, 2013.

(51) Int. Cl.
 *A61Q 5/00* (2006.01)
 *G06T 19/00* (2011.01)
 *G09B 3/06* (2006.01)
 *A61H 7/00* (2006.01)

(52) U.S. Cl.
 CPC .......... *G09B 3/06* (2013.01); *A46B 2200/102* (2013.01); *A46B 2200/104* (2013.01); *A61H 7/003* (2013.01); *A61H 2205/021* (2013.01)

(58) Field of Classification Search
 CPC ............ A46B 15/0002; A46B 15/0004; A46B 15/0022; A46B 15/003; A46B 15/0034; A46B 15/0036; A46B 15/0077; A61Q 5/002; A61Q 5/00; G06N 3/08; G06N 5/02; G06T 19/006; G06T 19/00; G06T 16/953; G09B 3/06; A61H 7/003; A61H 2205/021; H04L 12/58; A61K 8/347; A61K 8/35; A61K 8/60; A01K 13/002; A61N 5/0616; A61N 5/0617; A61N 2005/0626; A45D 19/02; A45D 19/16

See application file for complete search history.

(56) References Cited

U.S. PATENT DOCUMENTS

| | | | | |
|---|---|---|---|---|
| 9,823,737 | B2 * | 11/2017 | Mazed | G06V 40/168 |
| 11,000,118 | B2 * | 5/2021 | Rivera | A46B 17/08 |
| 11,259,627 | B2 * | 3/2022 | Boersma | A46B 13/008 |
| 2008/0027328 | A1 * | 1/2008 | Klopotek | A61B 8/4281 |
| | | | | 600/472 |
| 2008/0230246 | A1 * | 9/2008 | Dollar-Wright | A45D 24/007 |
| | | | | 173/29 |
| 2009/0083917 | A1 * | 4/2009 | Taggart | A46B 13/023 |
| | | | | 15/186 |
| 2010/0106077 | A1 * | 4/2010 | Rabin | A61N 5/0617 |
| | | | | 604/20 |
| 2012/0174937 | A1 * | 7/2012 | Ragosta | A46B 13/005 |
| | | | | 132/223 |
| 2015/0135455 | A1 * | 5/2015 | Reusche | A46B 9/023 |
| | | | | 15/160 |
| 2021/0273892 | A1 * | 9/2021 | Rakshit | G06F 16/953 |

\* cited by examiner

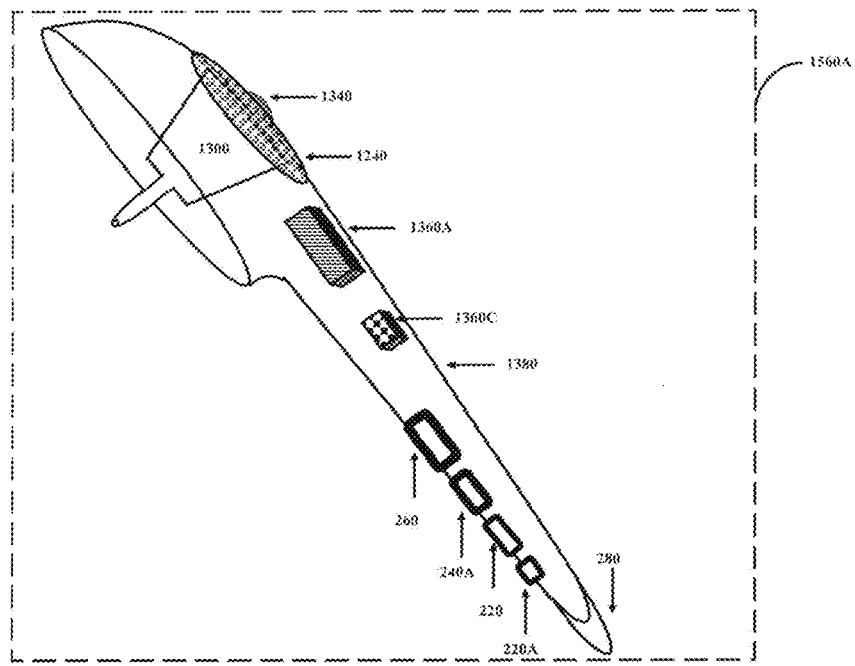
FIG. 10A
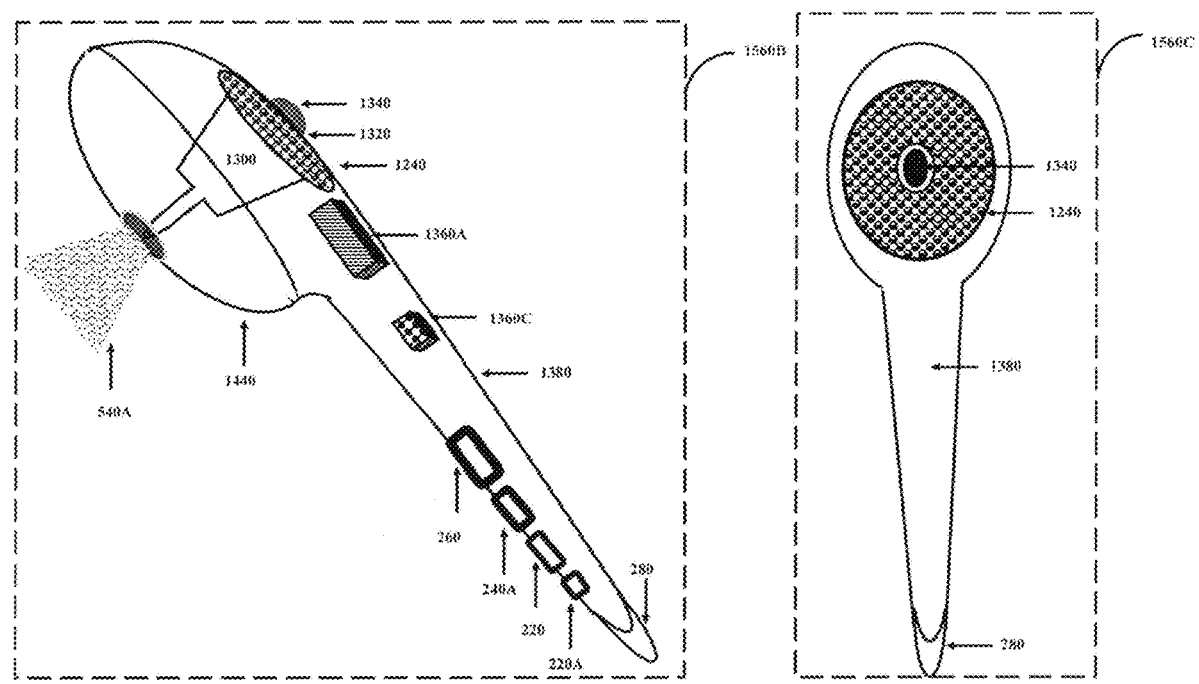
FIG. 10B
FIG. 10C

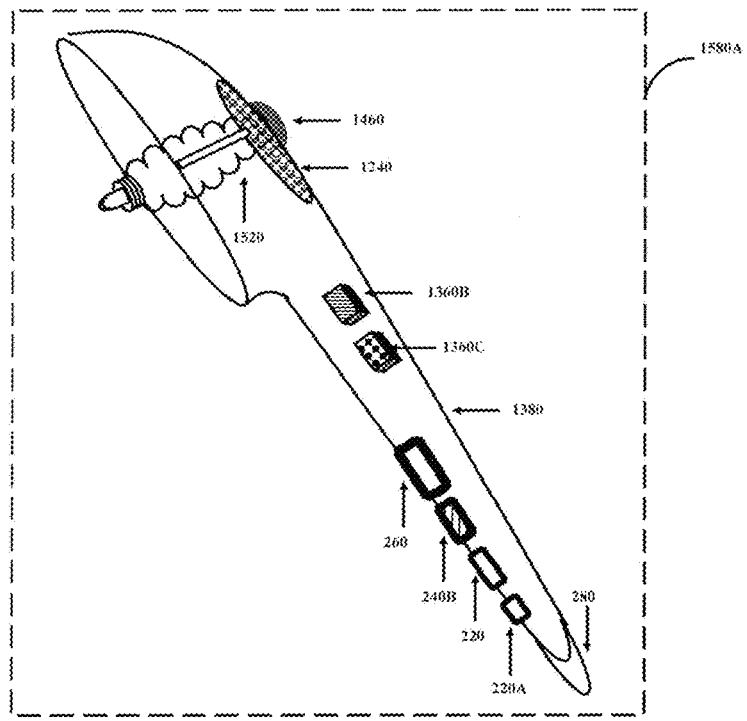
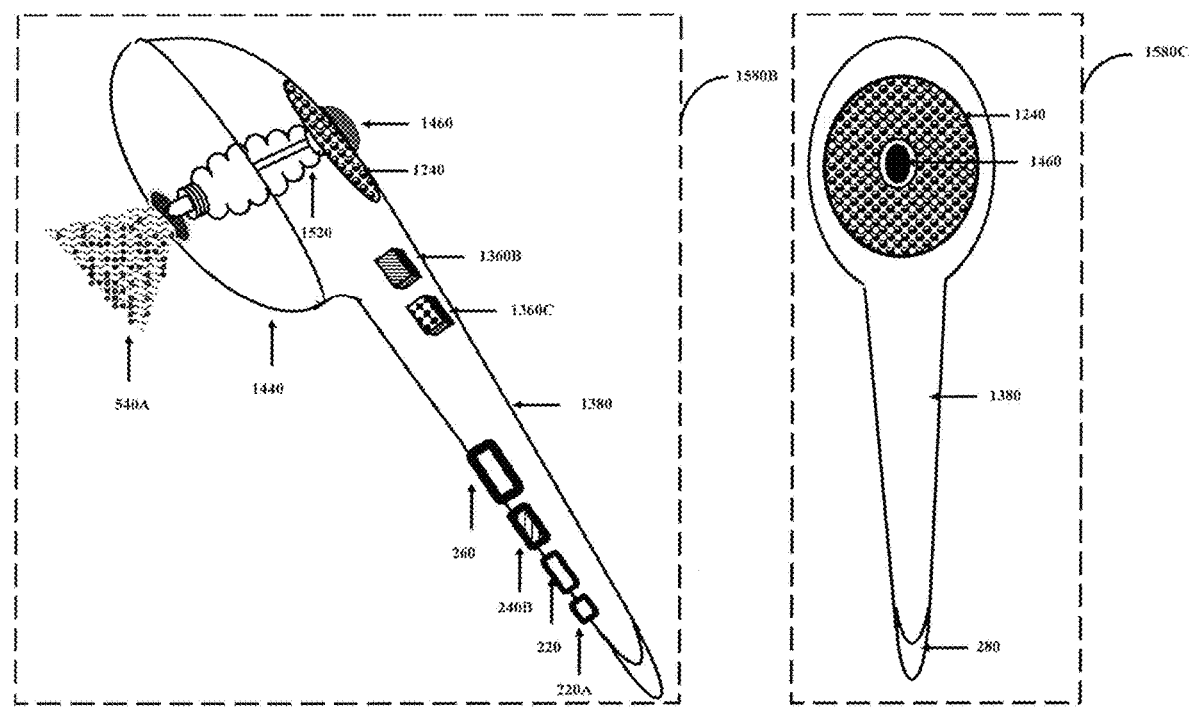

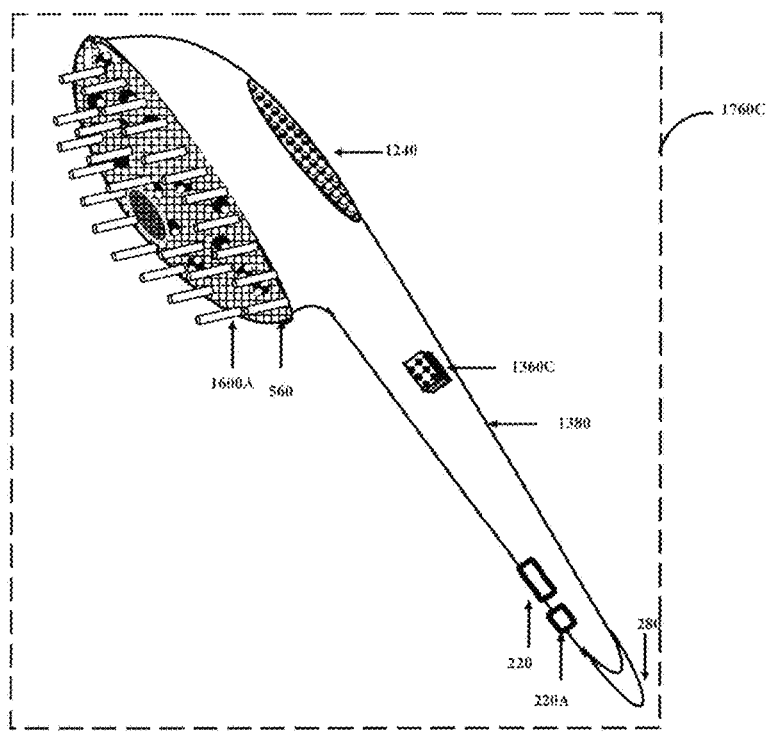
FIG. 17C
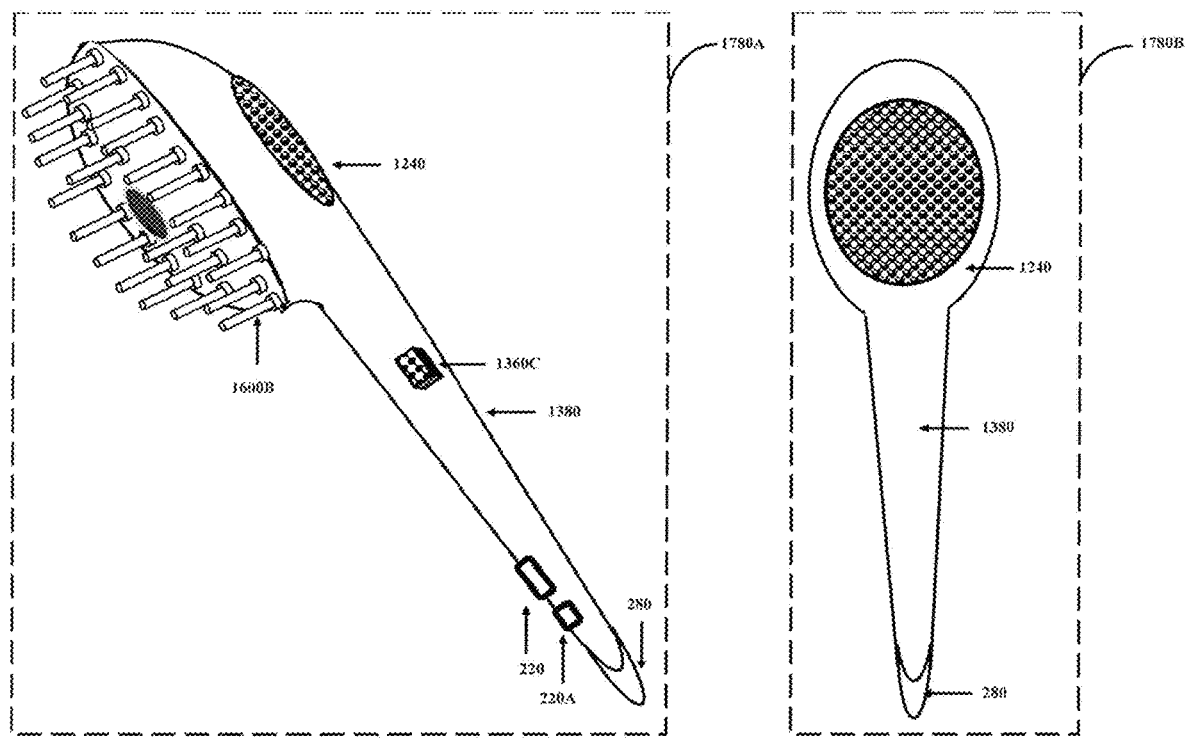
FIG. 18A
FIG. 18B

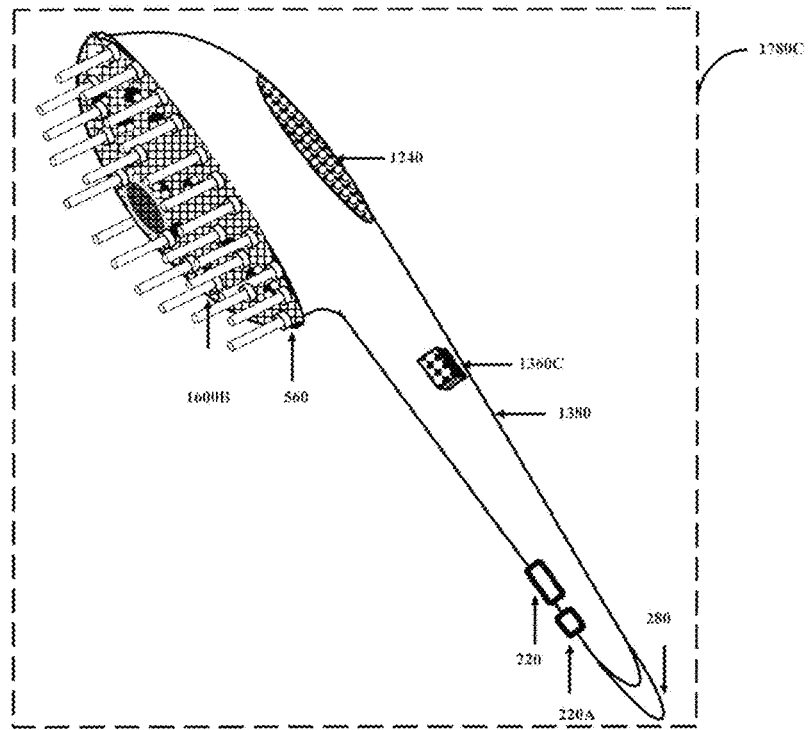
FIG. 18C
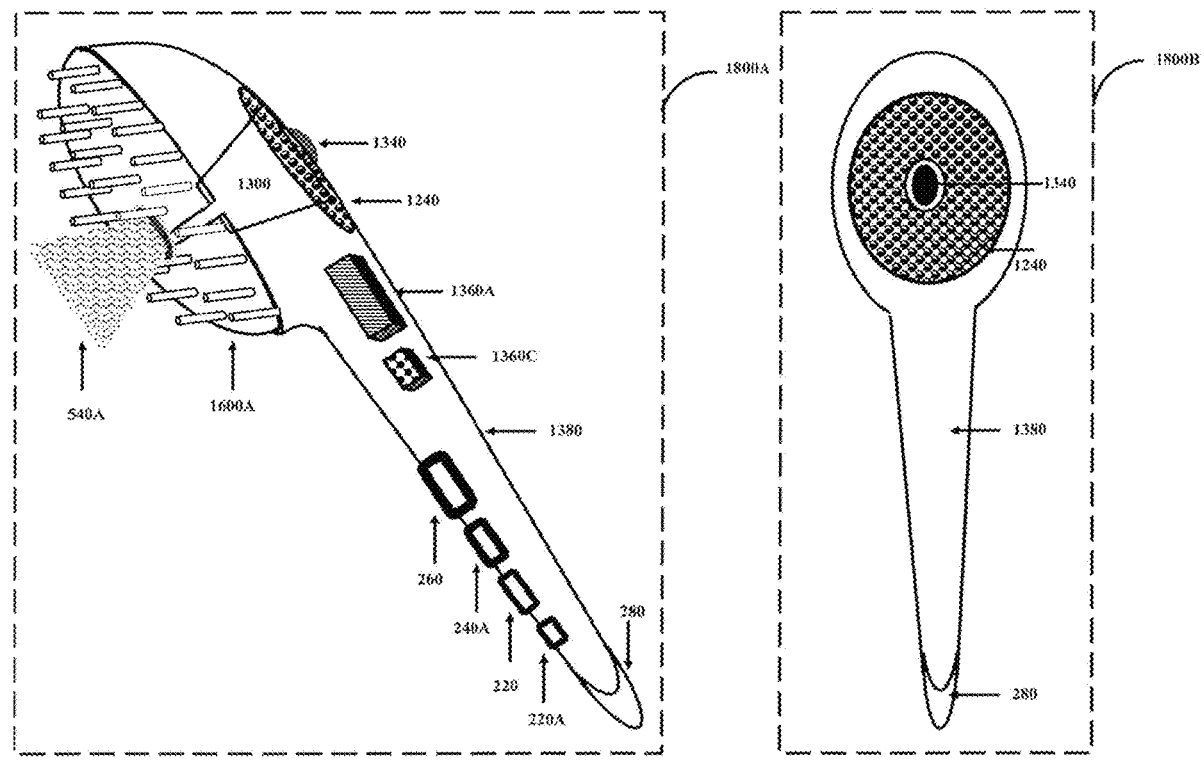
FIG. 19A
FIG. 19B

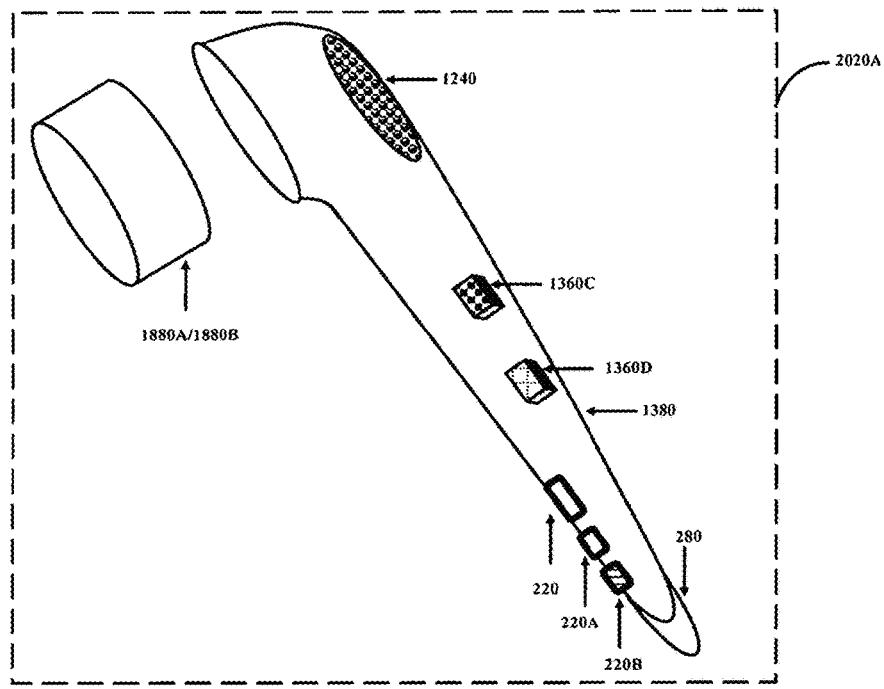
FIG. 27A
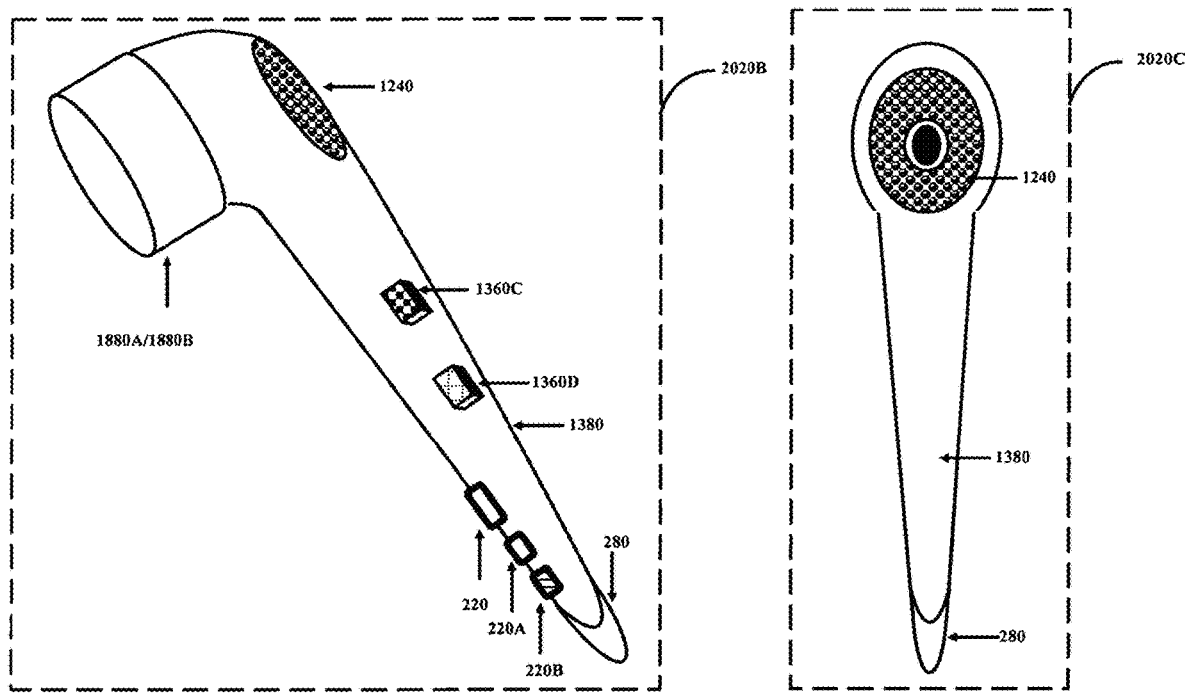
FIG. 27B
FIG. 27C

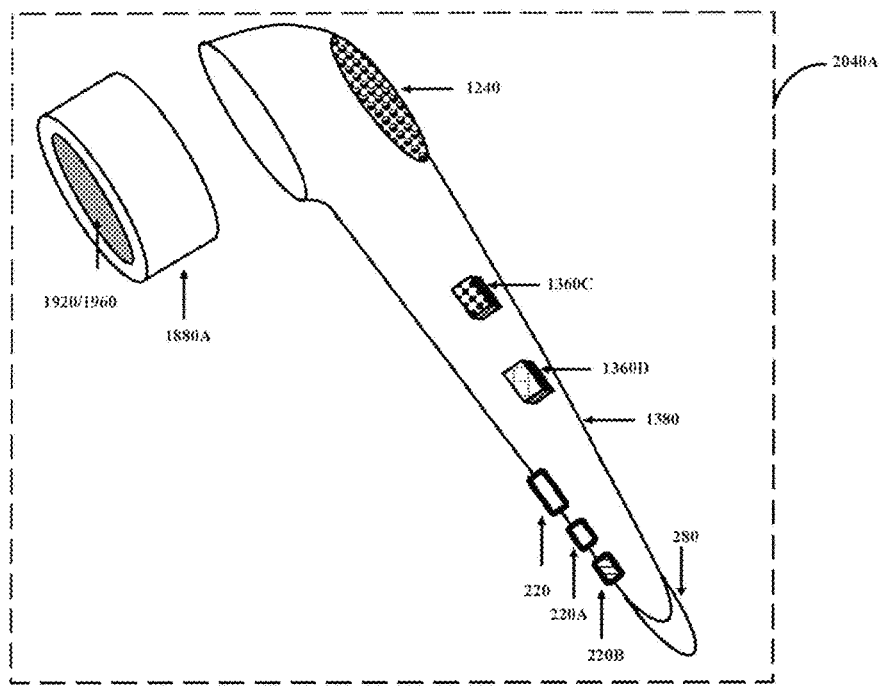
FIG. 28A
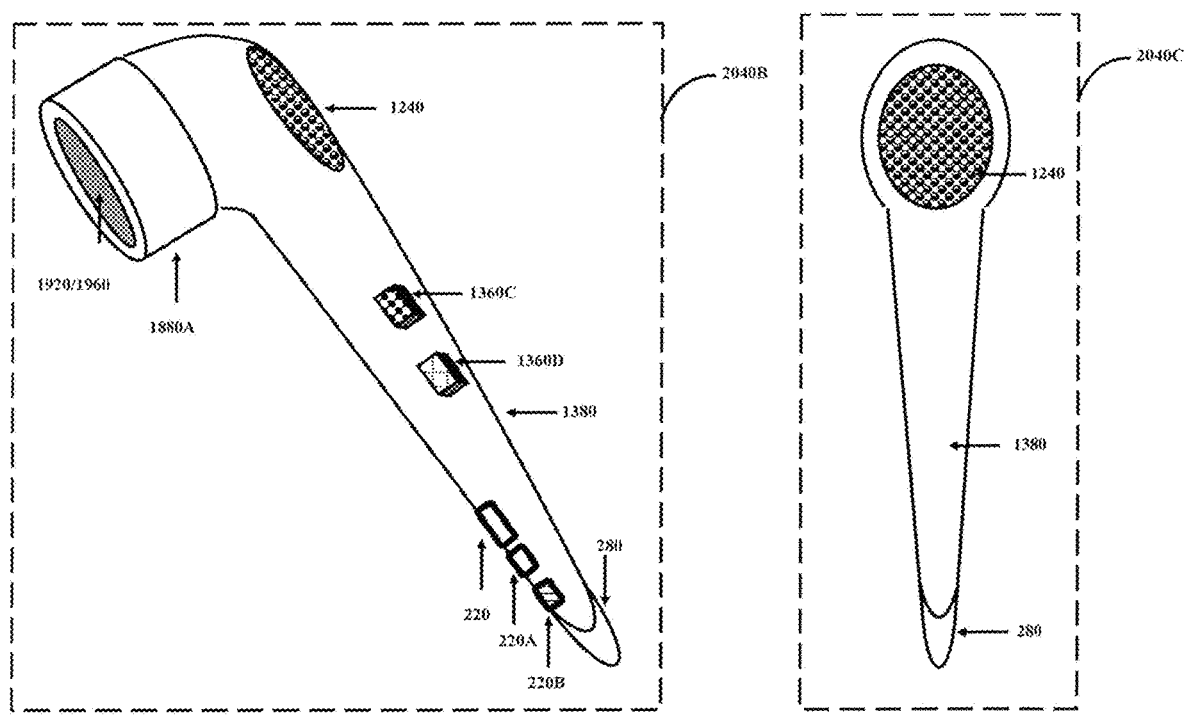
FIG. 28B
FIG. 28C

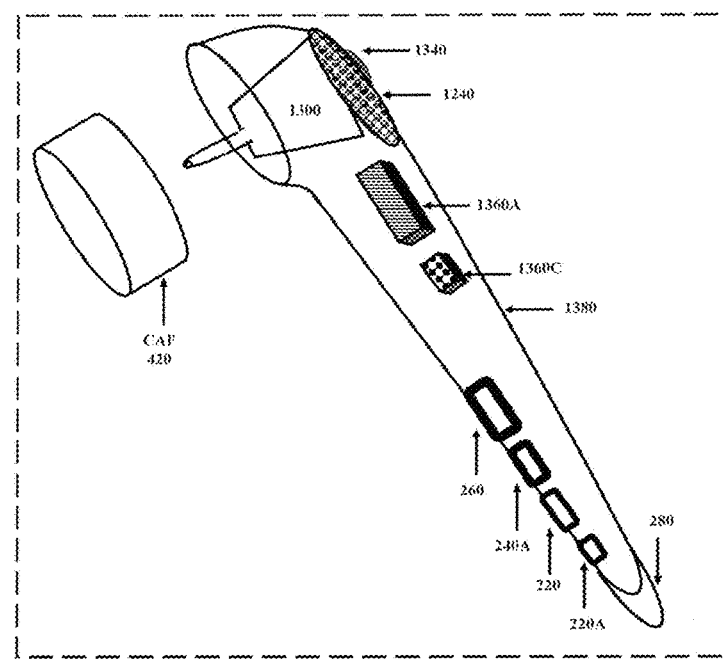 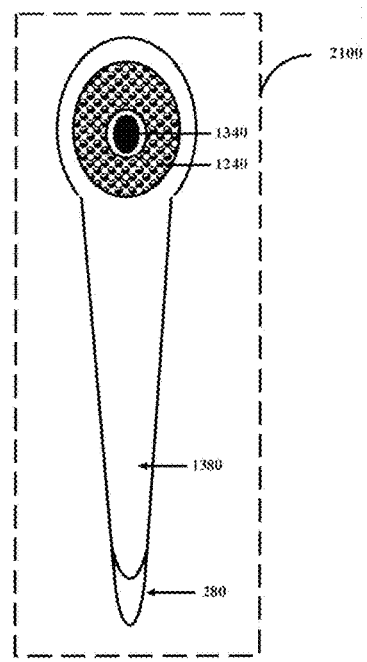
FIG. 31A  FIG. 31B
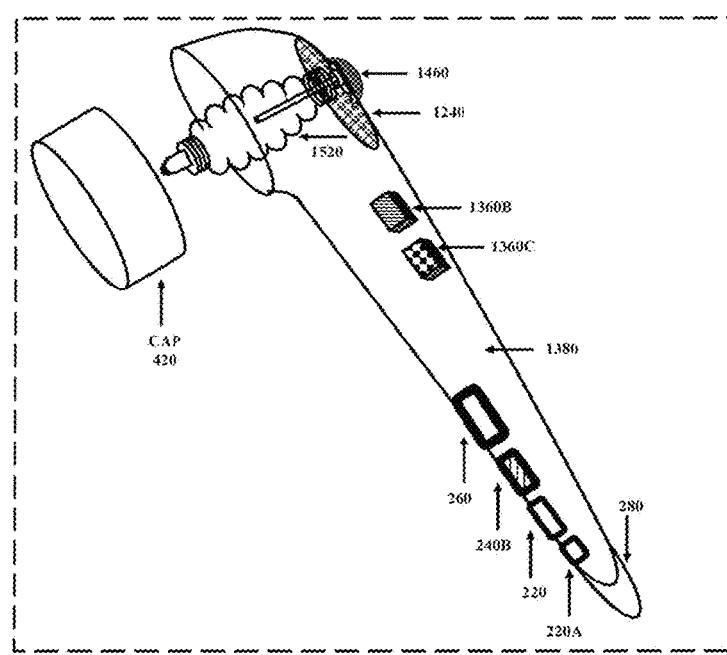 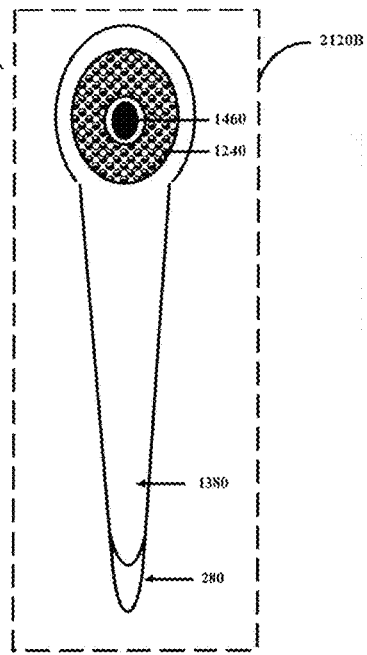
FIG. 32A  FIG. 32B

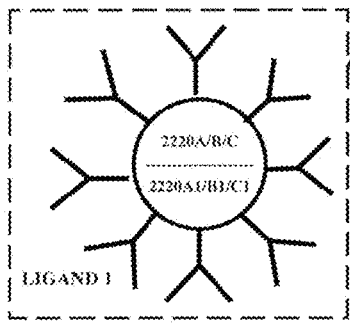
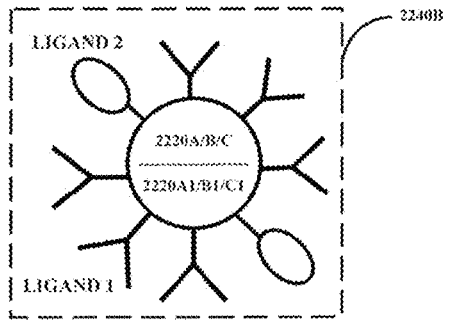
FIG. 38A      FIG. 38B
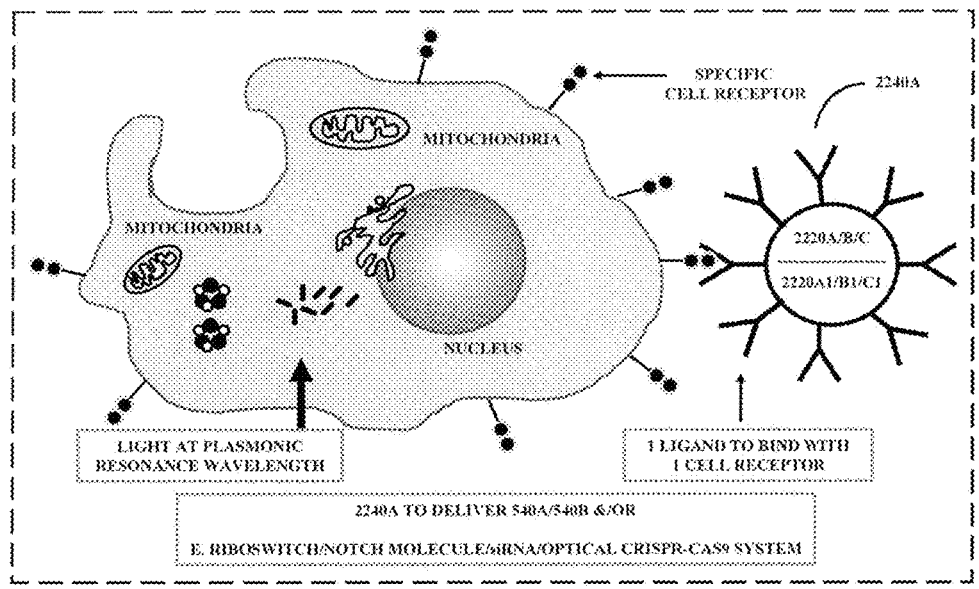
FIG. 39A
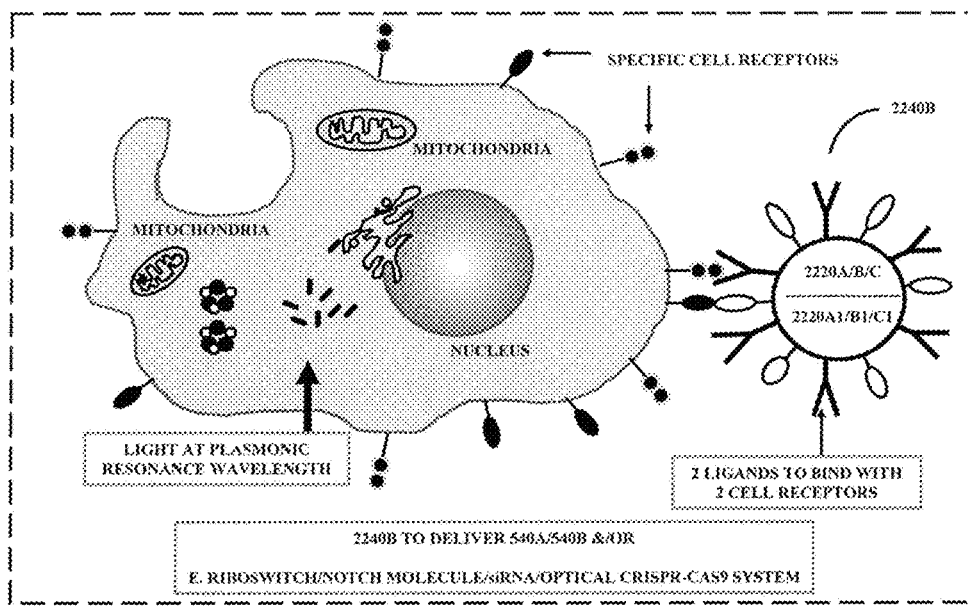
FIG. 39B

ID="11,723,449 B2" -->

ARTIFICIAL INTELLIGENCE (AI) AND AUGMENTED REALITY (AR) ENHANCED PERSONAL CARE DEVICES/APPARATUSES

CROSS REFERENCE OF RELATED APPLICATION

The present application is a
continuation-in-part (CIP) patent application of (a) a U.S. Non-Provisional patent application Ser. No. 15/330,358, entitled "MULTIFUNCTIONAL HAIRBRUSH FOR DELIVERING A BIOACTIVE COMPOUND FOR GROWTH AND PROTECTION OF. HAIR", filed on Sep. 12, 2016,
wherein (a) is a continuation-in-part (CIP) patent application of a (b) U.S. Non-Provisional patent application Ser. No. 14/121,398, entitled "MULTIFUNCTIONAL HAIRBRUSH FOR DELIVERING A BIOACTIVE COMPOUND FOR GROWTH AND PROTECTION OF HAIR", filed on Aug. 29, 2014,
wherein (b) claims benefit of priority to (c) U.S. Provisional Patent Application, Ser. No. 61/959,634, entitled "MULTIFUNCTIONAL HAIRBRUSH", filed on Aug. 29, 2013.

The entire contents of all (i) U.S. Non-Provisional Patent Applications, (ii) U.S. Provisional Patent Applications, as listed in the previous paragraph and (iii) the filed (Patent) Application Data Sheet (ADS) are hereby incorporated by reference, as if they are reproduced herein in their entirety.

BACKGROUND OF THE INVENTION

The present invention relates to multifunctional personal care devices (or apparatuses) generally comprising/including mechanical, electrical (electronic) and optical (including nanooptical elements) subsystems/microsubsystems/units/moduleskomponents.

Personal care devices (or apparatuses) to deliver/activate a bioactive compound/botanical compound/biologically active molecule (including a regulatory protein/growth factor) or a mixture of bioactive compounds/botanical compounds/biologically active molecules (including regulatory proteins/growth factors) for growth and protection of hair or rejuvenation and protection of skin. Such personal care devices (or apparatuses) can utilize three-dimensionally (3-D) printed micro/nanostructures and such compositions (formulations) can utilize nanoencapsulation/nanoemulsion and/or activation/photoactivation.

BRIEF DESCRIPTION OF THE TABLES

For Growth and Protection of Hair

Table 1, Table 2, Table 3 and Table 4 describe various compositions of a removable/stretchable mesh structured net.

For Rejuvenation and Protection of Skin

Table 5, Table 6, Table 7 and Table 8 describe various topical compositions (formulations). Table 9 describes a non-topical composition (formulation).

BRIEF DESCRIPTION OF THE DRAWINGS

For Growth and Protection of Hair

FIG. 10A illustrates a mechanical assembly with the detachable spray applicator (based on the ultrasonic wave generator/vibrator) and the detachable low intensity light module.

FIGS. 10B-10C illustrate a front view and back view respectively of an embodiment of a complete mechanical assembly of the detachable spray applicator (based on the ultrasonic wave generator/vibrator), the detachable low intensity light module and the detachable cap assembly.

FIG. 11A illustrates a mechanical assembly with the detachable spray applicator (based on the nozzle) and the detachable low intensity light module. FIGS. 11B-11C illustrate a front view and back view respectively of an embodiment of a complete mechanical assembly of the detachable spray applicator (based on the nozzle), the detachable low intensity light module and the detachable cap assembly.

FIG. 17C illustrates a front view of a mechanical assembly with the detachable low intensity light module and the detachable hairbrush unit with the removable/stretchable integrated mesh structured net.

FIGS. 18A-18C are similar to FIGS. 17A-17C, wherein the particular detachable hairbrush unit (in FIGS. 17A-17C) is replaced by another detachable hairbrush unit.

FIG. 19A illustrates an embodiment of a front view of a complete mechanical assembly with the detachable low intensity light module, the detachable spray applicator (based on the ultrasonic wave generator/vibrator) and the detachable hairbrush unit. FIG. 19B illustrates a back view of the complete mechanical assembly (as illustrated in FIG. 19A).

For Rejuvenation and Protection of Skin

Figure 23A:
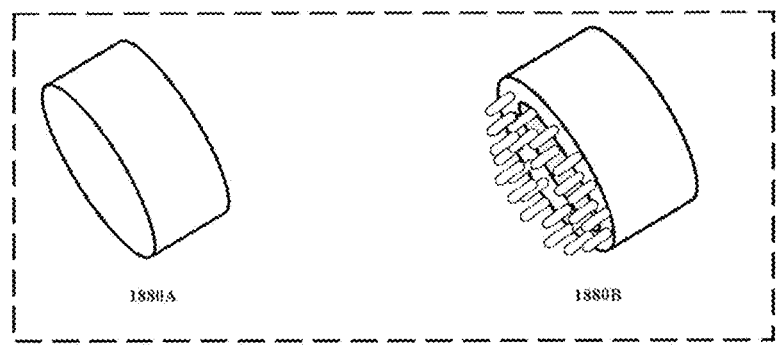
Figure 23B:
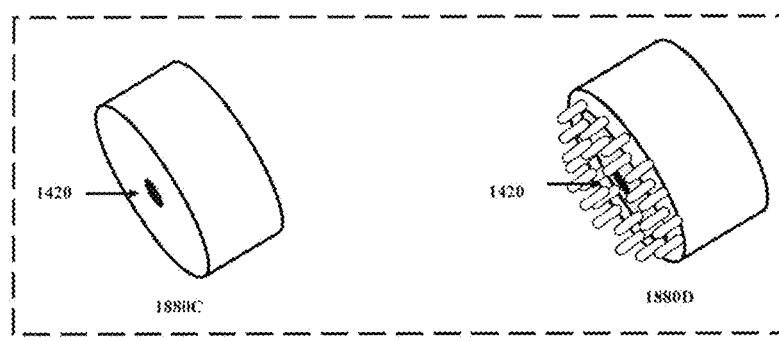

FIG. 23A illustrates two embodiments of a detachable skin brush unit for motion/vibration (including clockwise motion/counter clockwise motion/circular motion). FIG. 23B illustrates above two skin detachable brush units, wherein each detachable skin brush unit has a hole close to center of the frame of each detachable skin brush unit.

Figure 24A:
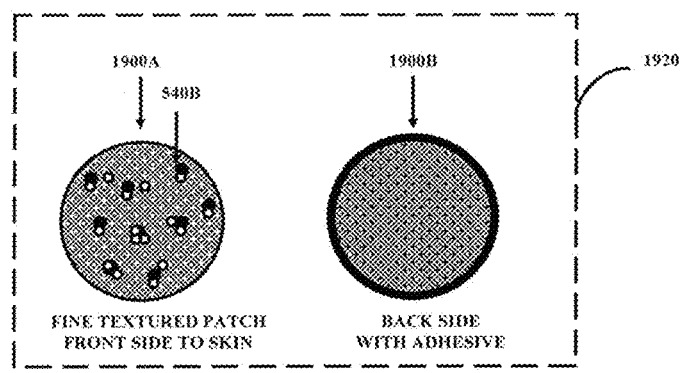
Figure 24B:
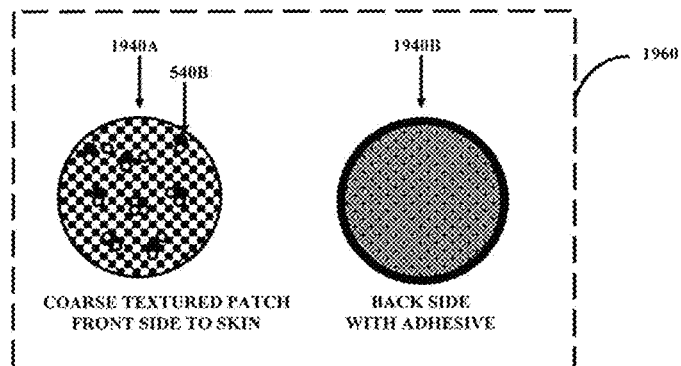

FIG. 24A illustrates a front surface and a back surface of a removable fine textured patch. FIG. 24B illustrates a front surface and a back surface of a removable coarse textured patch.

Figure 25A:
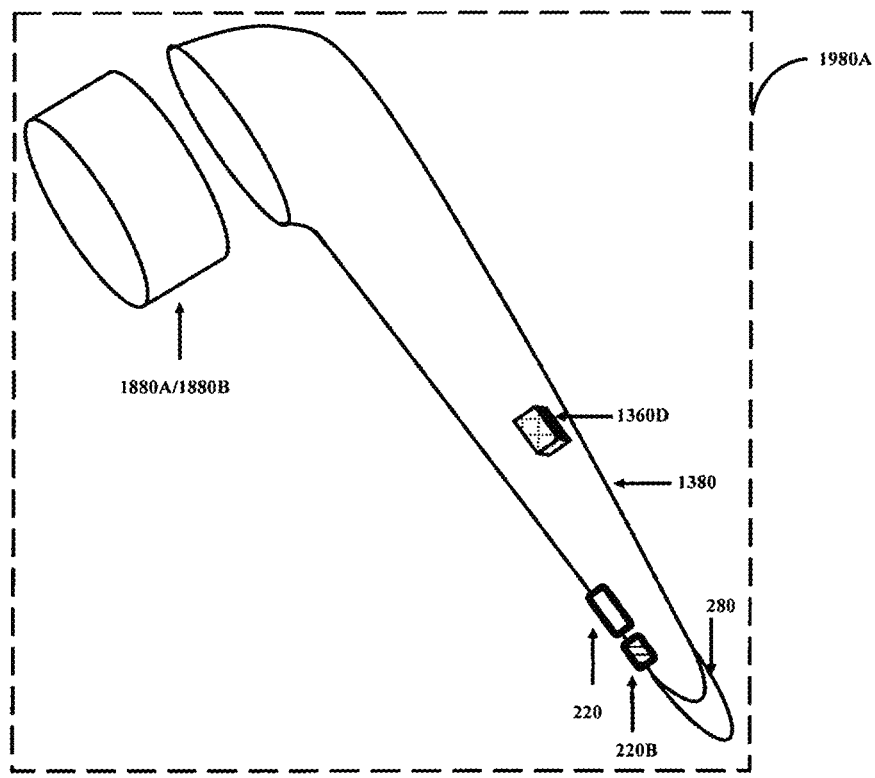
Figure 25B:
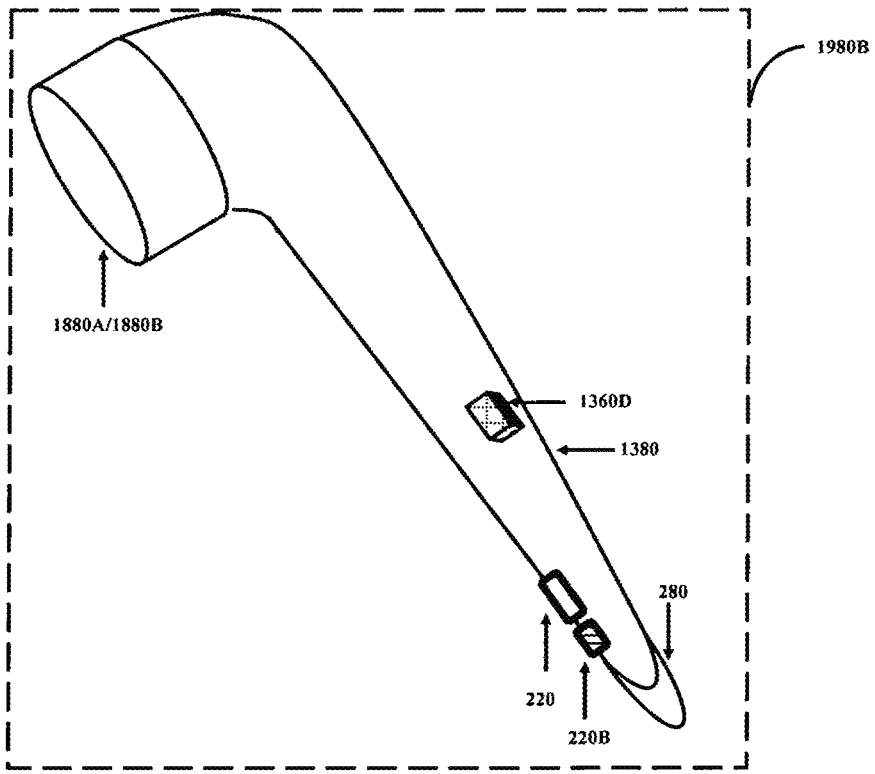

FIG. 25A illustrates a mechanical assembly with two types of detachable skin brush units for motion/vibration (including clockwise motion/counter clockwise motion/circular motion). FIG. 25B illustrates an embodiment of a complete mechanical assembly with two types of the detachable skin brush units for motion/vibration (including clockwise motion/counter clockwise motion/circular motion).

Figure 26A:
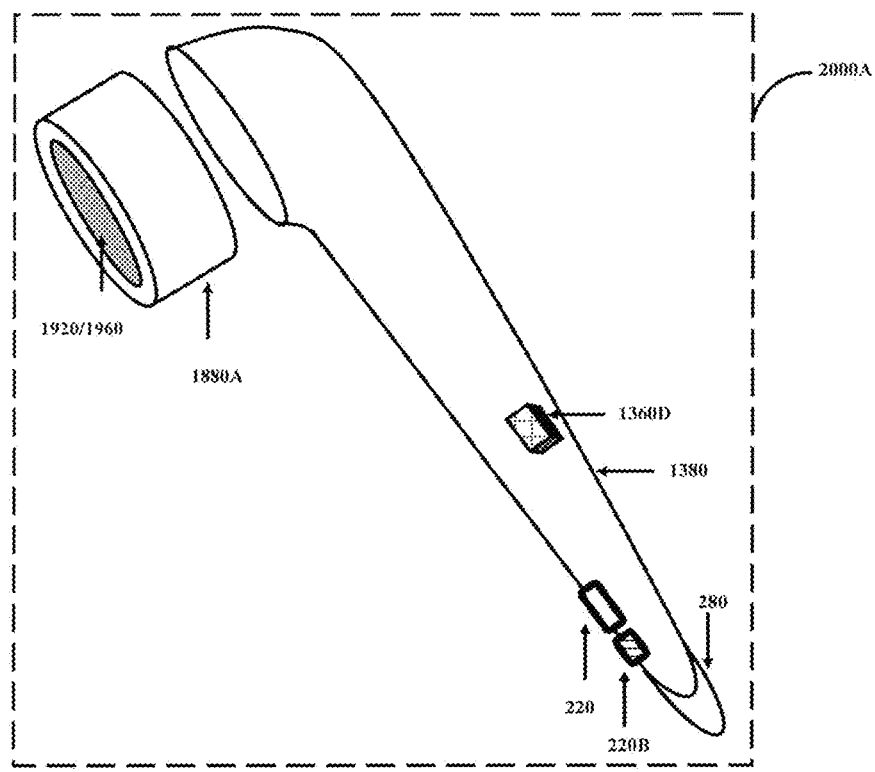
Figure 26B:
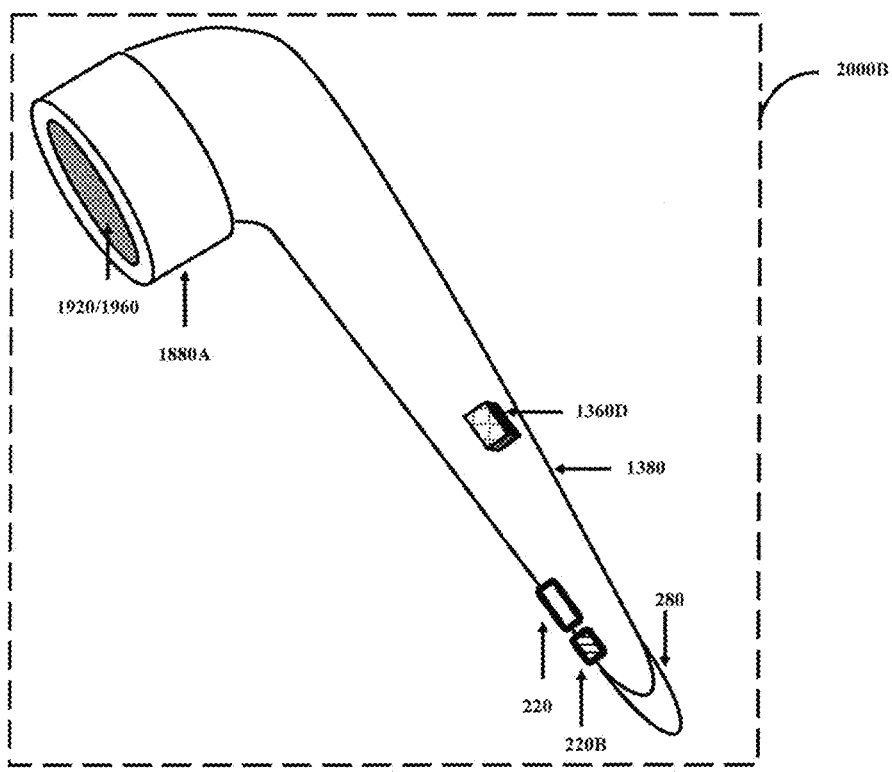

FIG. 26A illustrates a mechanical assembly of the particular detachable skin brush unit for motion/vibration (including clockwise motion/counter clockwise motion/circular motion) and the removable fine/coarse textured patch. FIG. 26B illustrates an embodiment of a complete mechanical assembly of the particular detachable skin brush unit for motion/vibration (including clockwise motion/counter clockwise motion/circular motion) with the removable fine/coarse textured patch.

FIG. 27A illustrates a mechanical assembly with the detachable low intensity light module and two types of detachable skin brush units for motion/vibration (including clockwise motion/counter clockwise motion/circular motion). FIG. 27B illustrates a front view of an embodiment of a complete mechanical assembly with the detachable low intensity light module and two types of detachable skin brush units for motion/vibration (including clockwise motion/counter clockwise motion/circular motion). FIG. 27C illustrates a back view of the complete mechanical assembly (as illustrated in FIG. 27B).

FIG. 28A illustrates a mechanical assembly with the detachable low intensity light module, the particular detachable skin brush unit for motion/vibration (including clockwise motion/counter clockwise motion/circular motion) and the removable fine/coarse textured patch. FIG. 28B illustrates a front view of an embodiment of a complete mechanical assembly with the detachable low intensity light module, the particular detachable skin brush unit for motion/vibration (including clockwise motion/counter clockwise motion/circular motion) and the removable fine/coarse textured patch. FIG. 28C illustrates a back view of the complete mechanical assembly (as illustrated in FIG. 28B).

Figure 29A:
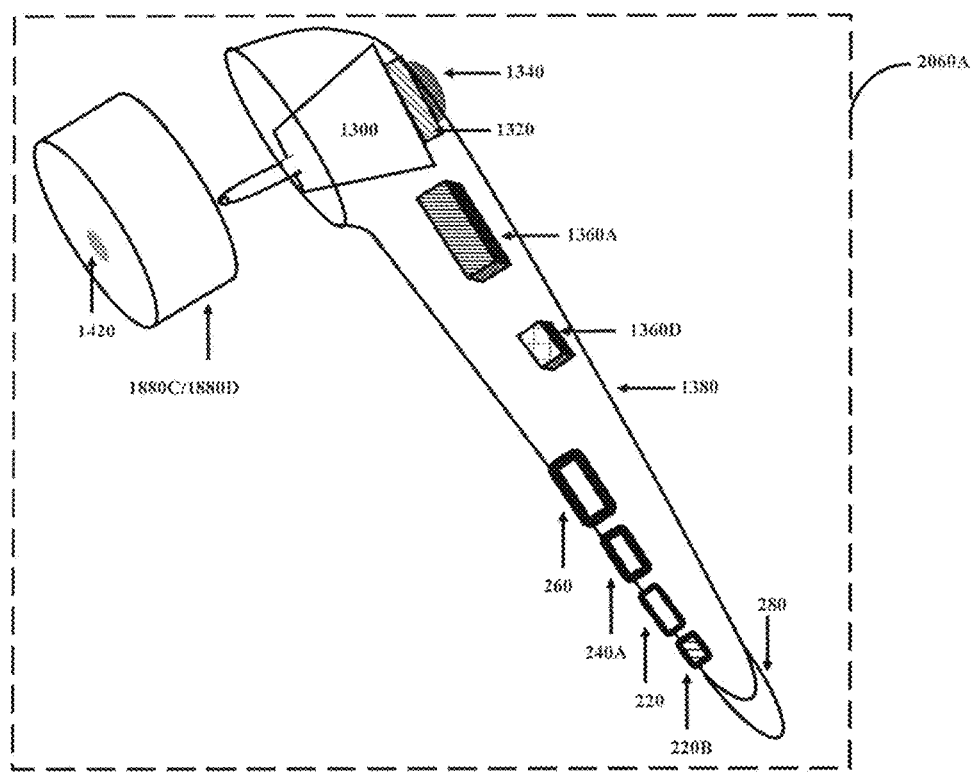
Figure 29B:
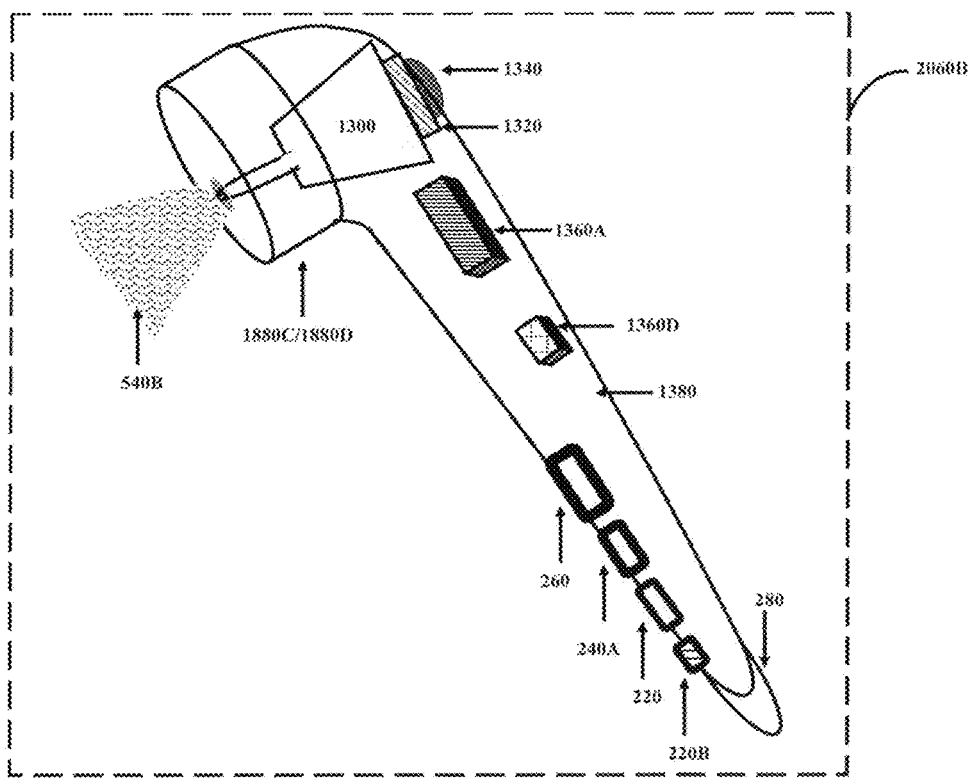
Figure 29C:
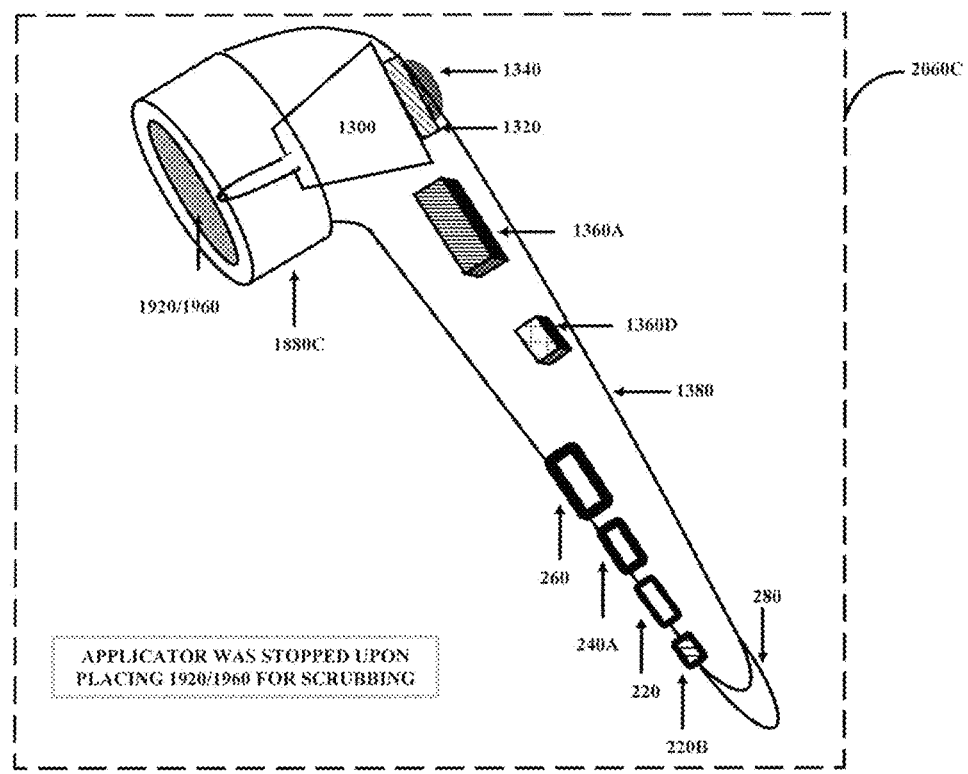

FIG. 29A illustrates a mechanical assembly of the detachable spray applicator (based on the ultrasonic wave generator/vibrator) with two types of the detachable skin brush units for motion/vibration (including clockwise motion/counter clockwise motion/circular motion). FIG. 29B illustrates a complete mechanical assembly of the detachable spray applicator (based on the ultrasonic wave generator/vibrator) and two types of the detachable skin brush units for motion/vibration (including clockwise motion/counter clockwise motion/circular motion). FIG. 29C illustrates a complete mechanical assembly of the detachable spray applicator (based on the ultrasonic wave generator/vibrator), the particular detachable skin brush unit for motion/vibration (including clockwise motion/counter clockwise motion/circular motion) and the removable fine/coarse textured patch.

Figure 30A:
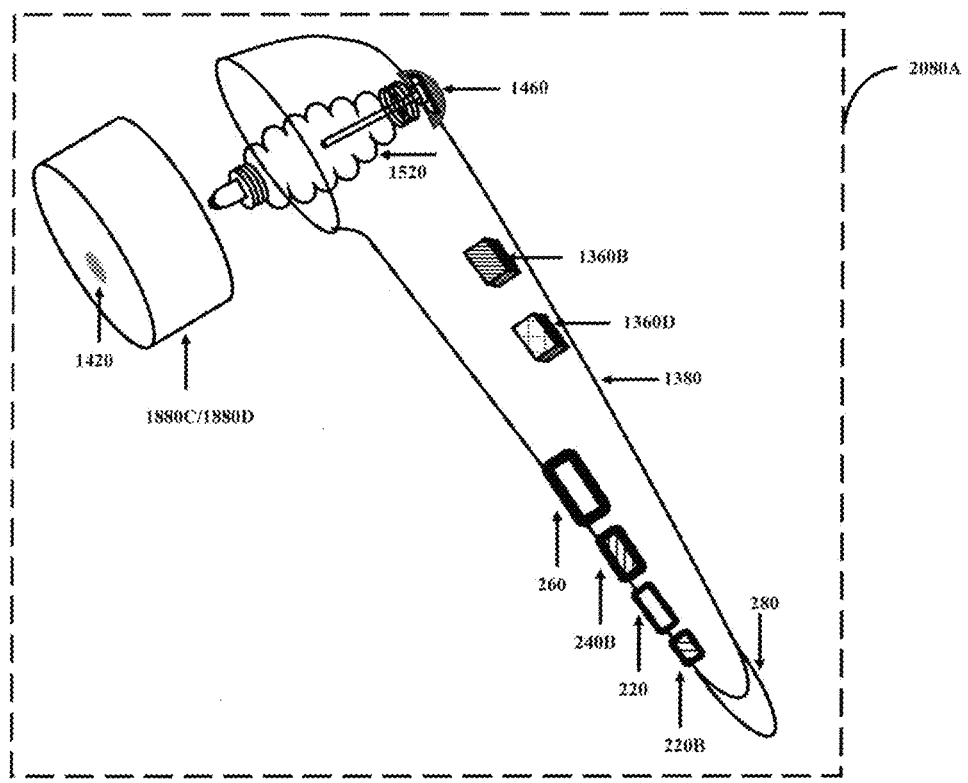
Figure 30B:
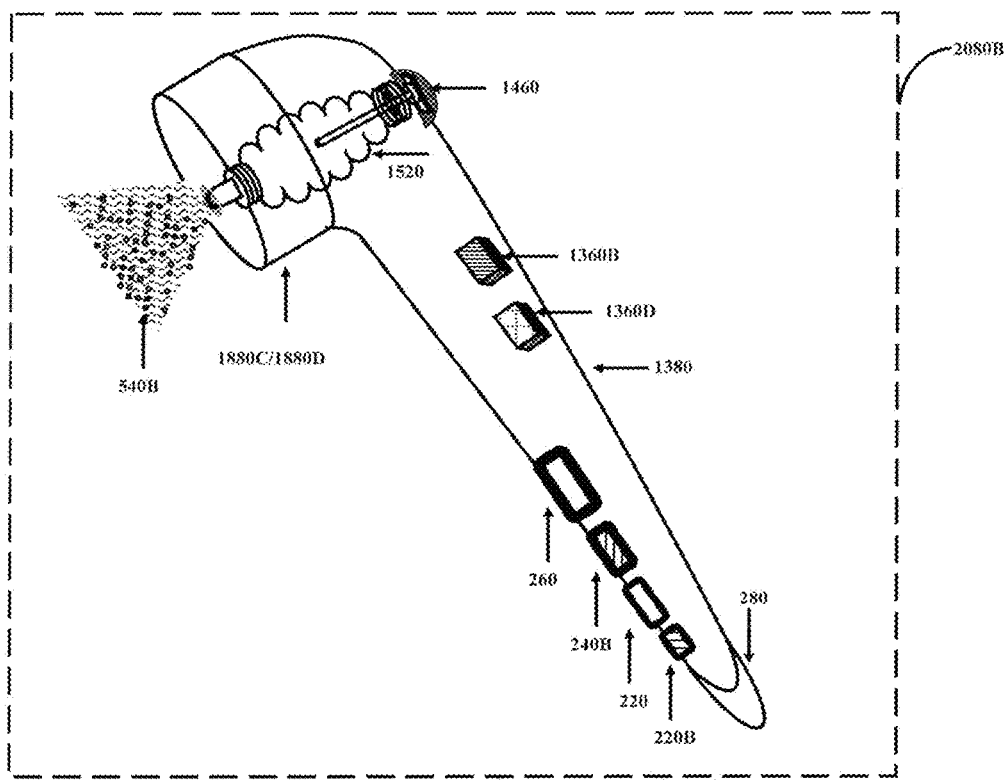
Figure 30C:
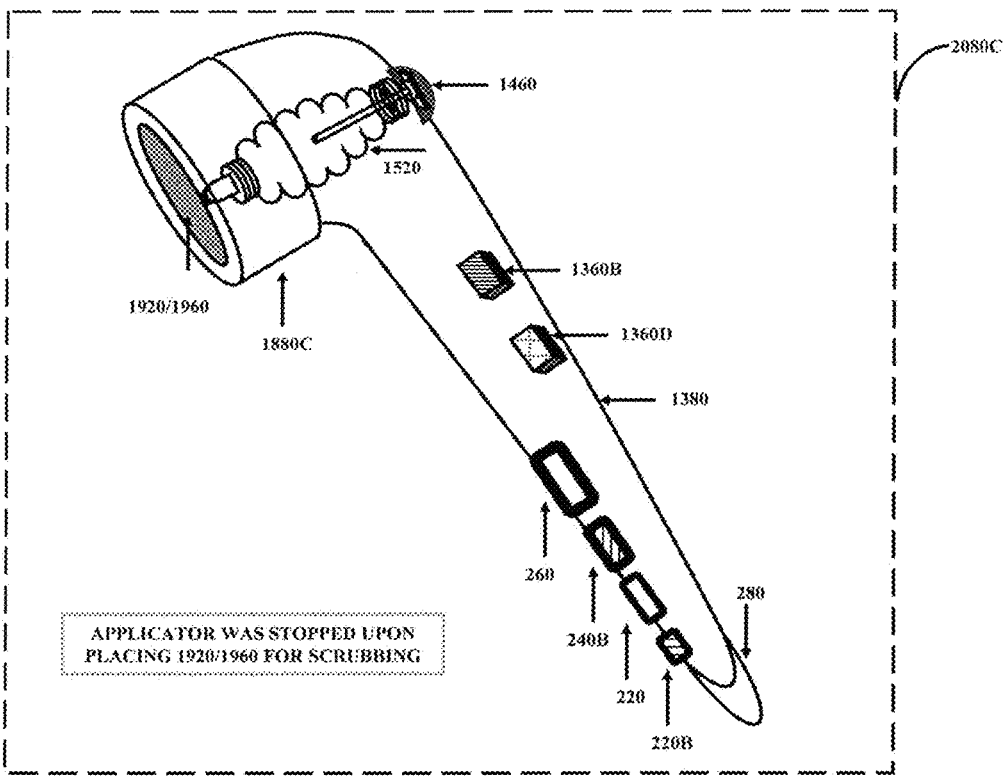

FIGS. 30A-30C are similar to FIGS. 29A-29C respectively, except the detachable spray applicator (based on the ultrasonic wave generator/vibrator) is replaced by the detachable spray applicator (based on the nozzle).

FIG. 31A illustrates a front view of a mechanical assembly with the detachable cap, the detachable low intensity light module and the detachable spray applicator (based on the ultrasonic wave generator/vibrator). FIG. 31B illustrates a back view of the mechanical assembly (as illustrated in FIG. 31A).

FIGS. 32A-32B are similar to FIGS. 31A-3113 respectively, except the detachable spray applicator (based on the ultrasonic wave generator/vibrator) is replaced by the detachable spray applicator (based on the nozzle).

Figure 33A:
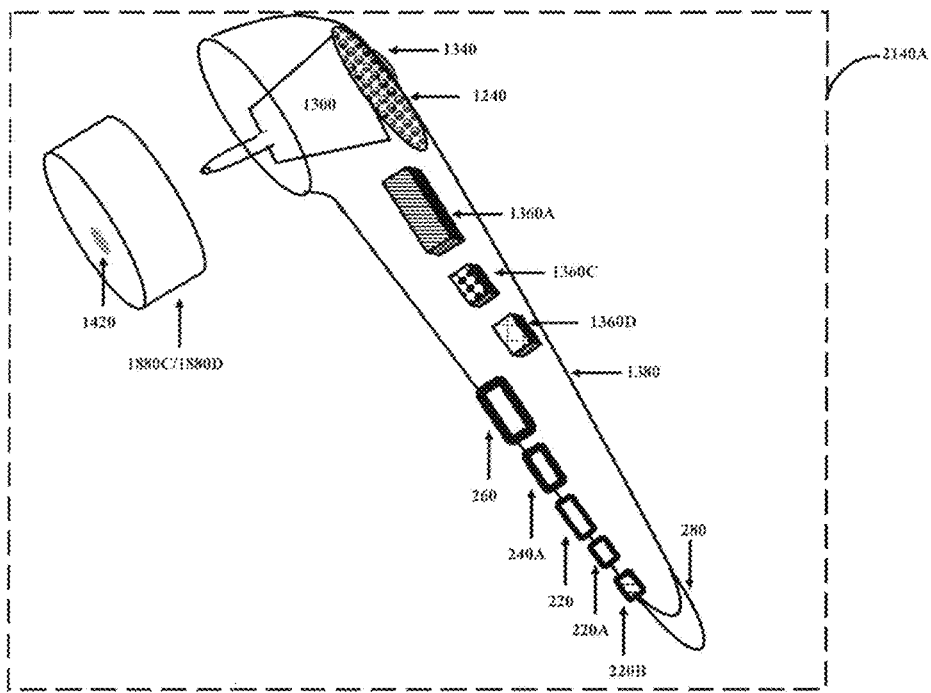
Figure 33B:
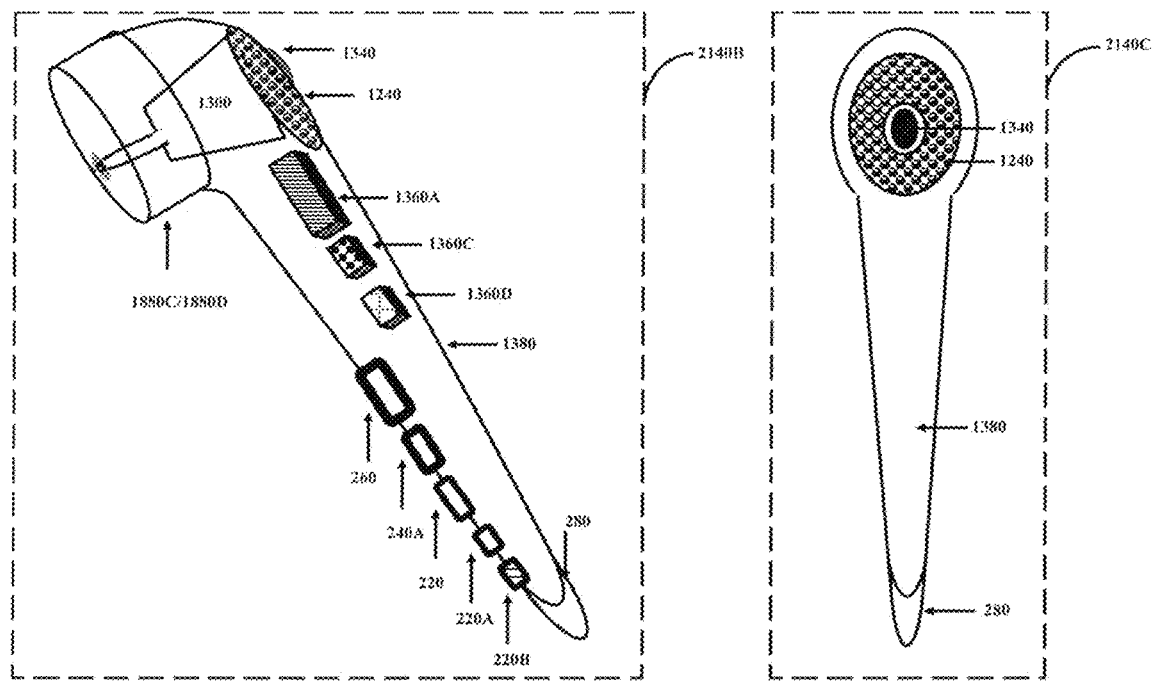
Figure 33C:
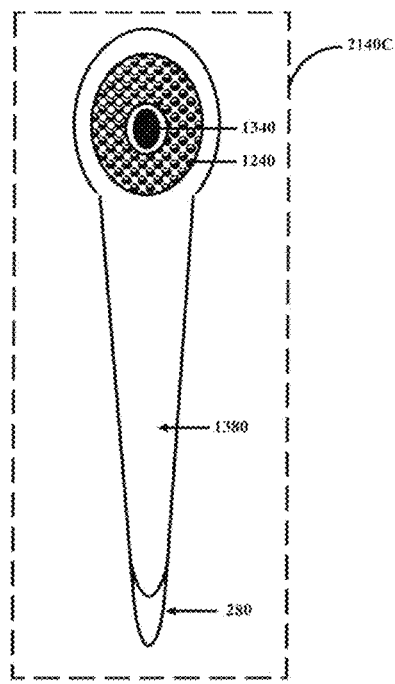

FIG. 33A illustrates a mechanical assembly with the detachable low intensity light module, the detachable spray applicator (based on the ultrasonic wave generator/vibrator) and the two types of detachable skin brush units. FIG. 33B illustrates a front view of the complete mechanical assembly with the detachable low intensity light module, the detachable spray applicator (based on the ultrasonic wave generator/vibrator) and the two types of detachable skin brush units. FIG. 33C illustrates a back view of the complete mechanical assembly (as illustrated in FIG. 33B).

Figure 34A:
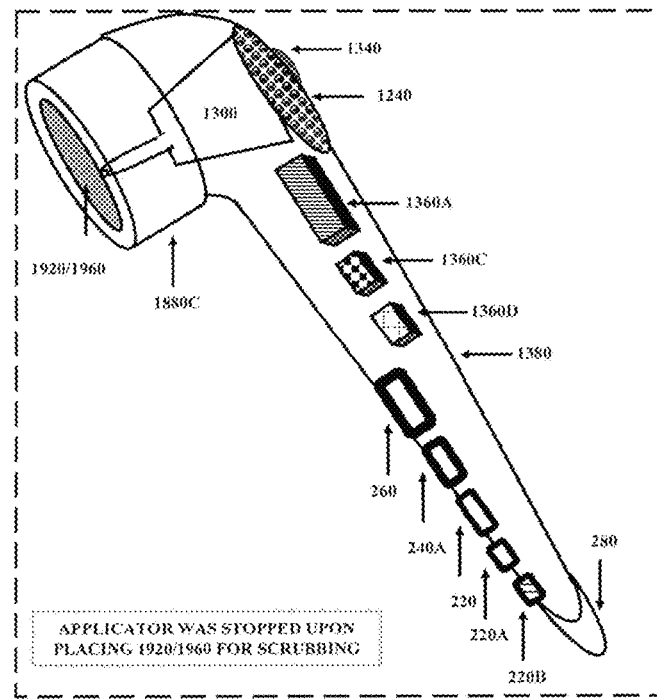
Figure 34B:
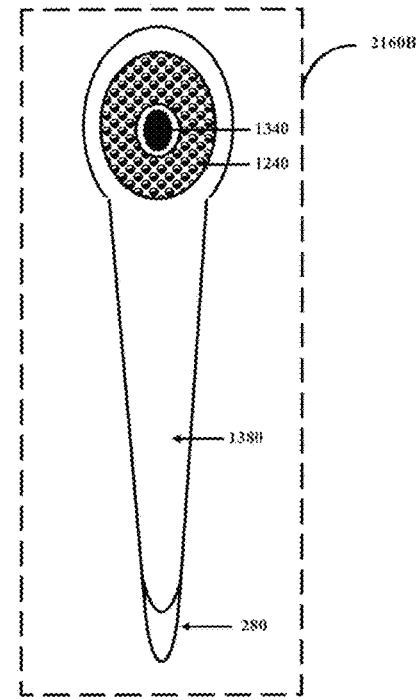

FIG. 34A illustrates a front view of a complete mechanical assembly with the detachable low intensity light module, the detachable spray applicator (based on the ultrasonic wave generator/vibrator), the particular detachable skin brush unit and the removable fine/coarse textured patch. FIG. 34B illustrates a back view of the complete mechanical assembly (as illustrated in FIG. 34A)

Figure 35A:
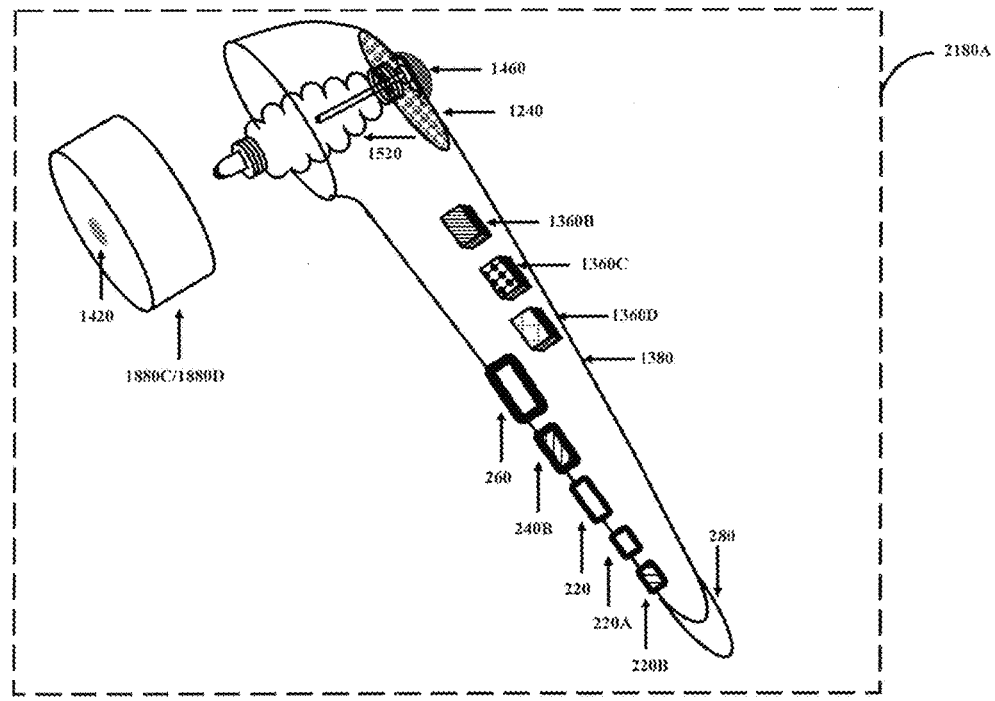
Figure 35B:
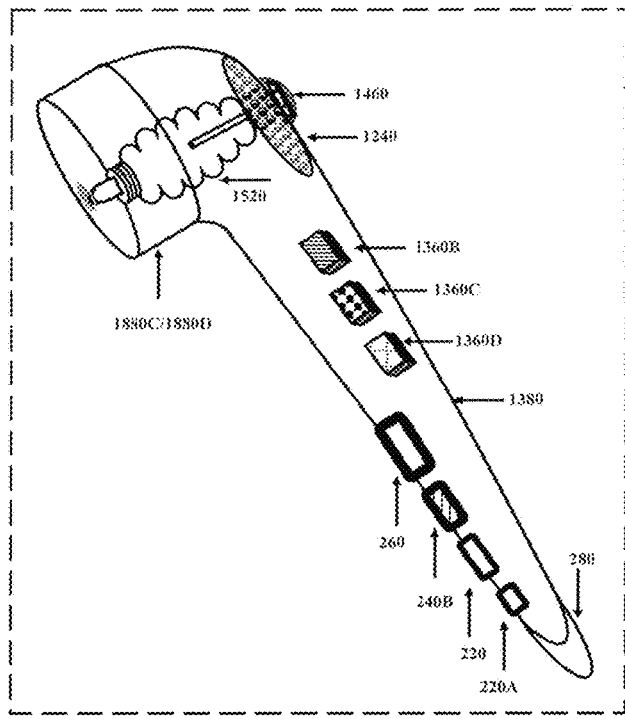
Figure 35C:
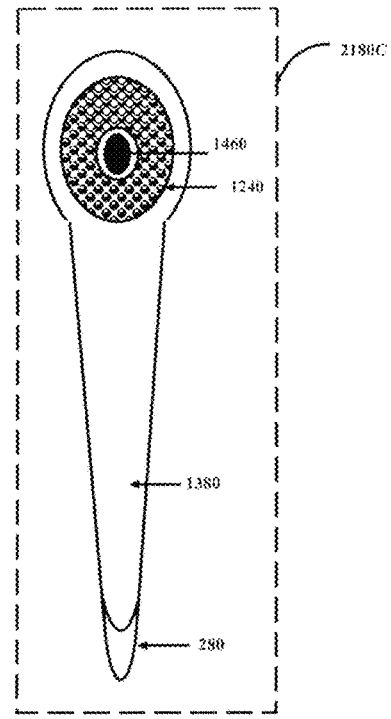

FIGS. 35A-35C are similar to FIGS. 33A-33C respectively, except the detachable spray applicator (based on the ultrasonic wave generator/vibrator) is replaced by the detachable spray applicator (based on the nozzle).

Figure 36A:
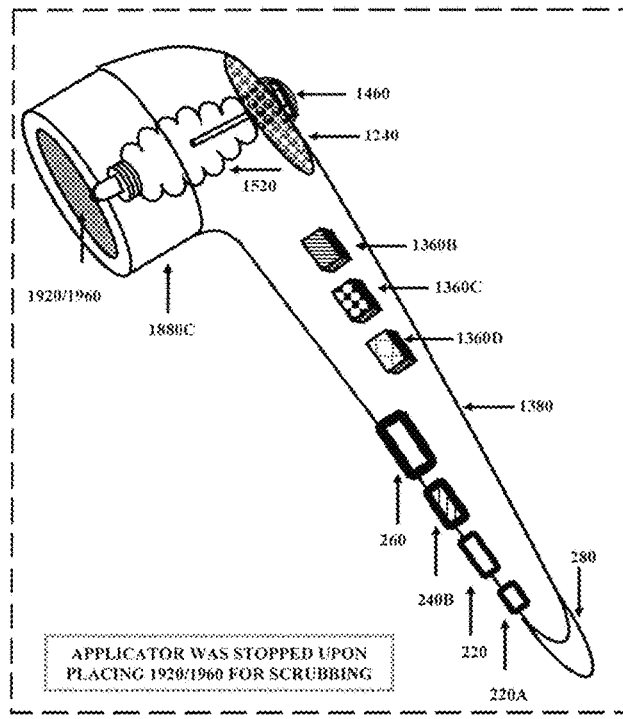
Figure 36B:
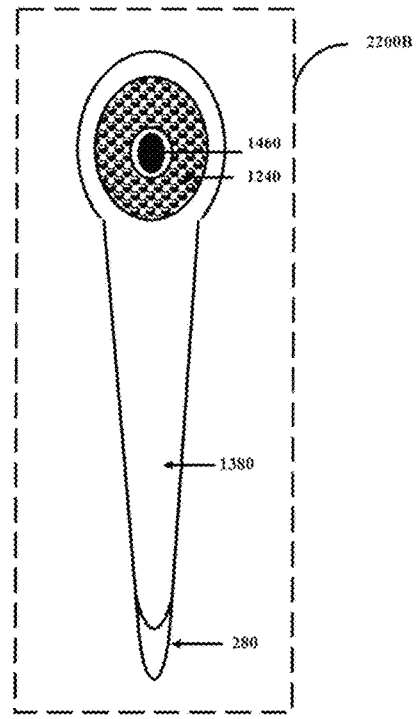

FIG. 36A illustrates a front view of a complete mechanical assembly with the detachable low intensity light module, the detachable spray applicator (based on the nozzle), the particular detachable skin brush unit and the removable fine/coarse textured patch. FIG. 36B illustrates a back view of the complete mechanical assembly (as illustrated in FIG. 36A).

Figure 37A:
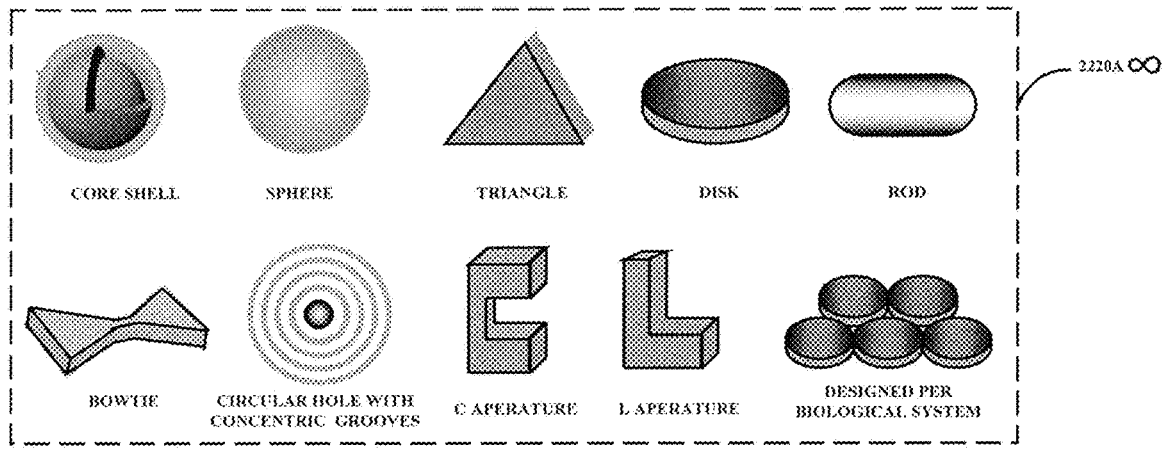
Figure 37B:
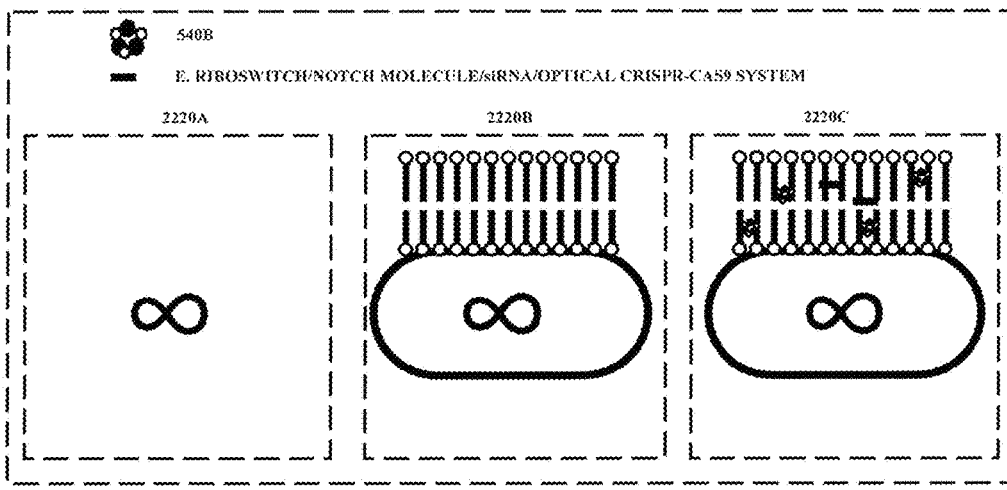
Figure 37C:
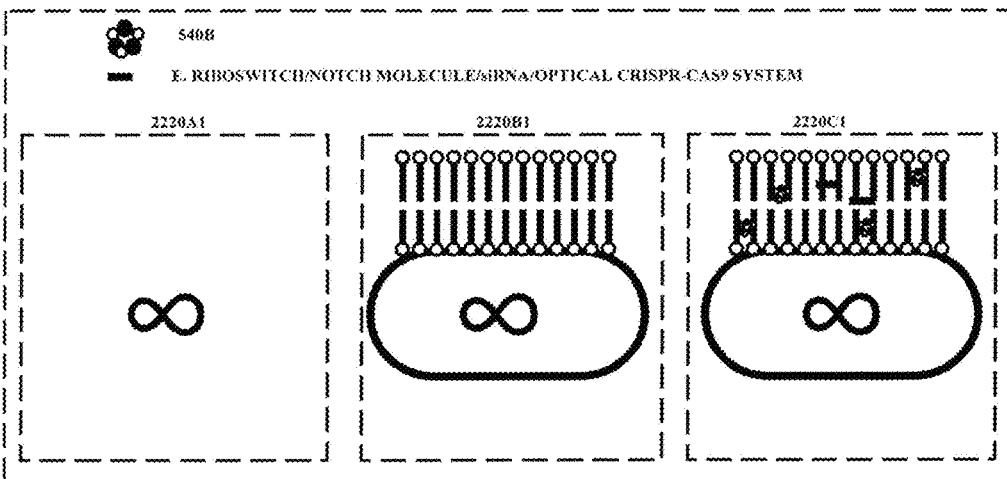

FIG. 37A illustrates various embodiments of nanooptical elements-hereinafter denoted by a symbol of infinity (cc as generalized nanooptical elements). FIG. 37B illustrates additional two embodiments of functionalization of generalized nanooptical elements with the generalized nanooptical elements. FIG. 37C additional two embodiments of functionalization of generalized nanooptical elements (fabricated/constructed in a biocompatible/biodissolvable material) with the generalized nanooptical elements (fabricated/constructed in a biocompatible/biodissolvable material).

FIG. 38A illustrates an embodiment of a nanocarrier decorated with one type of ligand to bind/chemically couple with one type of receptor on a cell. FIG. 38B illustrates another embodiment of a nanocarrier decorated with two types of ligands to bind/chemically couple with two types of receptors on a cell.

FIGS. 39A-39B illustrate delivery of a bioactive compound/biologically active molecule (including a regulatory protein/growth factor) or a mixture of bioactive compounds/biologically active molecules (including regulatory proteins/growth factors) for rejuvenation and protection of skin and the generalized nanooptical elements or generalized (biocompatible/biodissolvable) nanooptical elements into a cell via the two embodiments of the nanocarriers, wherein the nanocarriers encapsulate/cage a bioactive compound/biologically active molecule (including a regulatory protein/growth factor) or a mixture of bioactive compounds/biologically active molecules (including regulatory proteins/growth factors) for rejuvenation and protection of skin and the generalized nanooptical elements or generalized (biocompatible/biodissolvable) nanooptical elements.

Figure 39C:
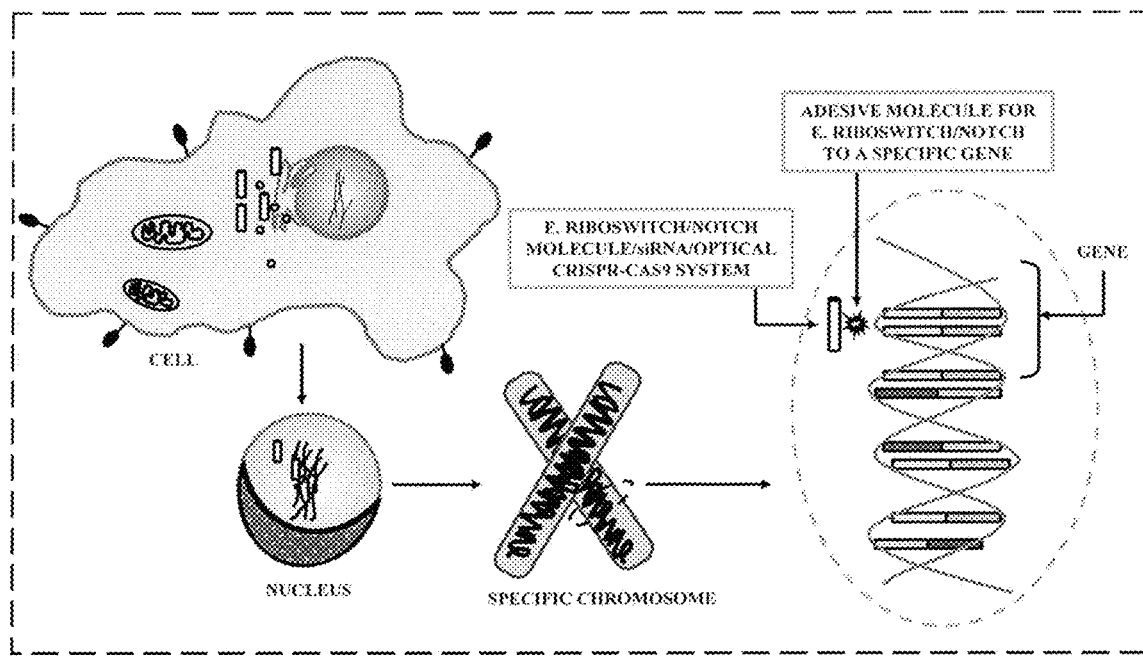

FIG. 39C illustrates binding/chemical coupling of an engineered riboswitch/notch molecule/siRNA/siRNA oligos/siRNAmod/optical CRISPR/Cas9 onto a specific gene.

Figure 39D:
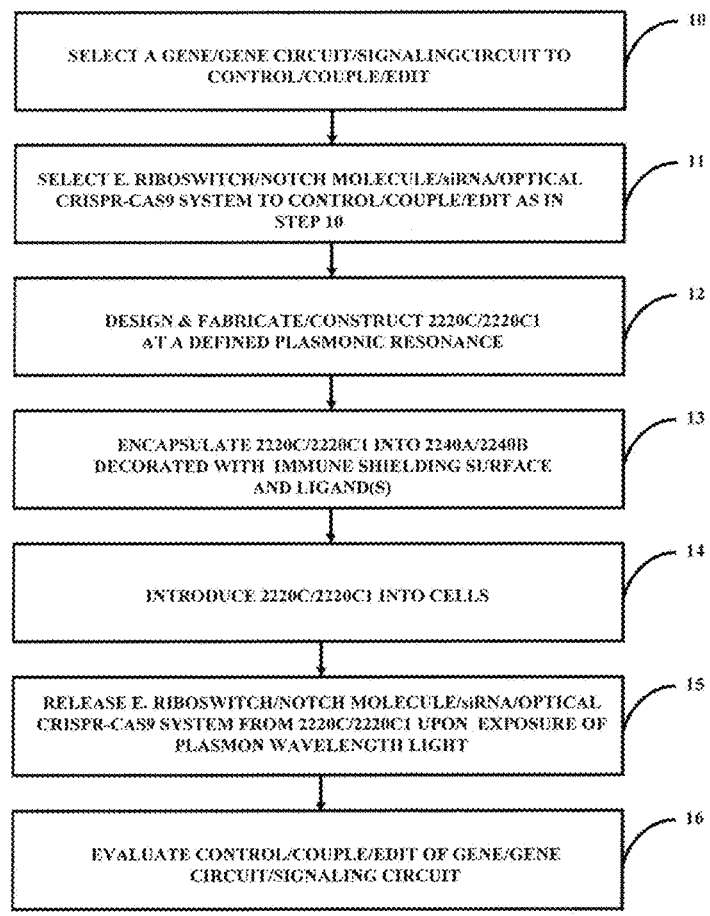

FIG. 39D illustrates a flow chart method to control/chemically couple/edit of a gene, utilizing an engineered riboswitch/notch molecule/siRNA/siRNA oligos/siRNAmod/optical CRISPR/Cas9 into a cell.

Figure 40A:
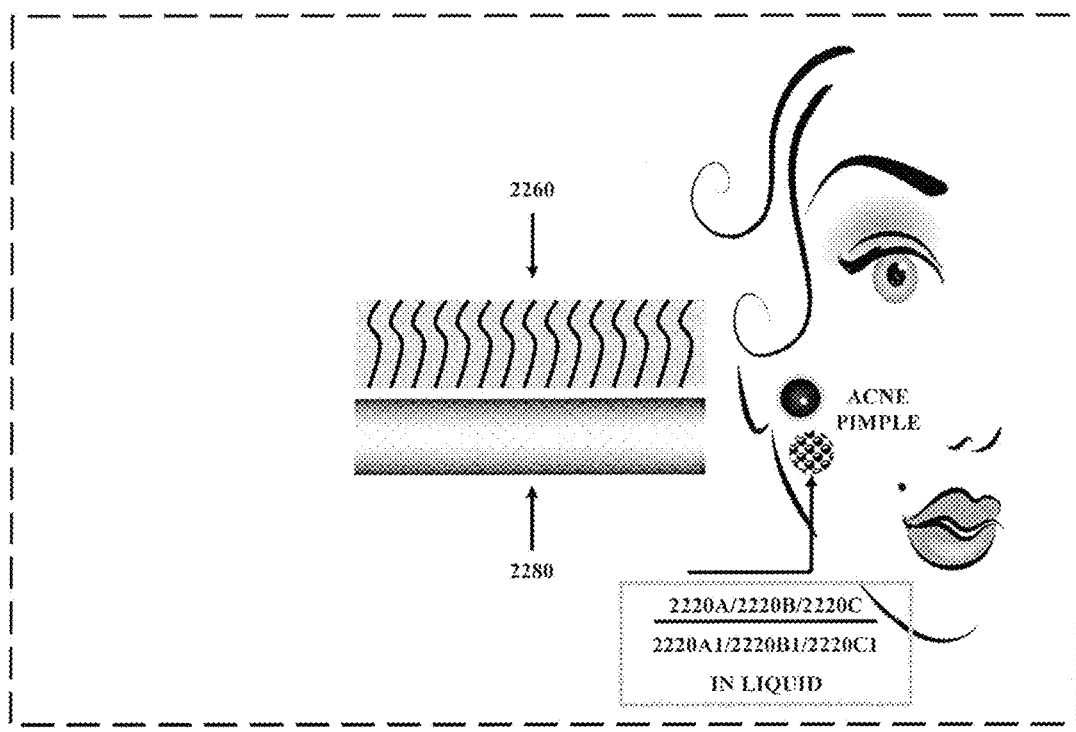

FIG. 40A illustrates a liquid mixed with the generalized nanooptical elements 2220A/2220B/2220C or generalized (biocompatible/biodissolvable) nanooptical elements 2220A1/2220B1/2220C1 into acne pimples for ultrasound wave beam and pulsed laser excitations.

Figure 40B:
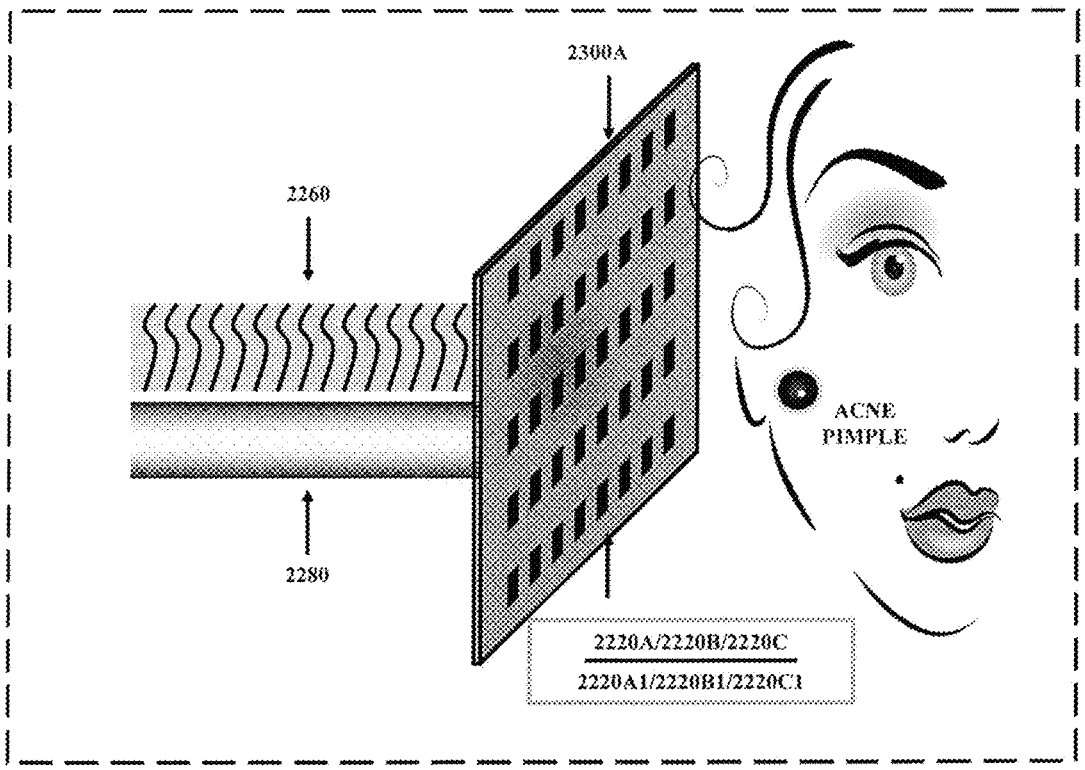

FIG. 40B illustrates a semi-rigid/flexible/conformal substrate comprising/including the generalized nanooptical elements or generalized (biocompatible/biodissolvable) nanooptical elements near acne pimples for ultrasound wave beam and pulsed laser excitations.

Figure 40C:
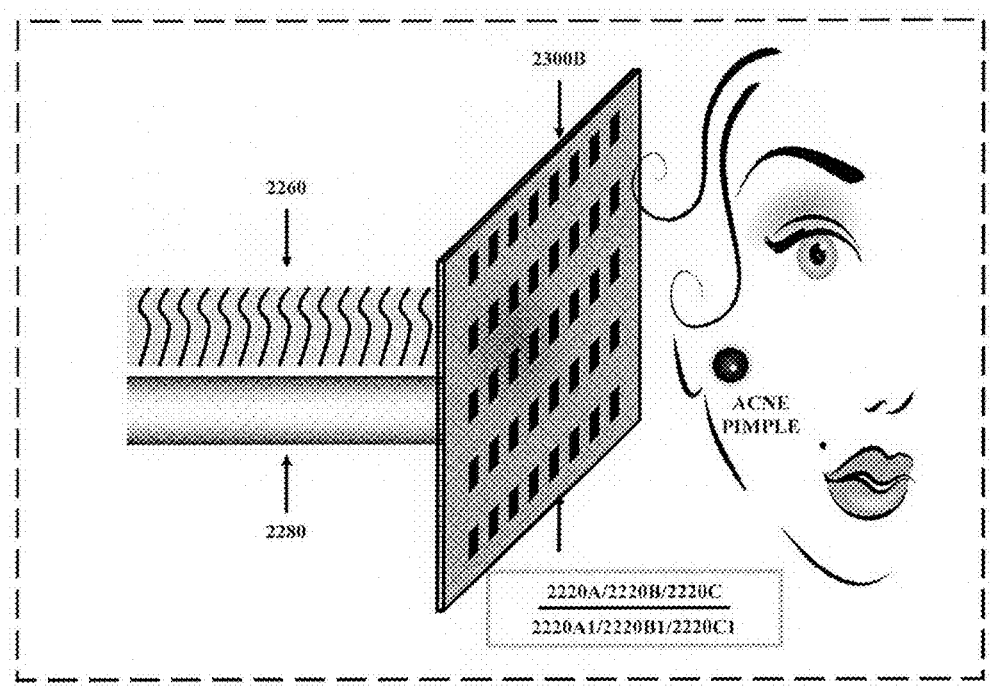

FIG. 40C illustrates a biocompatible/biodissolvable semi-rigid/flexible/conformal substrate (e.g., a pure silk substrate) comprising/including the generalized nanooptical elements or generalized (biocompatible/biodissolvable) nanooptical elements near acne pimples for ultrasound wave beam and pulsed laser excitations.

Figure 40D:
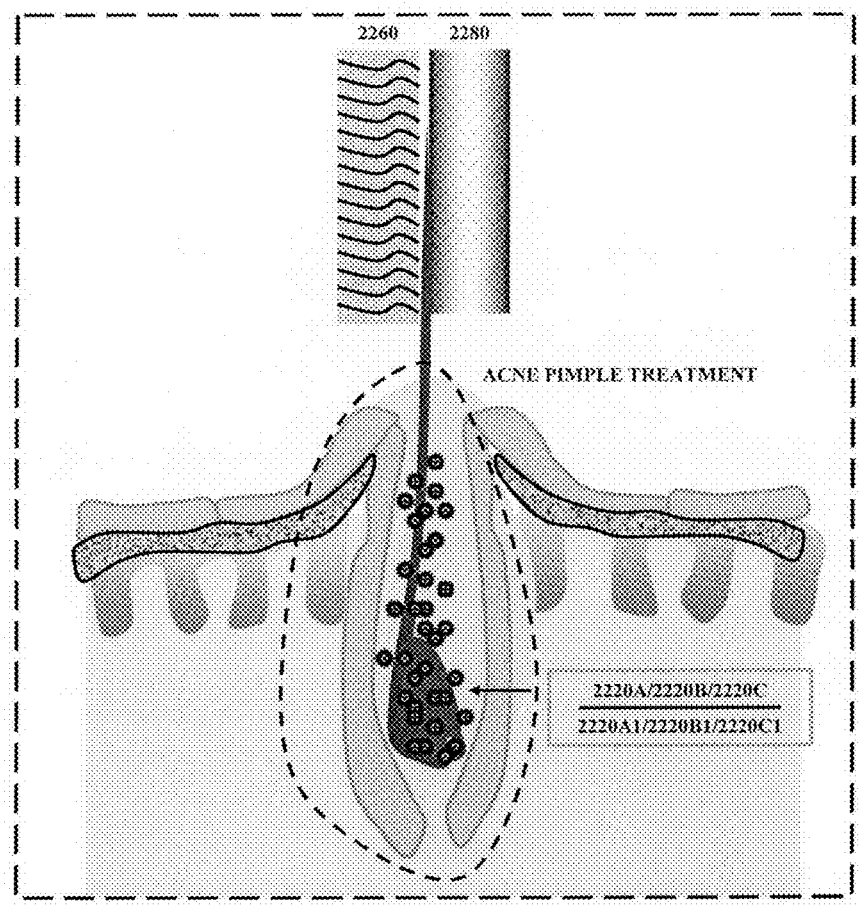

FIG. 40D illustrates an accumulation of the generalized nanooptical elements or generalized (biocompatible/biodissolvable) nanooptical elements at a root of an acne pimple.

Figure 40E:
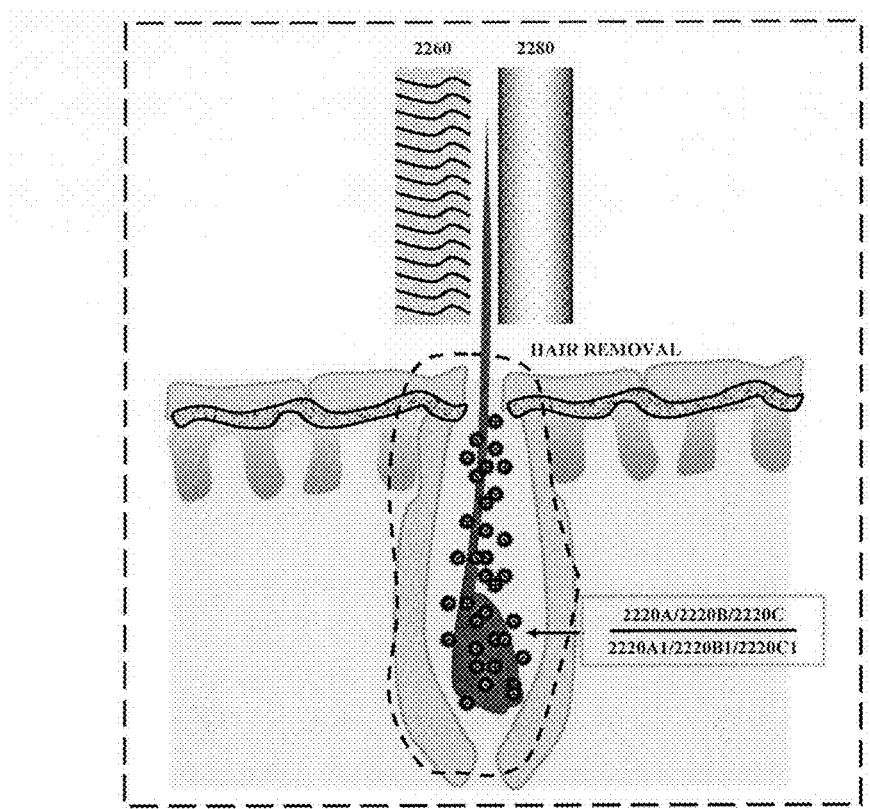

FIG. 40E illustrates an accumulation of the generalized nanooptical elements or generalized (biocompatible/biodissolvable) nanooptical elements at a root of an unwanted hair.

Figure 40F:
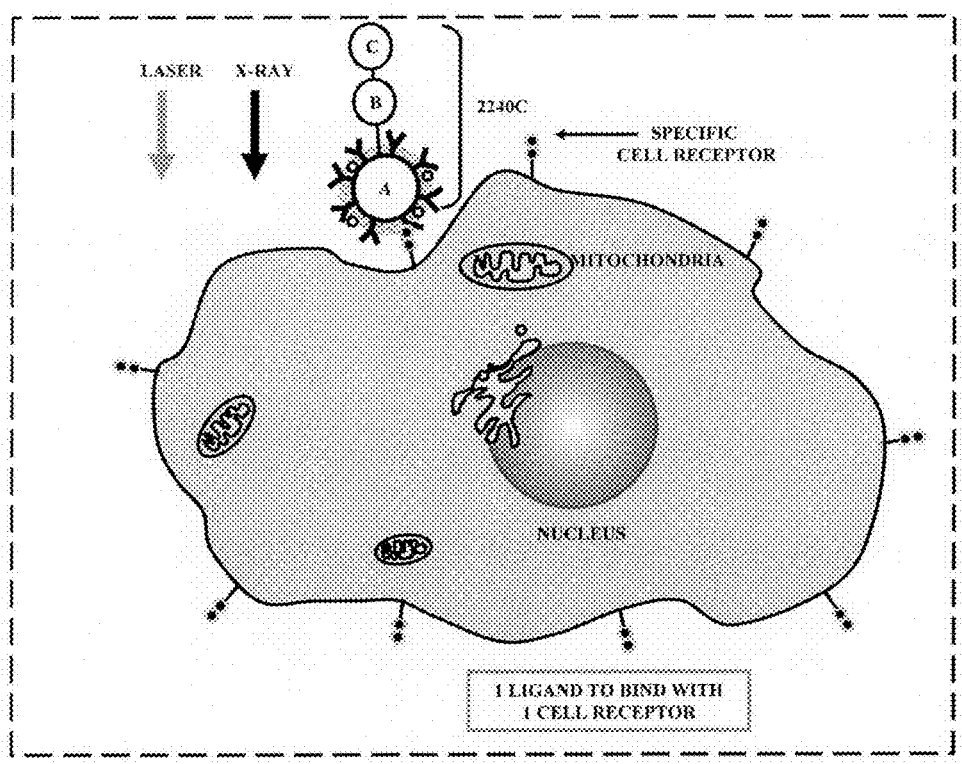

FIG. 40F illustrates an embodiment of a nanosystem, which comprises/includes three nanoshells. The first nanoshell can be a polyethylene-glycol based polymer decorated with a small peptide to bind with specific receptor of a cell. The second nanoshell can be an upconverting nanoshell which converts a (continuous wave/pulsed) laser light of near-infrared wavelength into a (continuous wave/pulsed) laser light of visible wavelength. The third nanoshell can be a cerium fluoride (CeF3) nanoparticle. The first nanoshell can encapsulate/cage a cancer drug and/or an RNAi molecule(s) and/or a photosensitizer and/or extra copies of p53 protein.

Figure 40G:
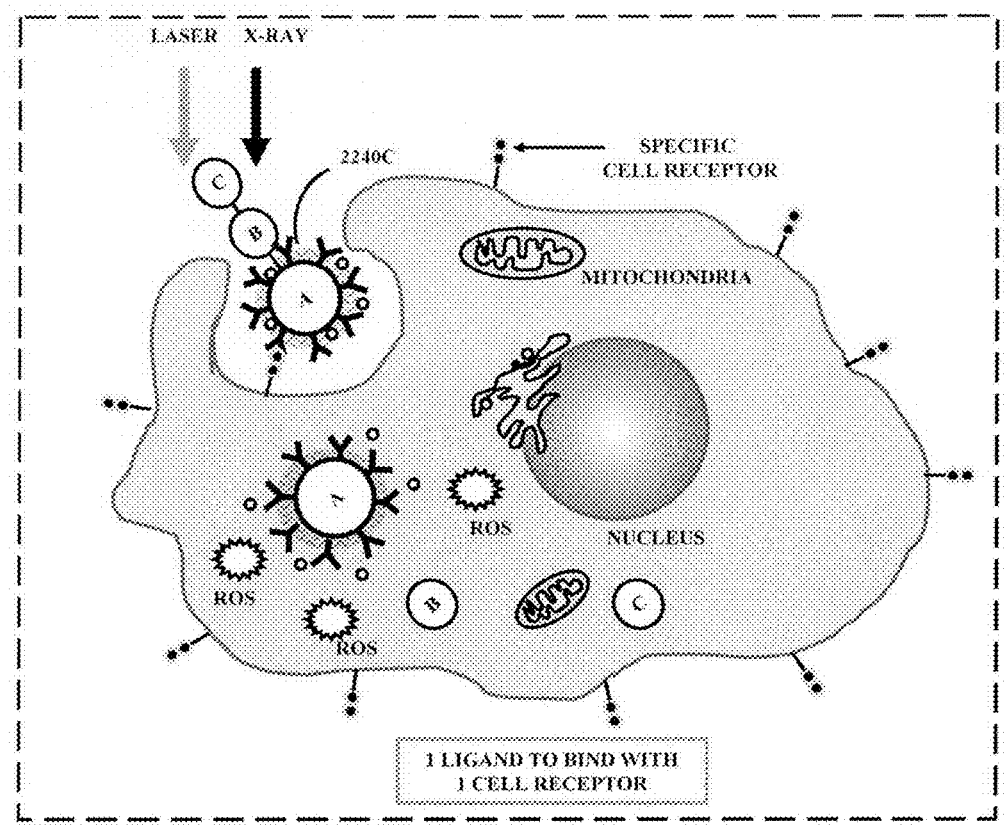

FIG. 40G illustrates destruction of acne pimples/skin cancer cells/cancer cells, when the nanosystem (as illustrated in FIG. 40F) is taken up by acne pimples/skin cancer cells/cancer cells, upon activated/stimulated by a (continuous wave/pulsed) laser light of near-infrared wavelength of a suitable intensity/dose and x-ray of a suitable dose.

Figure 40H:
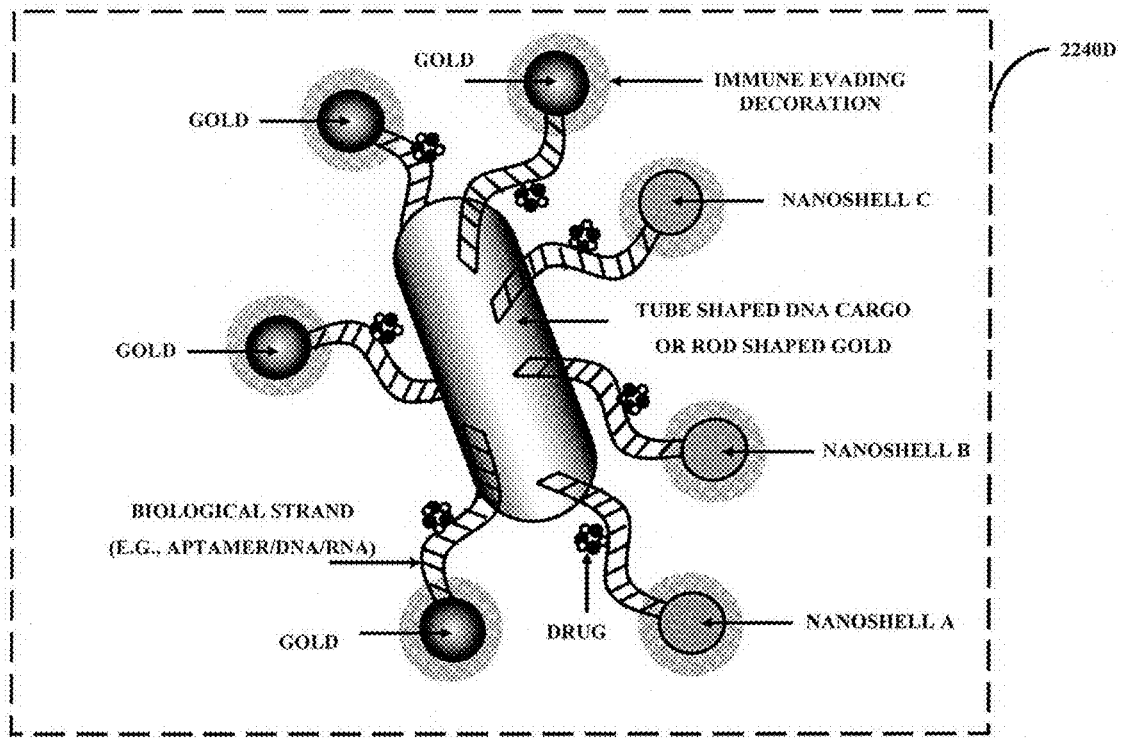

FIG. 40H illustrates another embodiment of a nanosystem, which comprises/includes many nanoshells and many nanoparticles of metal (e.g., gold). Many nanoshells can comprise/include a first nanoshell, a second nanoshell and a third nanoshell. The first nanoshell can be a polyethyleneglycol based polymer decorated with a small peptide to bind with specific receptor of a cell. The second nanoshell can be an upconverting nanoshell which converts a (continuous wave/pulsed) laser light of near-infrared wavelength into a (continuous wave/pulsed) laser light of visible wavelength. The third nanoshell can be a cerium fluoride nanoparticle. The first nanoshell can encapsulate/cage a cancer drug and/or an RNAi molecule(s) and/or a photosensitizer and/or extra copies of p53 protein.

Figure 40I:
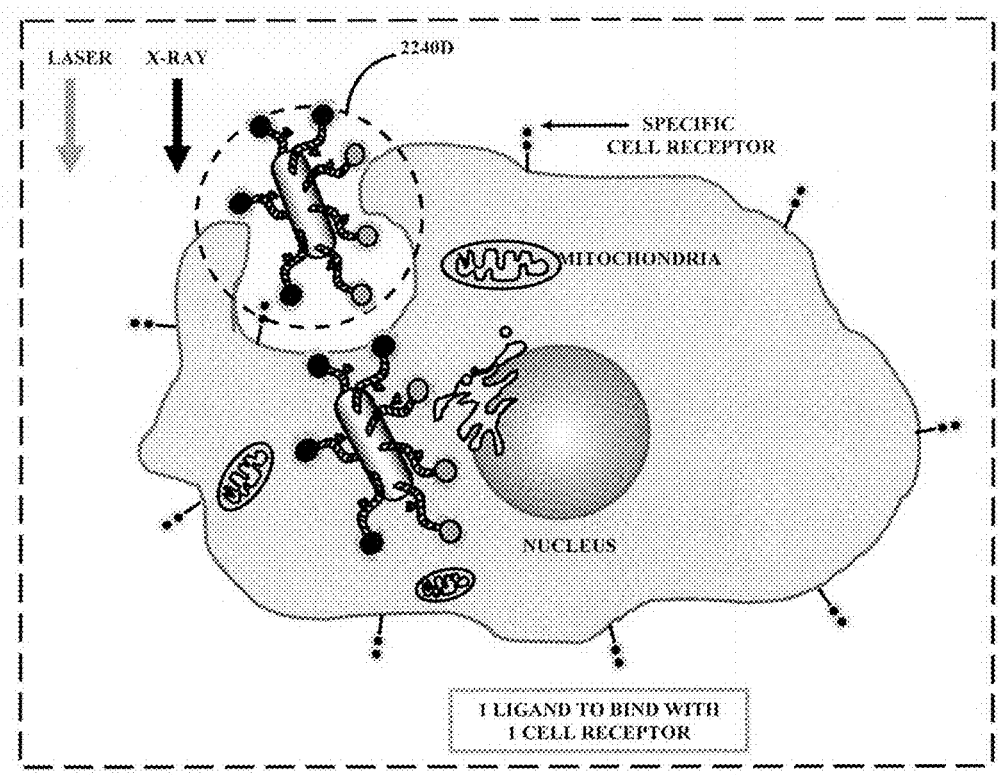
Figure 40J:
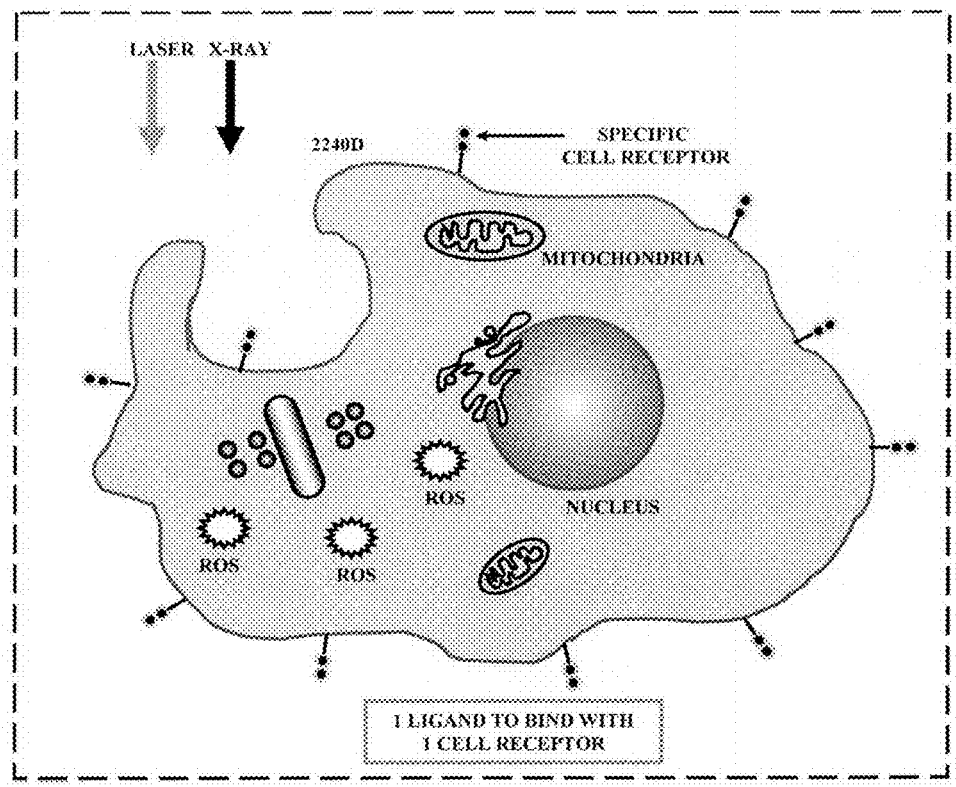

FIGS. 40I-40J illustrate the destruction of acne pimples/skin cancer cells/cancer cells, when the nanosystem (as illustrated in FIG. 40H) is taken up by the acne pimples/skin cancer cells/cancer cells, upon activated/stimulated by a (continuous wave/pulsed) laser light of near-infrared wavelength of a suitable intensity/dose and x-ray of a suitable dose.

Figure 41A:
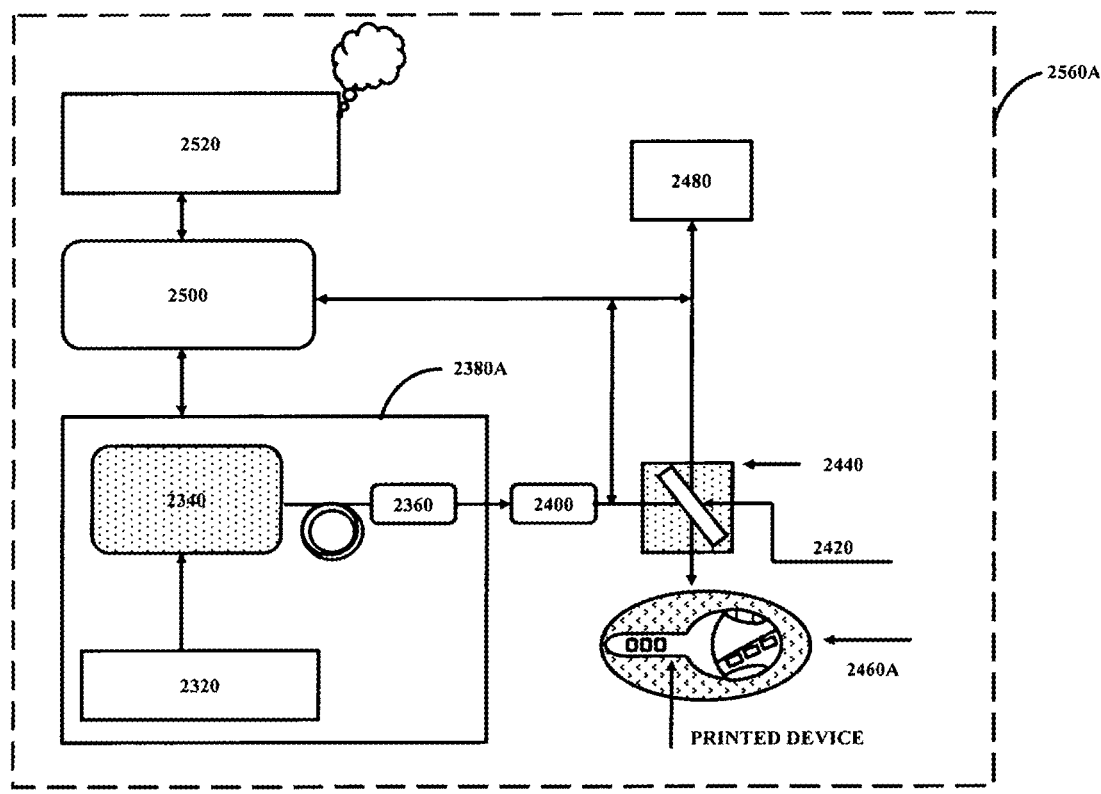

FIG. 41A illustrates an embodiment of a fast three-dimensional (3-D) printer for printing a device (e.g., the mechanical structure of a multifunctional hairbrush device).

Figure 41B:
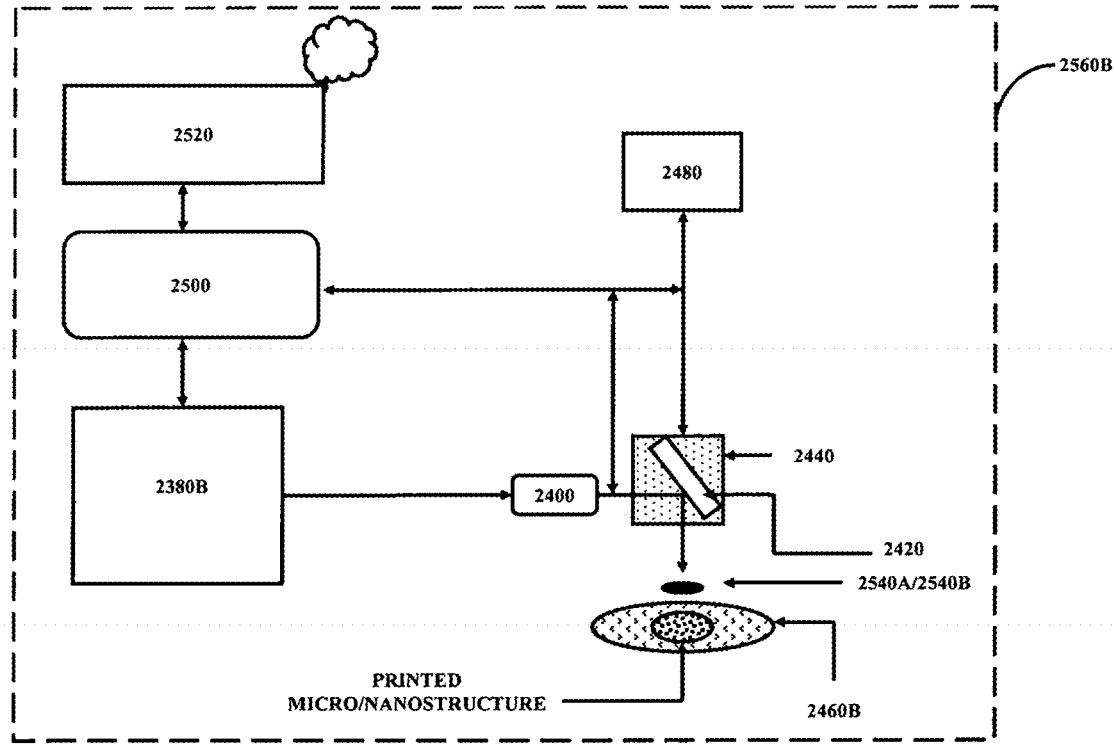

FIG. 41B illustrates an embodiment of a three-dimensional micro/nanoprinter for printing a microstructure/nanostructure.

Figure 42A:
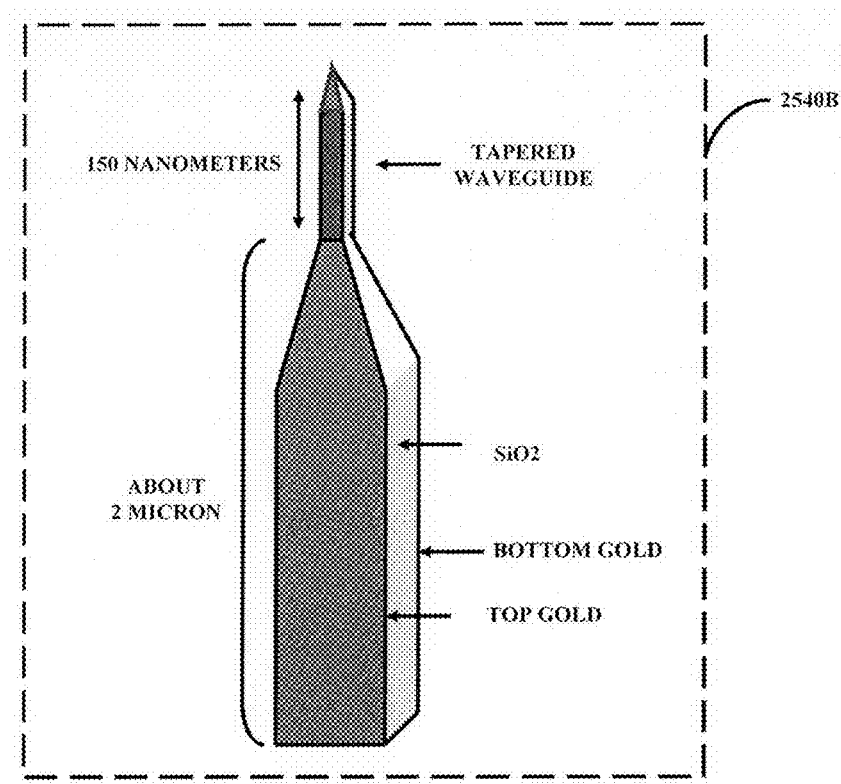
Figure 42B:
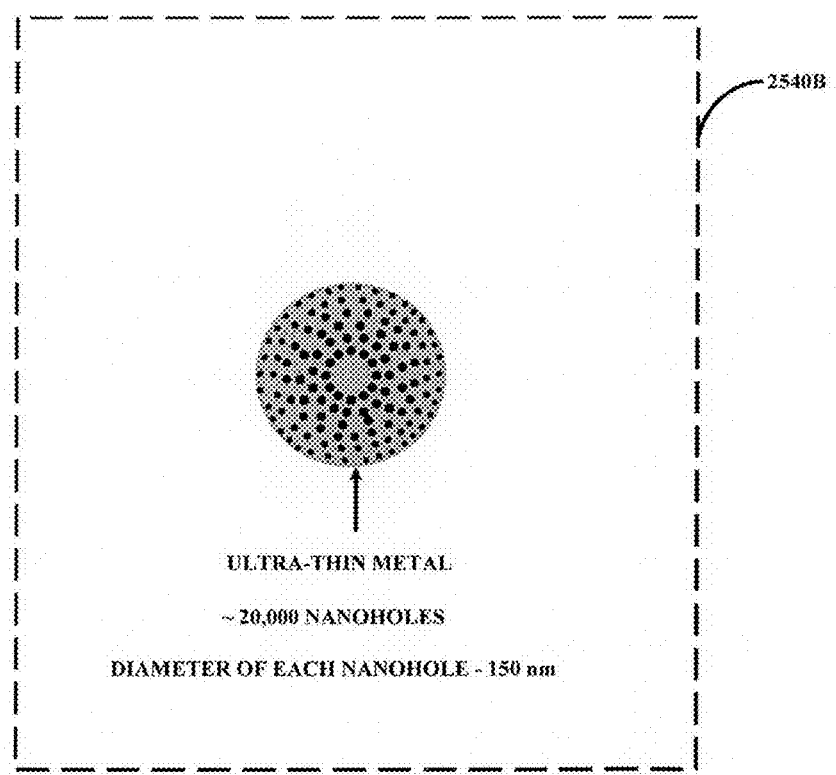

FIGS. 42A-42B illustrate two embodiments of a nanofocusing element for the three-dimensional micro/nanoprinter.

DETAILED DESCRIPTION OF THE DRAWINGS

For Growth and Protection of Hair

Figure 1A:
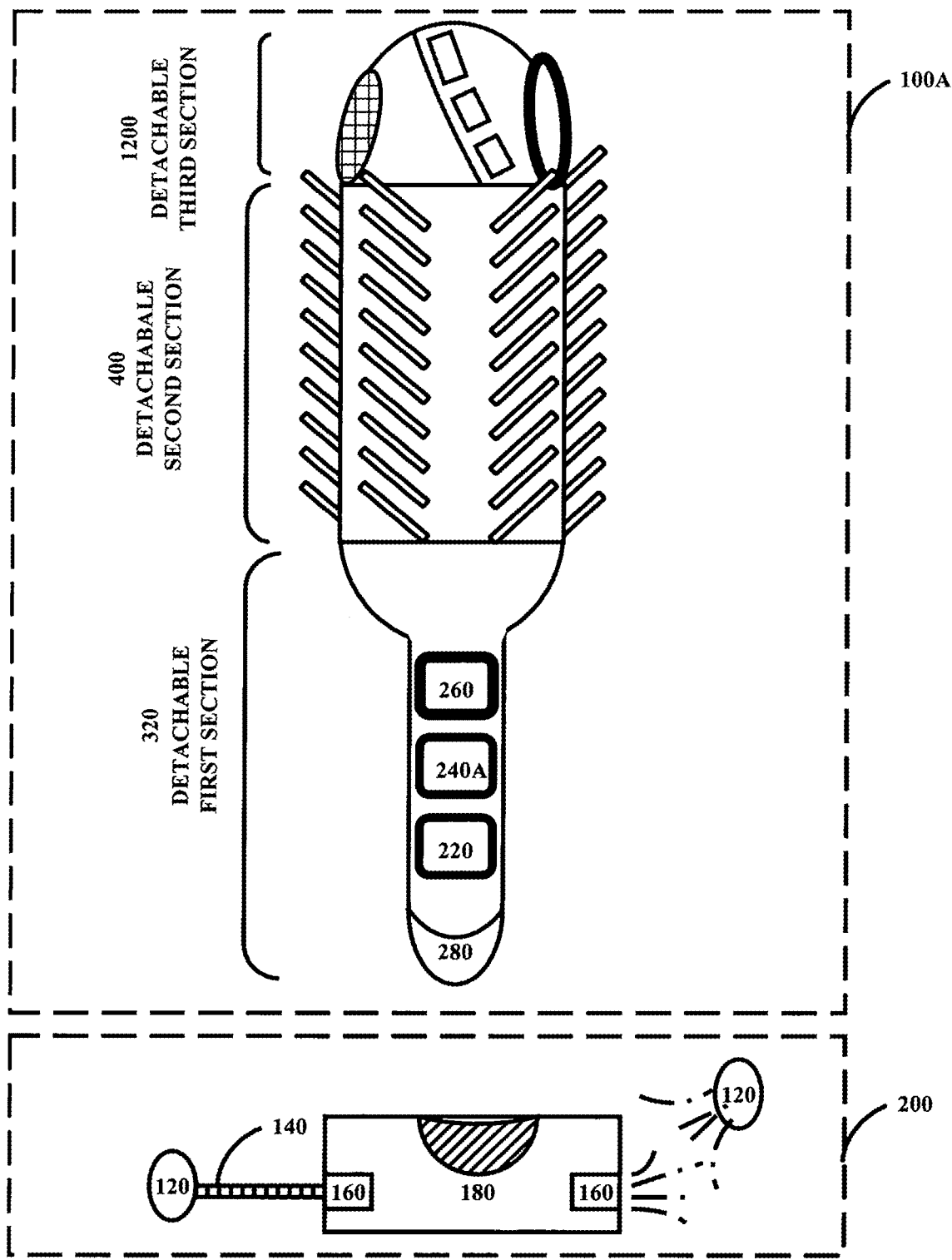
FIGS. 1A-1E illustrate various embodiments of a multifunctional hairbrush.

FIG. 1A illustrates an embodiment of a hairbrush 100A and an electrical/wireless charging (including electromagnetically charging through air) unit 200. The hairbrush 100A comprises/includes (a) a detachable first section 320, (b) a detachable second section (bristles' section) 400 and (c) a detachable third section (hair dryer) 1200. The detachable second section (bristles') 400 can enable vibration within a range of frequencies (e.g., between 40 Hz-100 Hz).

Figure 1B:
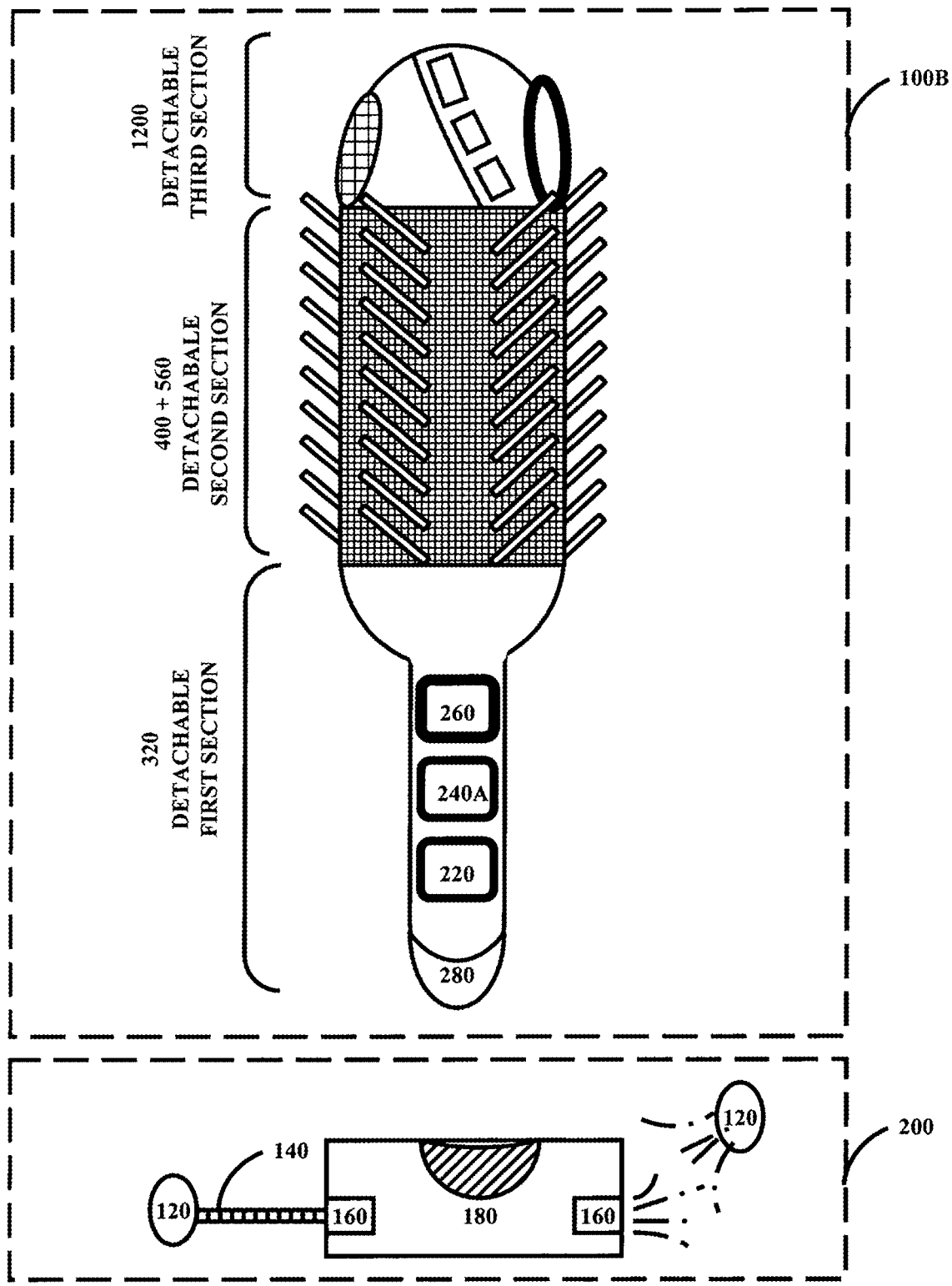

FIG. 1B illustrates another embodiment of a hairbrush 100B and the electrical/wireless charging (including electromagnetically charging through air) unit 200. The hairbrush 100B comprises/includes (a) the detachable first section 320, (b) the detachable second section (bristles' section) 400 with a removable/stretchable integrated mesh structured net 560 (which can be infused with a bioactive compound/biologically active molecule (including a regulatory protein/growth factor) or a mixture of bioactive compounds/biologically active molecules (including regulatory proteins/growth factors) 540A for growth and protection of hair) and (c) the detachable third section (hair dryer) 1200. The detachable second section (bristles') 400 can enable vibration within a range of frequencies (e.g., between 40 Hz-100 Hz).

The above bioactive compound/botanical compound/biologically active molecule (including a regulatory protein/growth factor) or the mixture of bioactive compounds/botanical compounds/biologically active molecules (including regulatory proteins/growth factors) 540A for growth and protection of hair can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

By way of an example and not by way of any limitation, a nanoshell can be a boron nitride nanotube, carbon nanotube, Cornell-dot, cubisome, dendrimer (including plant based dendrimer), deoxyribonucleic acid (DNA) origami nanostructure, ethosomes, exosome, fullerene $C_{60}$ (e.g., a malonic acid derivative of $C_{60}$), gold nanoparticles (suitably coated), grapefruit-derived nanovector (GNV), hollow magnetic cage molecule (e.g., $Co_{12}C_6$, $Mn_{12}C_6$ and $Mn_{24}C_{18}$), lipidoid, liposome, mesoporous silica, micelle, nanocrystal, niosome, polysebacic acid (PSA), polysilsesquioxane (PSQ), porous silicon photonic crystal, quantum dot, quantum dot capped with glutathione, ribonucleic acid (RNA) origami nanostructure, self-assembling peptide (or self-assembling protein), solid-lipid nanoparticle, spherical nucleic acid (SNA), synthasome, tubular/tetrahedral/other suitable structure fabricated/constructed, utilizing DNA/RNA origami process, virus, zein-plant protein and zeolite-l-nanocrystal.

The removable/stretchable integrated mesh structured net 560 can comprise/include a scaffold/microscaffold/nanoscaffold. Furthermore, the removable/stretchable integrated mesh structured net 560 can be replaced by a scaffold/microscaffold/nanoscaffold.

The scaffold/microscaffold/nanoscaffold can be infused with a bioactive compound/biologically active molecule (including a regulatory protein/growth factor) or a mixture of bioactive compounds/biologically active molecules (including regulatory proteins/growth factors) 540A for growth and protection of hair. The bioactive compound/botanical compound/biologically active molecule (including a regulatory protein/growth factor) or the mixture of bioactive compounds/botanical compounds/biologically active molecules (including regulatory proteins/growth factors) 540A can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

Figure 1C:
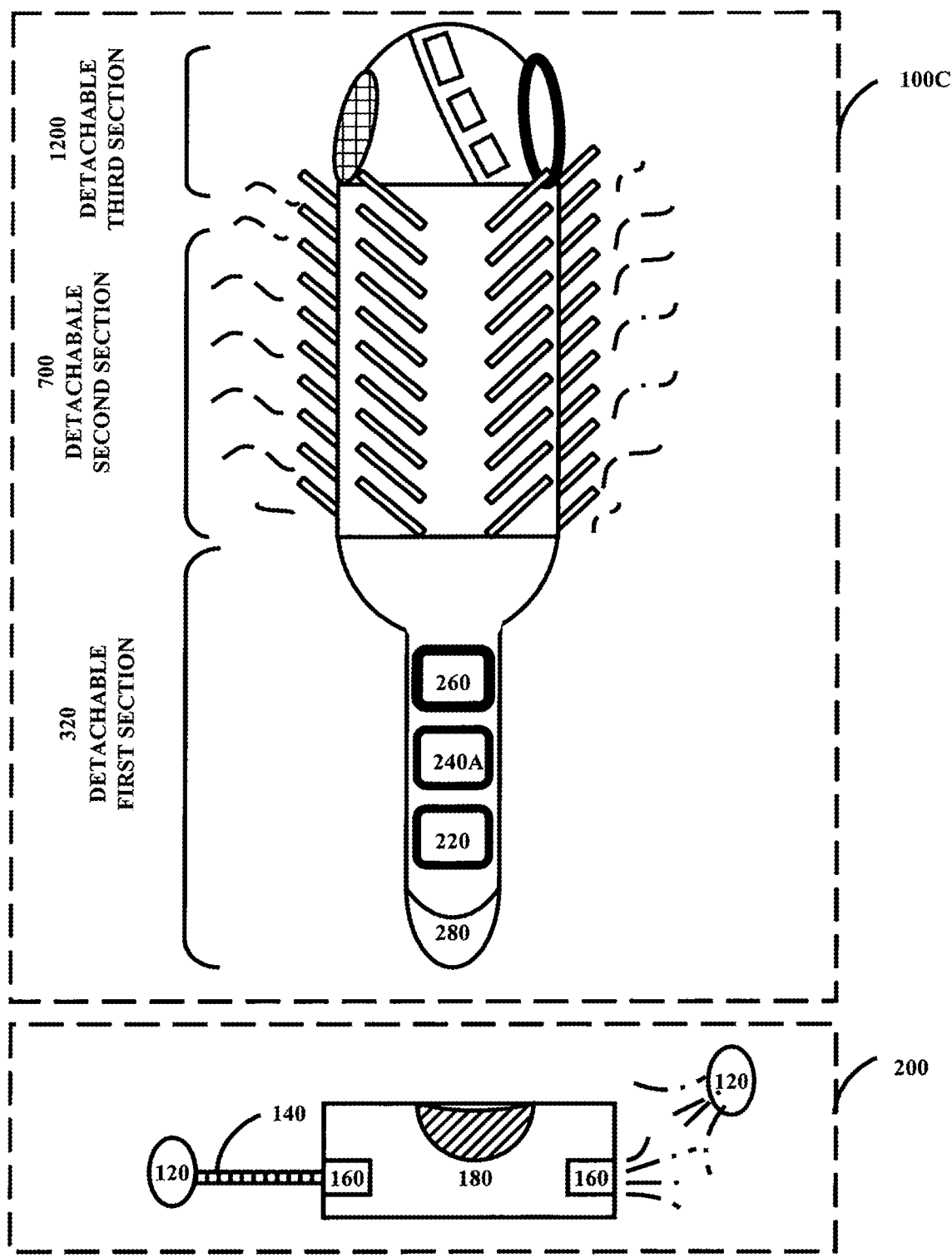

FIG. 1C illustrates another embodiment of a hairbrush 100C and the electrical/wireless charging (including electromagnetically charging through air) unit 200. The hairbrush 100C comprises/includes (a) the detachable first section 320, (b) a detachable second section (a detachable hair/scalp massager integrated with bristles) 700 and (c) the detachable third section (hair dryer) 1200. The detachable second section (the detachable hair/scalp massager integrated with bristles) 700 can enable vibration within a range of frequencies (e.g., between 40 Hz-100 Hz).

Figure 1D:
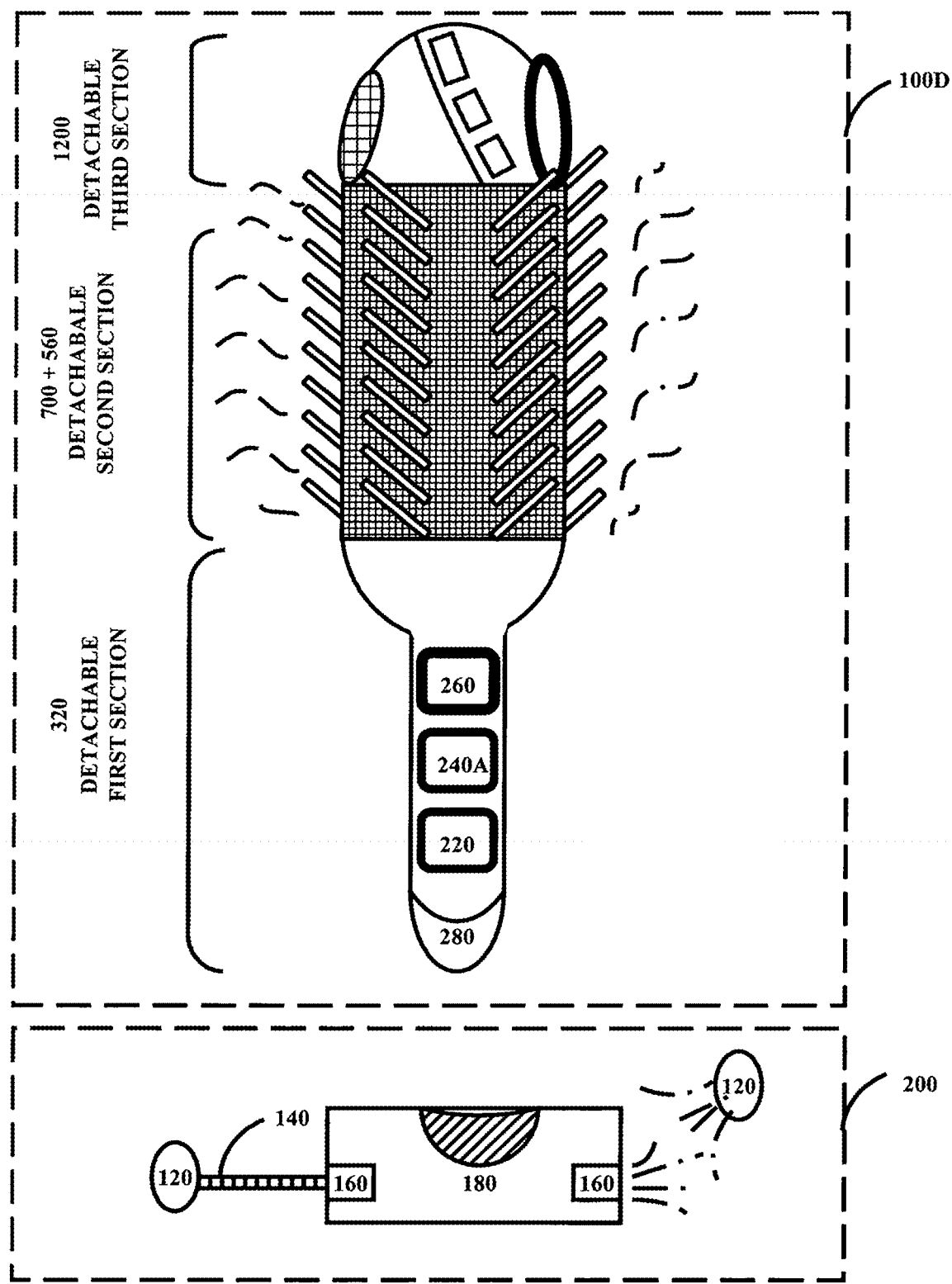

FIG. 1D illustrates another embodiment of a hairbrush 100D and the electrical/wireless charging (including electromagnetically charging through air) unit 200. The hairbrush 100D comprises/includes (a) the detachable first section 320, (b) the detachable second section (the detachable hair/scalp massager integrated with bristles) 700 with the removable/stretchable integrated mesh structured net 560 and (c) the detachable third section (hair dryer) 1200. The detachable second section (the detachable hair/scalp massager integrated with bristles) 700 can enable vibration within a range of frequencies (e.g., between 40 Hz-100 Hz).

Figure 1E:
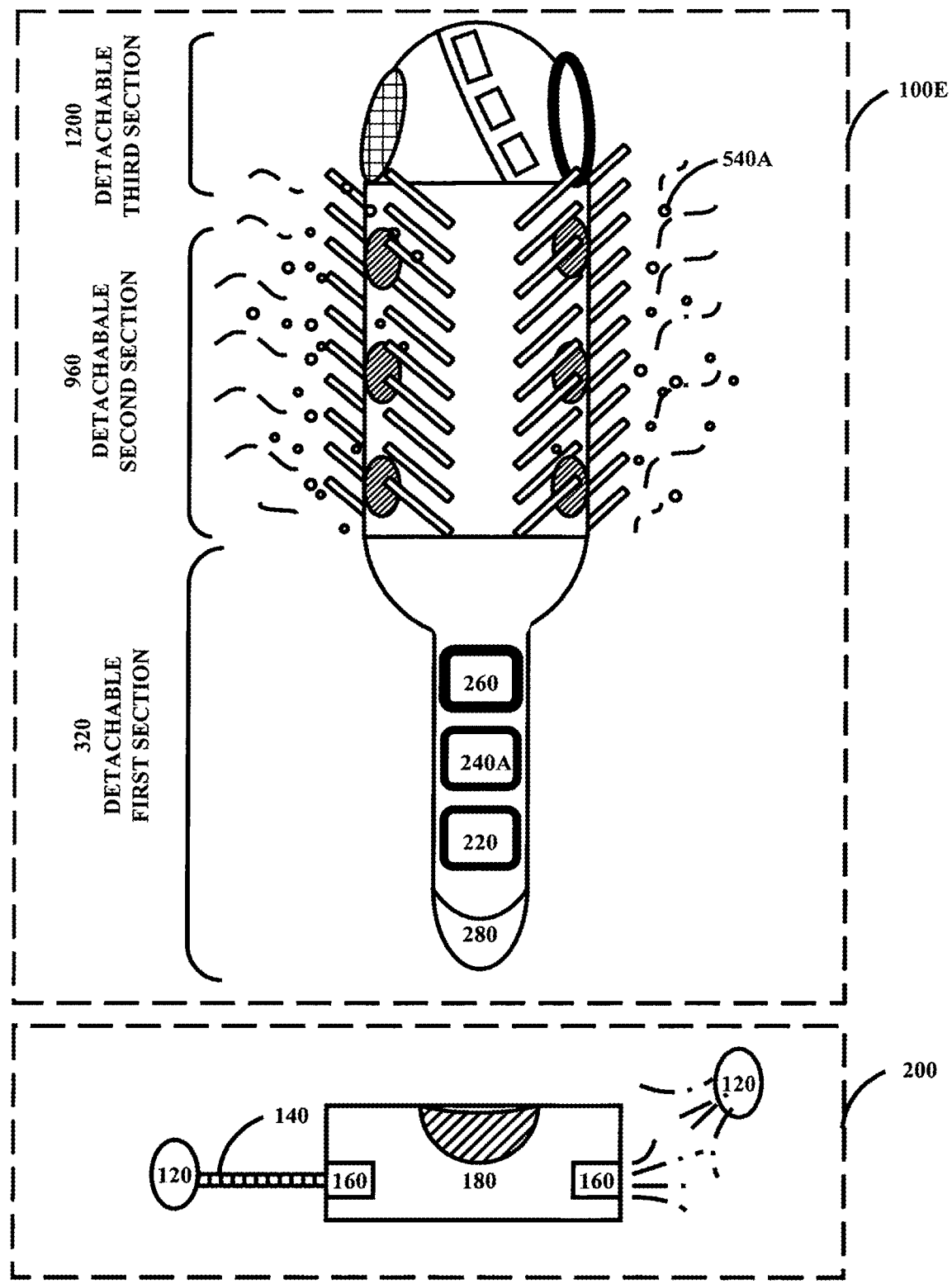

FIG. 1E illustrates another embodiment of a hairbrush 100E and the electrical/wireless charging (including electromagnetically charging through air) unit 200. The hairbrush 100E comprises/includes (a) the detachable first section 320, (b) a detachable second section (a detachable spray applicator and a detachable vibrator integrated with bristles) 960 and (c) the detachable third section (hair dryer) 1200. The detachable second section (the detachable spray applicator and the detachable vibrator integrated with bristles) 960 can enable vibration within a range of frequencies (e.g., between 40 Hz-100 Hz).

The spray applicator can spray a bioactive compound/botanical compound/biologically active molecule (including a regulatory protein/growth factor) or a mixture of bioactive compounds/botanical compounds/biologically active molecules (including regulatory proteins/growth factors) 540A in a liquid.

The above bioactive compound/botanical compound/biologically active molecule (including a regulatory protein/growth factor) or the mixture of bioactive compounds/botanical compounds/biologically active molecules (including regulatory proteins/growth factors) 540A can be encapsulated within a nanoshell. The nanoshell can comprise/include ligand(s) to bind/chemically couple with specific receptors of a type. Furthermore, the above bioactive compound/botanical compound or the mixture of bioactive compounds/botanical compounds can be in an emulsion/microemulsion/nanoemulsion.

Figure 2A:
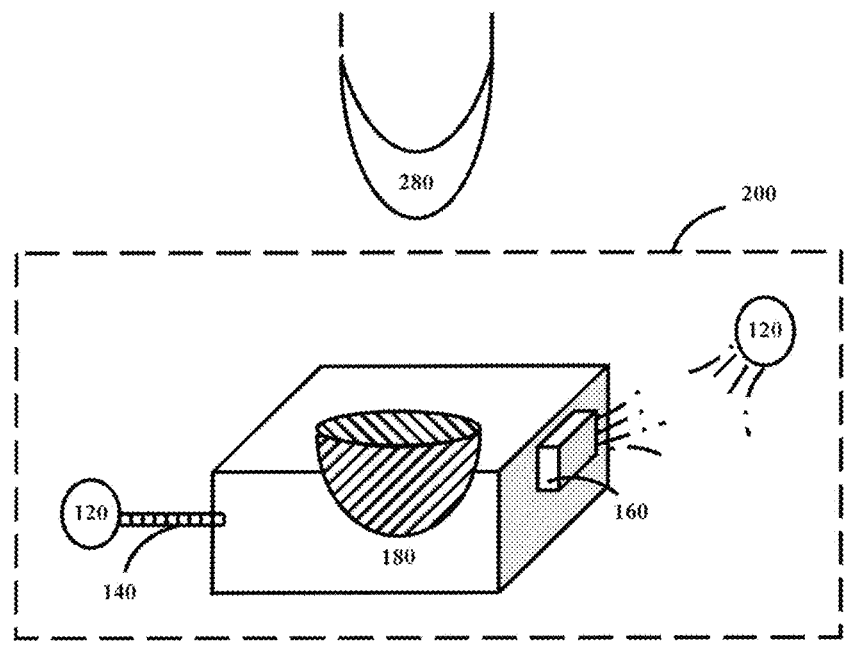
FIG. 2A illustrates an electrical/wireless charging (including electromagnetically charging through air) unit.

FIG. 2A illustrates the wired/wireless charging (including electromagnetically charging through air) unit 200, wherein an electrical wall plug/socket is 120, an electrical cable/retractable electrical cable is 140, a wireless charger (including electromagnetically charging through air) is 160 and a charging socket is 180 for a bottom electrical contact area 280 of the hairbrush 100A/100B/100C/100D/100E in an upright position.

A power base station can be plugged into the electrical wall plug/socket 120. The power base station can emit low-frequency (4 MHz to 10 MHz) electromagnetic radiation. A power harvesting circuit on the bottom electrical contact area 280 can resonate at the same frequency emitted by the power base station. When the bottom contact area 280 comes in close proximity to the power base station, the bottom contact area 280 absorbs the energy via electromagnetic coupling-thus enabling electromagnetically charging through air.

Figure 2B:
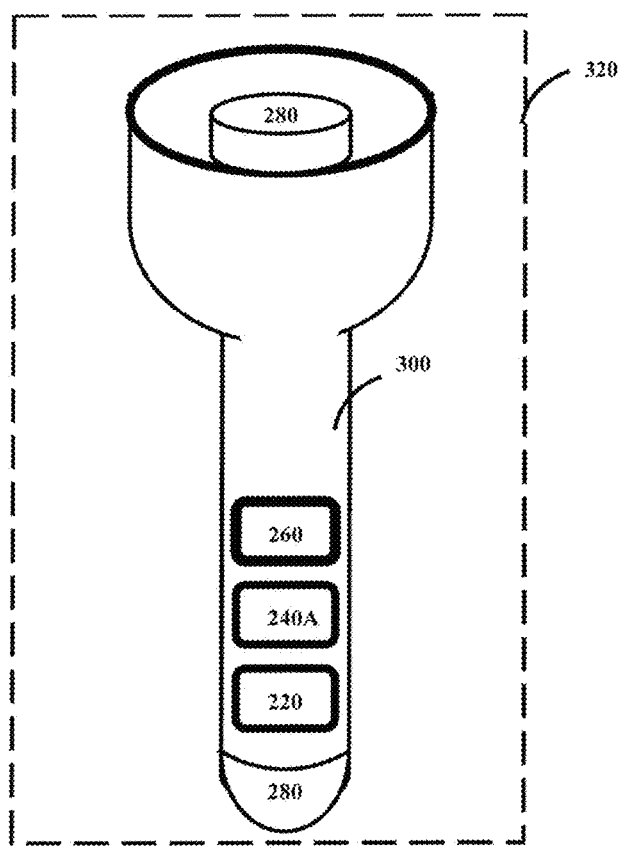
FIG. 2B illustrates a detachable first section of the various embodiments of a multifunctional hairbrush.

FIG. 2B illustrates the detachable first section 320, which comprises/includes (a) a power indicator 220, (b) a vibration (due to the ultrasonic wave generator/vibrator) intensity indicator 240A, (c) a spray indicator 260, (d) a top electrical contact area 280, (e) the bottom electrical contact area 280 and (f) an upright stand 300.

Figure 2C:
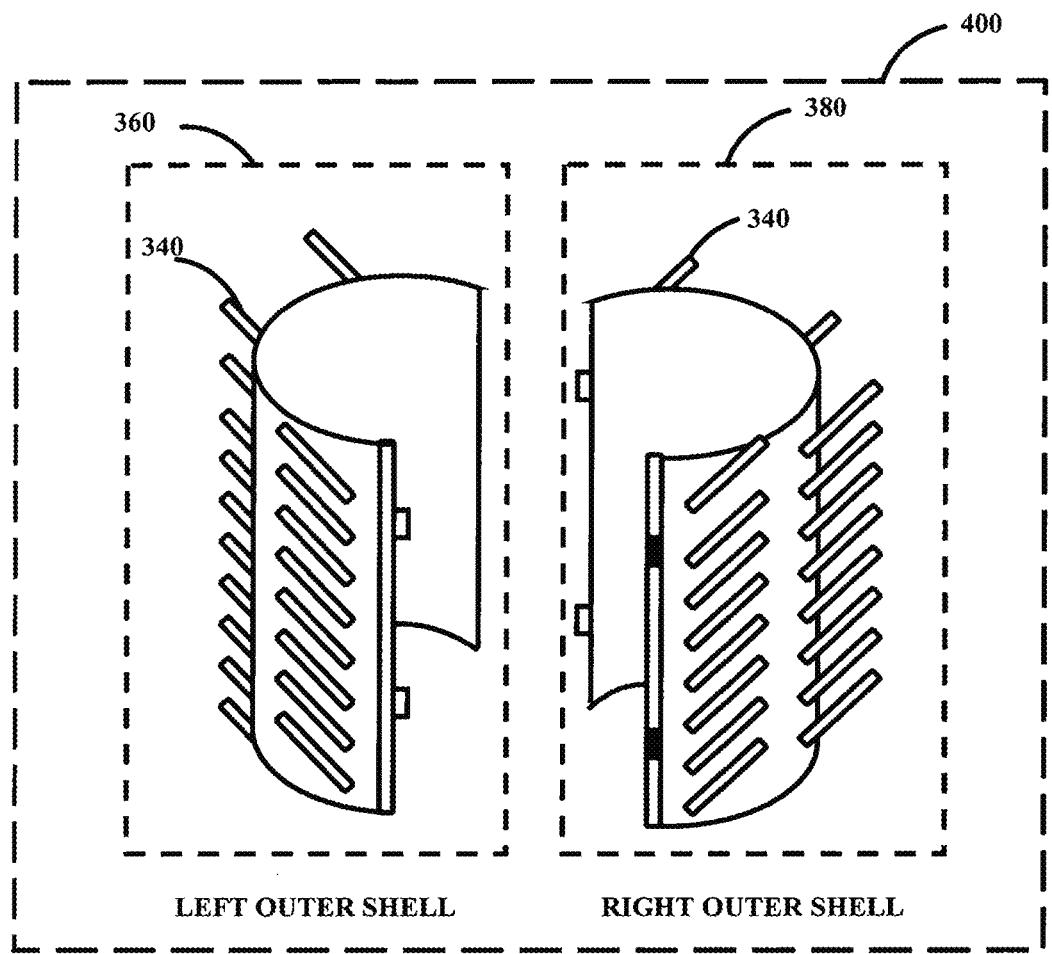
FIG. 2C illustrates an embodiment of detachable bristles' section.

FIG. 2C illustrates a detachable bristles' section 400, wherein the left outer shell is indicated by 360 and right outer shell is indicated by 380. Both left outer shell 360 and right outer shell 380 can have bristles, wherein each bristle is indicated by 340. An ultrasound wave generator/vibrator can be connected to the left outer shell 360 and/or the right outer shell 380—thus enabling the detachable bristles' section 400 to vibrate.

Figure 2D:
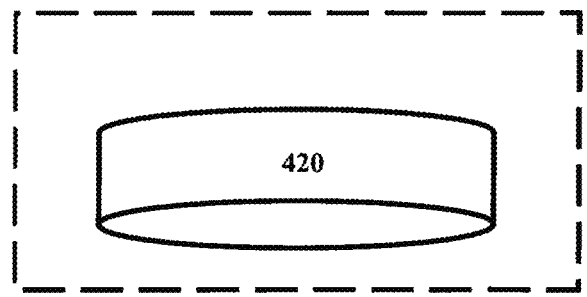
FIG. 2D illustrates a detachable cap.

FIG. 2D illustrates a detachable cap 420.

Figure 2E:
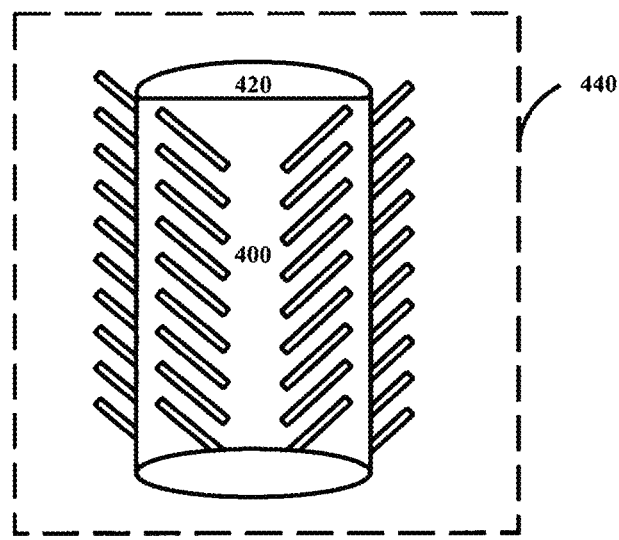
FIG. 2E illustrates a detachable second section, which comprises/includes the detachable bristles' section (as illustrated in FIG. 2C) and the detachable cap (as illustrated in FIG. 2D).

FIG. 2E illustrates a detachable second section 440, which comprises/includes (a) the detachable bristles' section 400 and (b) the detachable cap 420.

Figure 2F:
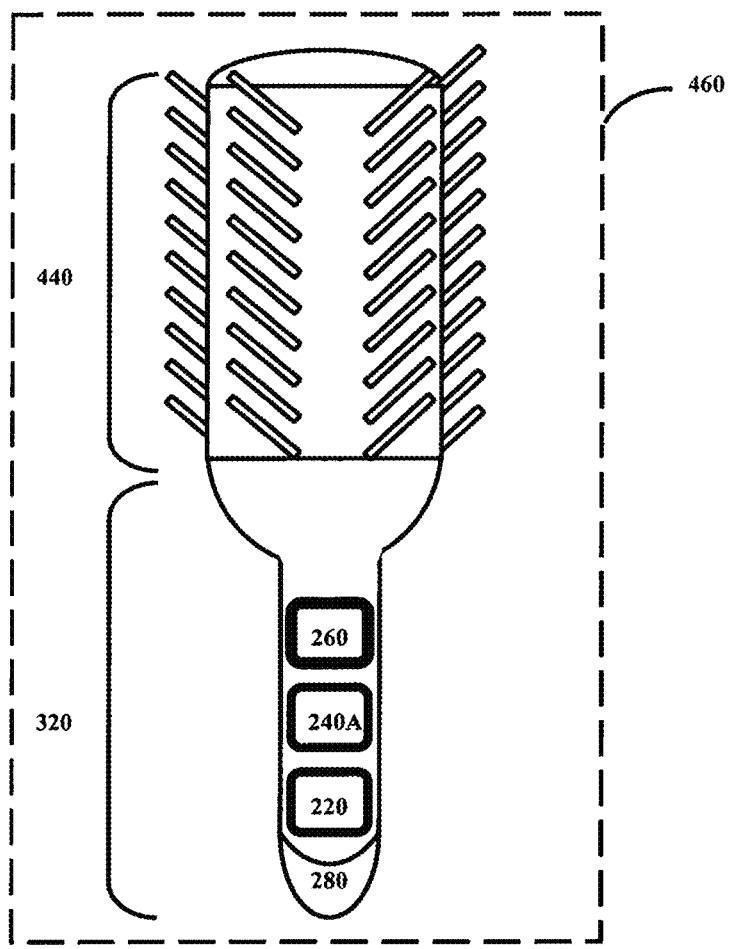
FIG. 2F illustrates another embodiment of a multifunctional hairbrush, which comprises/includes the detachable first section (as illustrated in FIG. 2B) and the detachable second section (as illustrated in FIG. 2E).

FIG. 2F illustrates a hairbrush 460, which comprises/includes (a) the detachable first section 320 and (b) the detachable second section with bristles' 440.

Figure 3A:
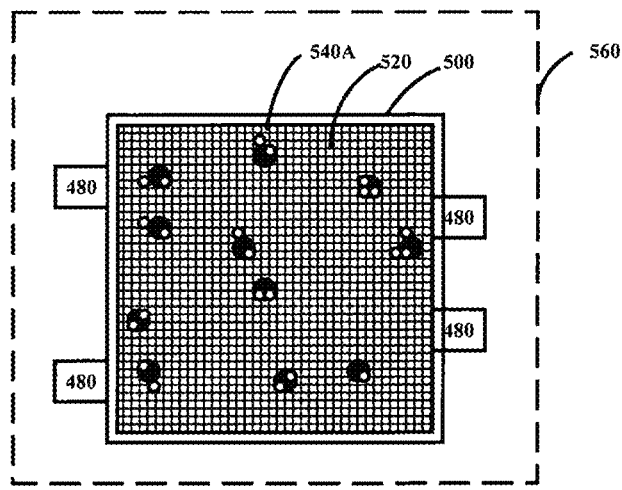
FIG. 3A illustrates a removable/stretchable integrated mesh structured net.

FIG. 3A illustrates a removable/stretchable integrated mesh structured net 560, which comprises/includes a sticker 480, an elastic frame 500 (configured to fit the contour of a hairbrush/comb) and a removable/stretchable mesh structured net (of a suitable material) 520.

By way of an example and not by way of any limitation, the compositions for the removable/stretchable structured net 520 can be described in Table 1, Table 2, Table 3 and Table 4.

TABLE 1

| Composition No. | Wt % Material A | Wt % Material B |
|---|---|---|
| 1 | 80% Hydrogel | 20% Chitosan |
| 2 | 80% Hydrogel | 20% Chitin |
| 3 | 80% Hydrogel | 20% Fibroin |

TABLE 2

| Composition No. | Wt % Material A | Wt % Material B | Wt % Material C |
|---|---|---|---|
| 1 | 80% Hydrogel | 10% Chitosan | 10% Chitin |
| 2 | 80% Hydrogel | 10% Chitosan | 10% Fibroin |
| 3 | 80% Hydrogel | 10% Chitin | 10% Fibroin |

TABLE 3

| Composition No. | Wt % Material A | Wt % Material B | Wt % Material C |
|---|---|---|---|
| 1 | 70% Hydrogel | 15% Chitosan | 15% Chitin |
| 2 | 70% Hydrogel | 15% Chitosan | 15% Fibroin |
| 3 | 70% Hydrogel | 15% Chitin | 15% Fibroin |

TABLE 4

| Composition No. | Wt % Material A | Wt % Material B | Wt % Material C |
|---|---|---|---|
| 1 | 60% Hydrogel | 20% Chitosan | 20% Chitin |
| 2 | 60% Hydrogel | 20% Chitosan | 20% Fibroin |
| 3 | 60% Hydrogel | 20% Chitin | 20% Fibroin |

Figure 3B:
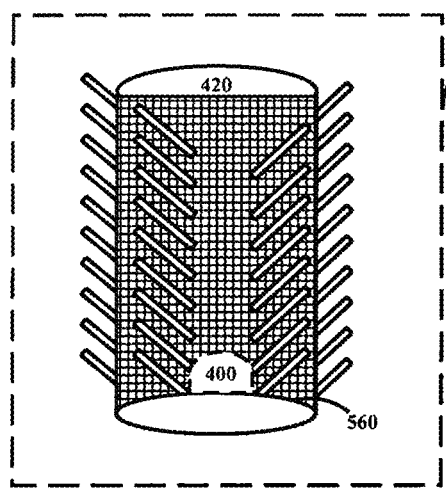
FIG. 3B illustrates the detachable bristles' section (as illustrated in FIG. 2C) with the removable/stretchable integrated mesh structured net (as illustrated in FIG. 3A) and the detachable cap (as illustrated in FIG. 2D).

FIG. 3B illustrates a detachable second section 580, which comprises/includes (a) the detachable cap 420 and (b) the detachable second section with bristles' 440 with the removable/stretchable integrated mesh structured net 560.

Figure 3C:
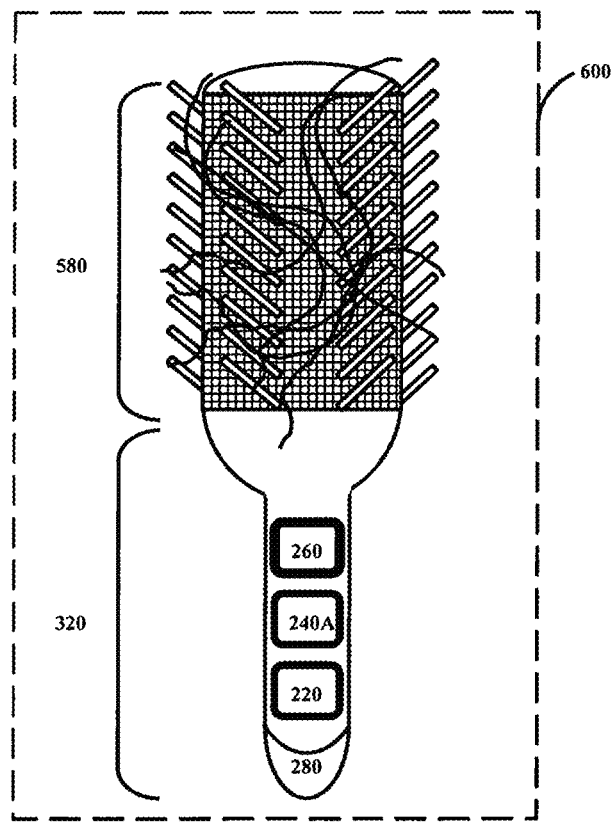
FIG. 3C illustrates another embodiment of a multifunctional hairbrush, which comprises/includes the detachable first section (as illustrated in FIG. 2B) and the detachable second section (as illustrated in FIG. 3B).

FIG. 3C illustrates a hairbrush 600, which comprises/includes (a) the detachable first section 320 and (b) the detachable second section 580. FIG. 3C also illustrates the loose hair, which can be trapped in the detachable second section 580.

Figure 4A:
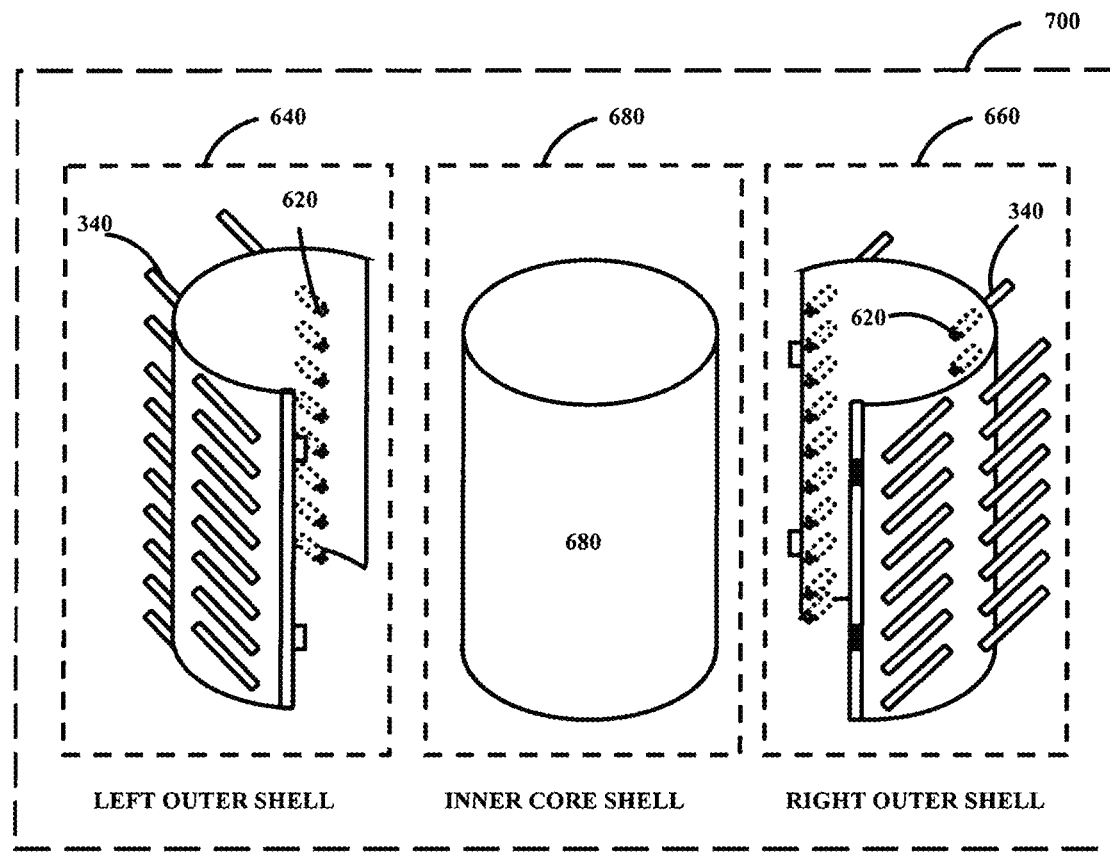
FIG. 4A illustrates another embodiment of a detachable bristles' section.

FIG. 4A illustrates a detachable section 700 which comprises/includes (a) a left outer shell 640, (b) a right outer shell 660 and (c) an inner core shell 680. Both the left outer shell 640 and right outer shell 660 have bristles, wherein each bristle is indicated by 340. Furthermore, end of each bristle has a miniature magnet 620 for intimate attachment to the inner core shell 680. An ultrasound wave generator/vibrator can be connected to the left outer shell 640 and/or the right outer shell 660—thus enabling the detachable section 700 to vibrate.

Figure 4B:
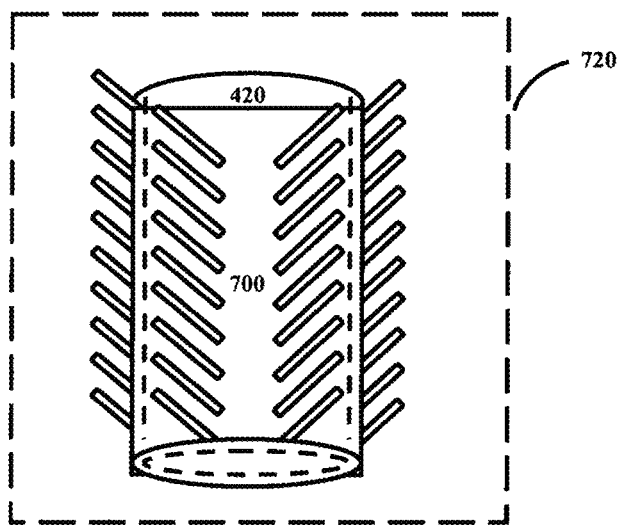
FIG. 4B illustrates a detachable second section, which comprises/includes the detachable cap (as illustrated in FIG. 2D) and the detachable bristles' section (as illustrated in FIG. 4A).

FIG. 4B illustrates a detachable second section 720, which comprises/includes (a) the detachable cap 420 and (b) the detachable section 700.

Figure 4C:
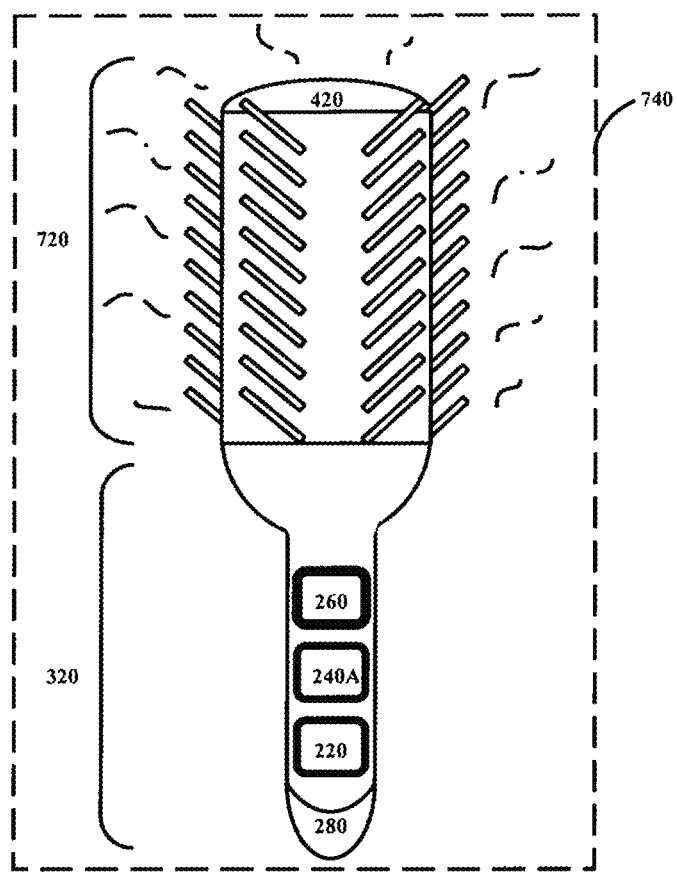
FIG. 4C illustrates another embodiment of a multifunctional hairbrush, which comprises/includes the detachable first section (as illustrated in FIG. 2B) and the detachable second section (as illustrated in FIG. 4B).

FIG. 4C illustrates a hairbrush 740, which comprises/includes (a) the detachable first section 320 and the detachable second section 720.

Figure 5A:
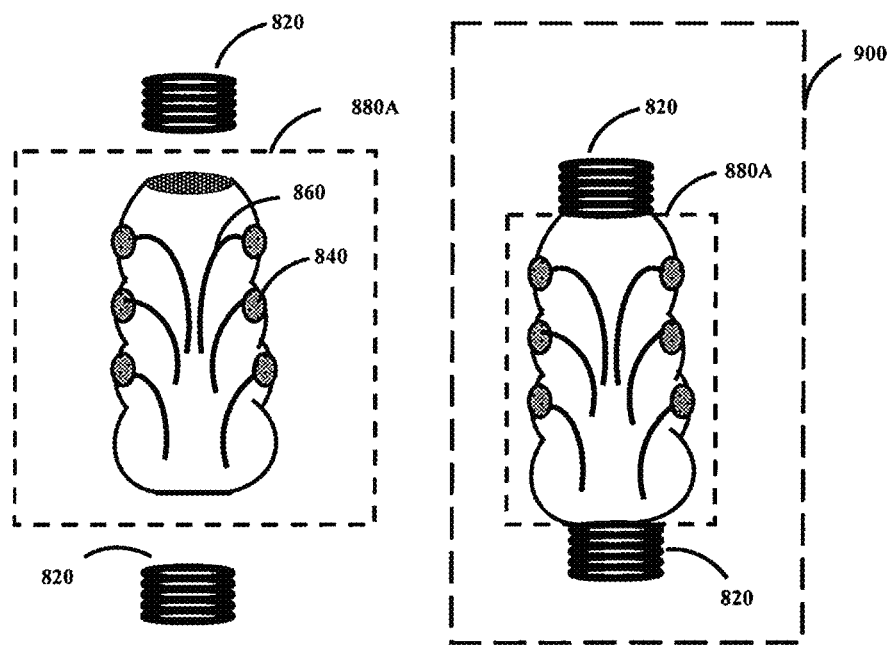
FIG. 5A illustrates a detachable container for a bioactive compound/biologically active molecule (including a regulatory protein/growth factor) or a mixture of bioactive compounds/biologically active molecules (including regulatory proteins/growth factors) for growth and protection of hair in a liquid or another pretreatment liquid (e.g., water).

FIG. 5A illustrates a detachable container 900 which comprises/includes two metallic spring contacts 820 and an inner structure 880A. The inner structure 880A has release holes, wherein each release hole is 840 and capillaries, wherein each capillary is 860. The metallic spring compresses to release a bioactive compound/botanical compound/biologically active molecule (including a regulatory protein/growth factor) or a mixture of bioactive compounds/botanical compounds/biologically active molecules (including regulatory proteins/growth factors) 540A in a liquid for growth and protection of hair through the release holes 840.

The above bioactive compound/botanical compound/biologically active molecule (including a regulatory protein/growth factor) or the mixture of bioactive compounds/botanical compounds/biologically active molecules (including regulatory proteins/growth factors) 540A can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

Figure 5B:
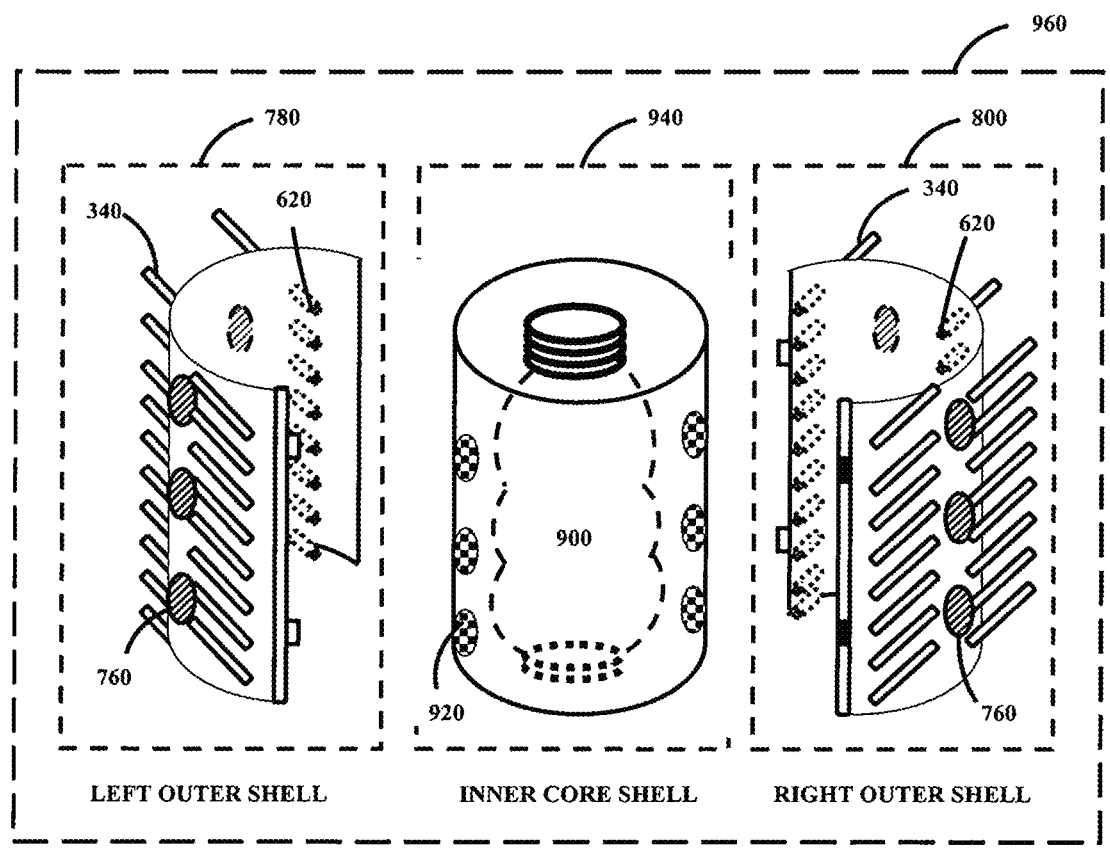
FIG. 5B illustrates a detachable bristles' section with a detachable spray applicator.

FIG. 5B illustrates a detachable second section (a detachable spray applicator and a detachable vibrator integrated with bristles) 960. The detachable spray applicator within the detachable section 960 can contain a bioactive compound/biologically active molecule (including a regulatory protein/growth factor) or a mixture of bioactive compounds/biologically active molecules (including regulatory proteins/growth factors) 540A in a liquid for growth and protection of hair to spray a bioactive compound/botanical compound/biologically active molecule (including a regulatory protein/growth factor) or a mixture of bioactive compounds/botanical compounds/biologically active molecules (including regulatory proteins/growth factors) 540A in a liquid for growth and protection of hair.

The above bioactive compound/botanical compound/biologically active molecule (including a regulatory protein/growth factor) or the mixture of bioactive compounds/botanical compounds/biologically active molecules (including regulatory proteins/growth factors) 540A can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in form of an emulsion/microemulsion/nanoemulsion.

The detachable section (the detachable spray applicator and the detachable vibrator integrated with bristles) 960 comprises/includes (a) a left outer shell 780, (b) a right outer shell 800 and (c) an inner core shell 940.

Both the left outer shell 780 and right outer shell 800 comprises/includes bristles, wherein each bristle is 340. Furthermore, end of each bristle comprises/includes a miniature magnet 620 for intimate attachment to the inner core shell 940. Both the left outer shell 780 and right outer shell 800 comprises/includes second release holes, wherein each second release hole is indicated by 760. The inner core shell 940 has the detachable container 900 with another type of first release holes, wherein each first release hole is indicated by 920. It should be noted the first release hole 920 is approximately aligned with the second release hole 760. An ultrasound wave generator/vibrator can be connected to the left outer shell 780 and/or the right outer shell 800—thus enabling the detachable section 960 to vibrate.

The detachable section (the detachable spray applicator and the detachable vibrator integrated with bristles) 960 comprises/includes the ultrasonic wave generator/vibrator, wherein the detachable spray applicator is activated or set in motion by the ultrasonic wave generator/vibrator.

The ultrasound wave generator/vibrator can cause pretreatment liquid molecules or the liquid molecules of a bioactive compound/botanical compound/biologically active molecule (including a regulatory protein/growth factor) or a mixture of bioactive compounds/botanical compounds/biologically active molecules (including regulatory proteins/growth factors) 540A to vibrate at an amplitude and frequency-thus generating microscopic/nano sized bubbles of the pretreatment liquid molecules or the said liquid molecules. These microscopic/nano sized bubbles can act like scrubbers for effective cleaning of scalp.

Figure 5C:
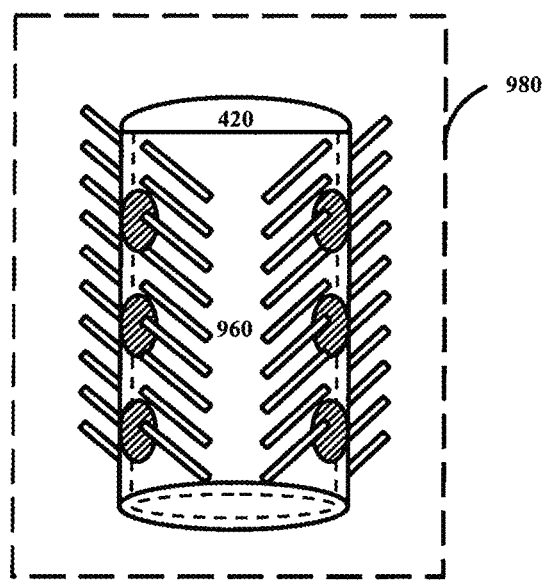
FIG. 5C illustrates the detachable bristles' section with the detachable spray applicator (as illustrated in FIG. 5B) and the detachable cap (as illustrated in FIG. 2D).

FIG. 5C illustrates a detachable second section 980, which comprises/includes (a) the detachable cap 420 and (b) the detachable second section (the detachable spray applicator and the detachable vibrator integrated with bristles) 960.

Figure 5D:
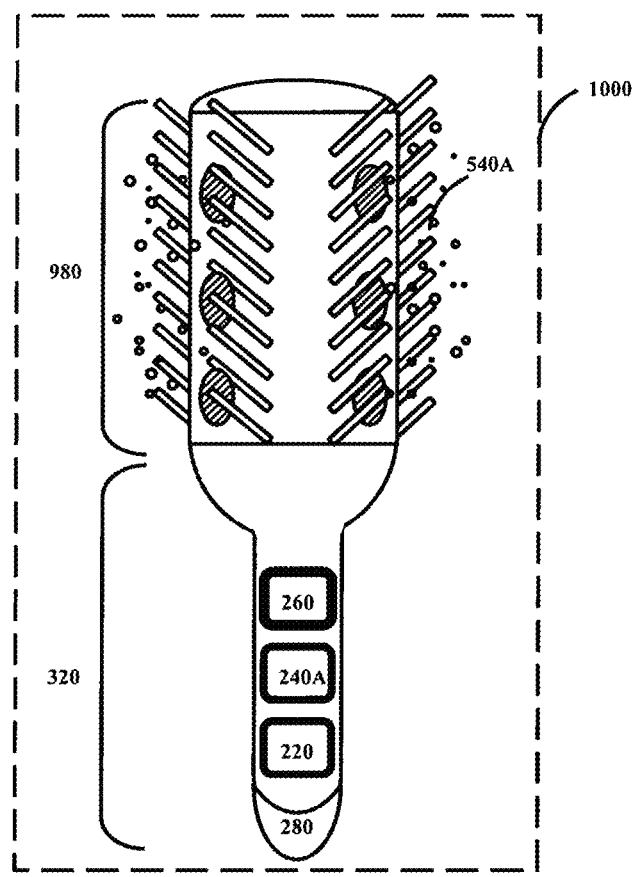
FIG. 5D illustrates another embodiment of a multifunctional hairbrush, which comprises/includes the detachable first section (as illustrated in FIG. 2B) and the detachable second section (as illustrated in FIG. 5C).

FIG. 5D illustrates a hairbrush 1000, which comprises/includes (a) the detachable first section 320 and (b) the detachable second section 980.

Figure 6A:
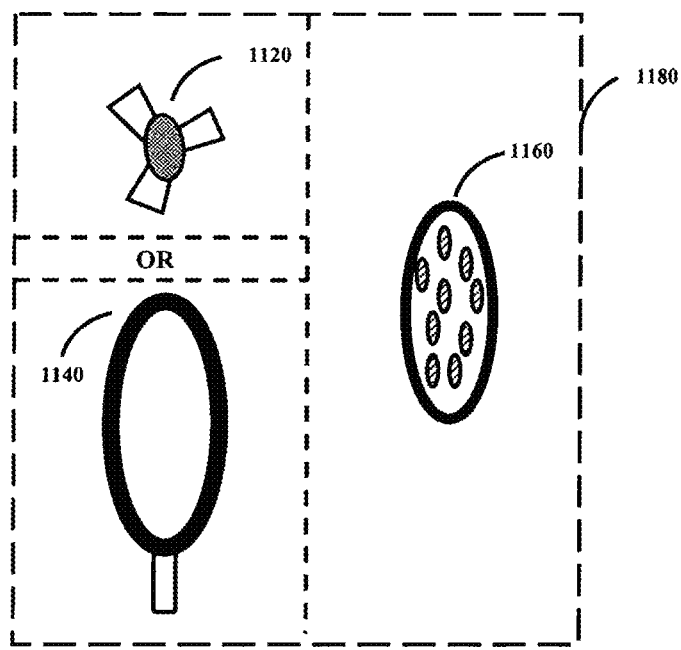
FIG. 6A illustrates a subsystem/unit of a hair dryer.

FIG. 6A illustrates a subsystem/unit 1180 which comprises/includes a blade fan 1120 or a bladeless fan 1140 and a heater 1160. A blade fan relies on blades to chop the air and push it forward, but a bladeless fan utilizes airflow dynamics. Air is pulled into the bladeless fan's cylindrical base, utilizing a small brushless motor. The motor's impeller pushes air into a hollow ring and air is then forced out slits, wherein the slits are located all around the hollow ring. The air is then accelerated into a circular motion. Additionally, the heater 1160 can be a resistive heater or an electromagnetic heater.

Figure 6B:
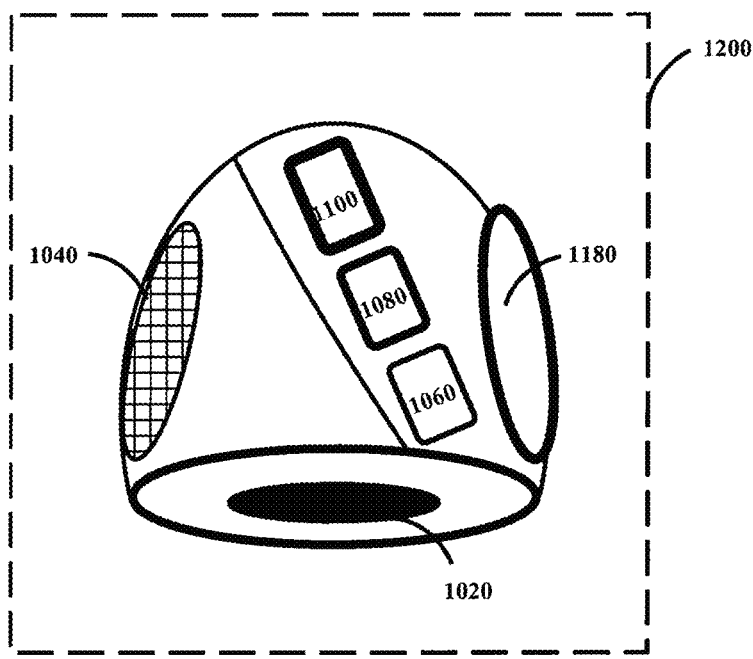
FIG. 6B illustrates an embodiment of a detachable (hair dryer) second section.

FIG. 6B illustrates a detachable (hair dryer) section 1200, which comprises/includes a metallic/magnetic contact area 1020, a removable air flow mesh 1040, a power (on/off) indicator 1060 (of the detachable hair dryer 1200), a moderate airflow indicator 1080 and a high airflow indicator 1100 and the unit 1180 (as illustrated in FIG. 6A).

Figure 6C:
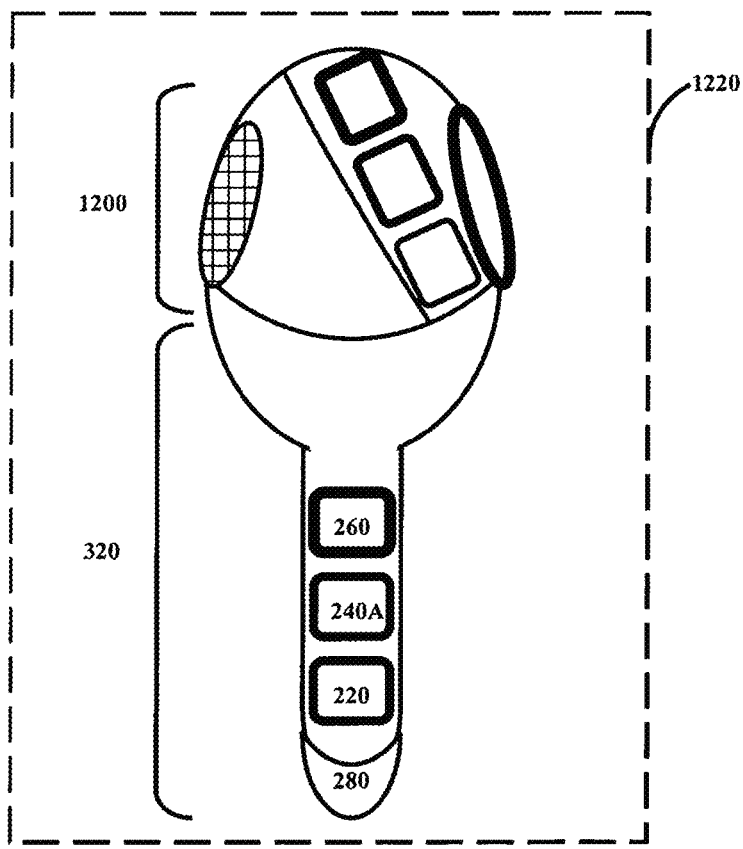
FIG. 6C illustrates another embodiment of a multifunctional hairbrush, which comprises/includes the detachable first section (as illustrated in FIG. 2B) and the detachable (hair dryer) second section (as illustrated in FIG. 6B).

FIG. 6C illustrates a hairbrush 1220, which comprises/includes (a) the detachable first section 320 and (b) the detachable (hair dryer) section 1200.

Figure 7A:
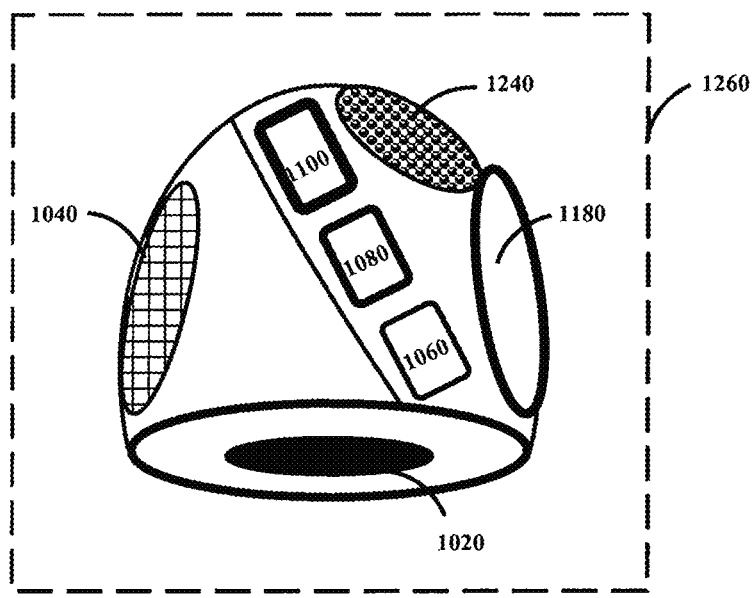
FIG. 7A illustrates another embodiment of a detachable (hair dryer) second section which comprises/includes a detachable low intensity light module with the detachable hair dryer (as illustrated in FIG. 6B).

FIG. 7A illustrates a detachable section 1260, which is similar to the detachable (hair dryer) 1200 (as illustrated in FIG. 6B) with an addition of a detachable low intensity light module 1240. The detachable low intensity light module 1240 can have just one light source (e.g., a light emitting diode/surface emitting laser) or many light sources in suitable (multiple) wavelength ranges. An electronic subsystem (for the detachable low intensity light module 1240) 1360C is not shown in FIG. 7A.

The detachable low intensity light module 1240 can provide an optical dose in the range from 0.5 $J/cm^2$ to 10 $J/cm^2$ in 600-700 nm wavelength range or an optical dose in the range from 0.5 $J/cm^2$ to 50 $J/cm^2$ in 700-2000 nm wavelength range, or a combination of an optical dose in the range from 0.5 $J/cm^2$ to 10 $J/cm^2$ in 600-700 nm wavelength range and an optical dose in the range from 0.5 $J/cm^2$ to 50 $J/cm^2$ in 700-2000 nm wavelength range for synergistic effects. Wavelengths in the 600-700 nm (red) range are for shallow penetration of light/laser beam and wavelengths in the 700-2000 nm (near-infrared) are for deeper penetration of light/laser beam. Wavelengths in the 700-770 nm may not have much photoactivity. Additionally, the detachable low intensity light module 1240 can provide constant/pulse intensity of light, lower pulse rate (e.g., 2 Hz, as opposed to 10 Hz) and polarized light.

The detachable low intensity light module 1240 can activate/induce/photoactivate a minute quantity of (a) chemically reactive oxygen molecules and/or (b) chemically reactive bioactive compound/botanical compound/biologically active molecule (including a regulatory protein/growth factor) or the mixture of bioactive compounds/botanical compounds/biologically active molecules (including regulatory proteins/growth factors) 540A (for growth and protection of hair)/540B (for rejuvenation and protection of skin) to beneficially stimulate certain beneficial cellular functions for growth and protection of hair—even in other healthcare applications such as arthritis (inflammation) reduction, rejuvenation and protection of skin and wound care. The above bioactive compound/botanical compound/biologically active molecule (including a regulatory protein/growth factor) or the mixture of bioactive compounds/botanical compounds/biologically active molecules (including regulatory proteins/growth factors) 540/540B can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

Figure 7B:
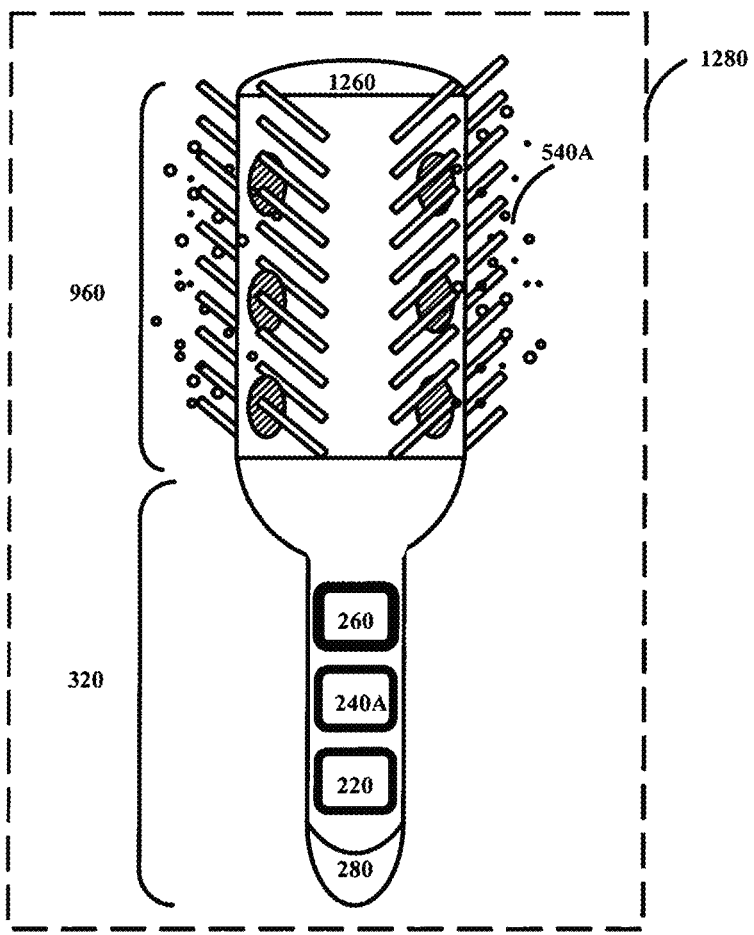
FIG. 7B illustrates another embodiment of a multifunctional hairbrush, which comprises/includes the detachable first section (as illustrated in FIG. 2B) and the detachable (hair dryer) second section (as illustrated in FIG. 7A).

FIG. 7B illustrates a hairbrush 1280, which comprises/includes (a) a detachable first section 320, (b) the detachable second section 960 and (c) the detachable section 1260.

Figure 8A:
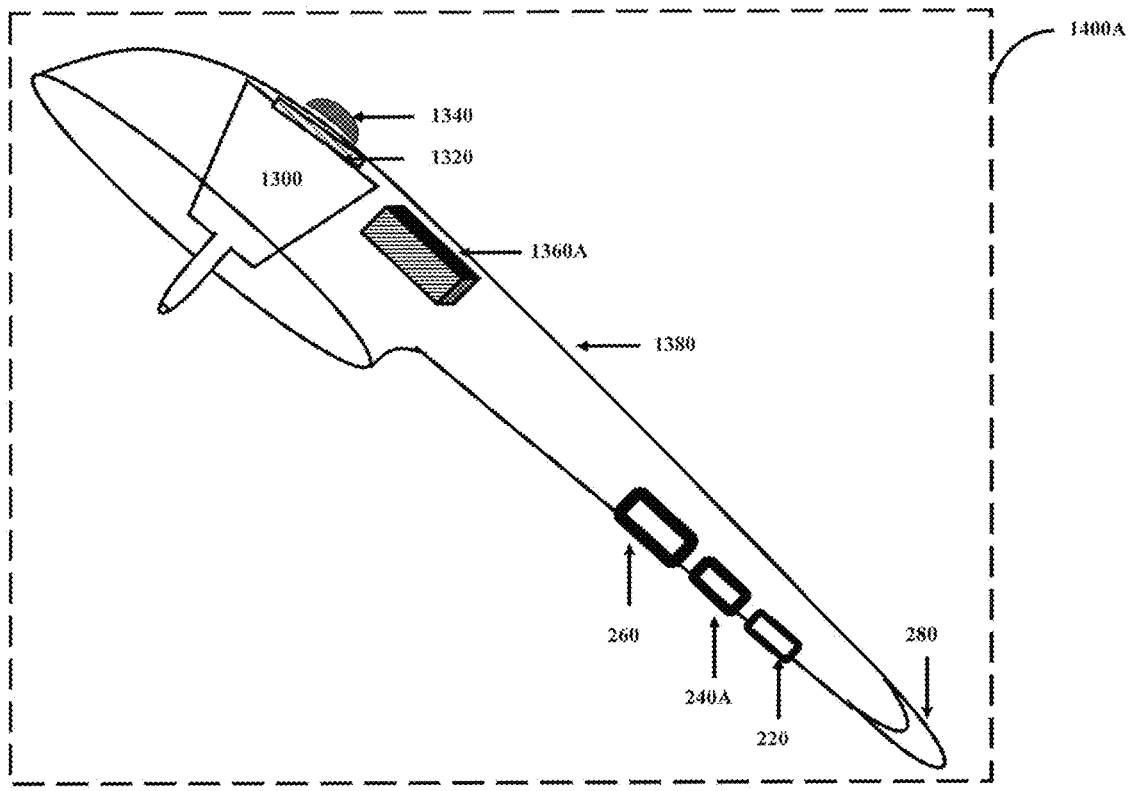
FIG. 8A illustrates a mechanical assembly of a detachable spray applicator (based on an ultrasonic wave generator/vibrator).

FIG. 8A illustrates a mechanical assembly 1400A, which comprises/includes (a) a detachable spray applicator (comprising/including the ultrasonic wave generator/vibrator) 1300, (b) a connector (for the detachable spray applicator 1300) 1320, (c) a push button (for the detachable spray applicator 1300) 1340, (d) an electronic subsystem (for the detachable spray applicator 1300) 1360A and (e) a mechanical structure 1380. The other components are (a) the power indicator 220, (b) the vibration (due to the ultrasonic wave generator/vibrator) intensity indicator 240A, (c) the spray indicator 260 and (d) the bottom electrical contact area 280.

The detachable spray applicator 1300 comprises/includes the ultrasonic wave generator or a vibrator, wherein the spray applicator 1300 is activated or set in motion by the ultrasonic wave generator or the vibrator.

Figure 8B:
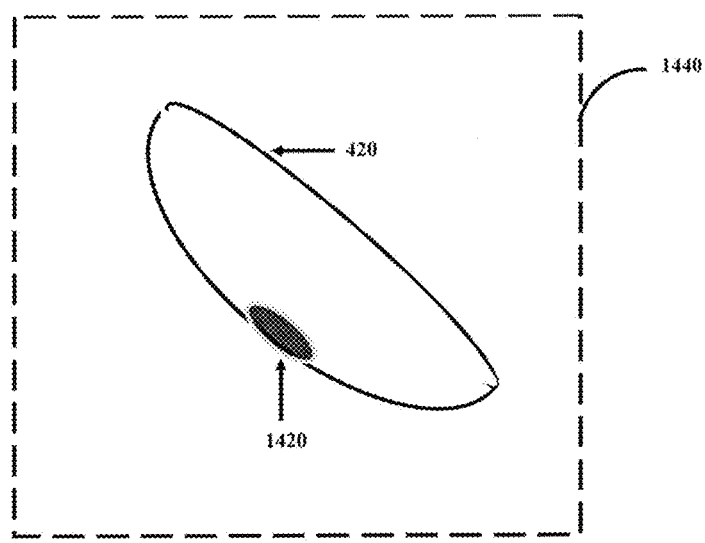
FIG. 8B illustrates a detachable cap assembly with a hole close to the center of the detachable cap assembly.

FIG. 8B illustrates a detachable cap assembly 1440, which comprises/includes the detachable cap 420 with a hole 1420 close to the center of the frame of the detachable cap assembly.

Figure 8C:
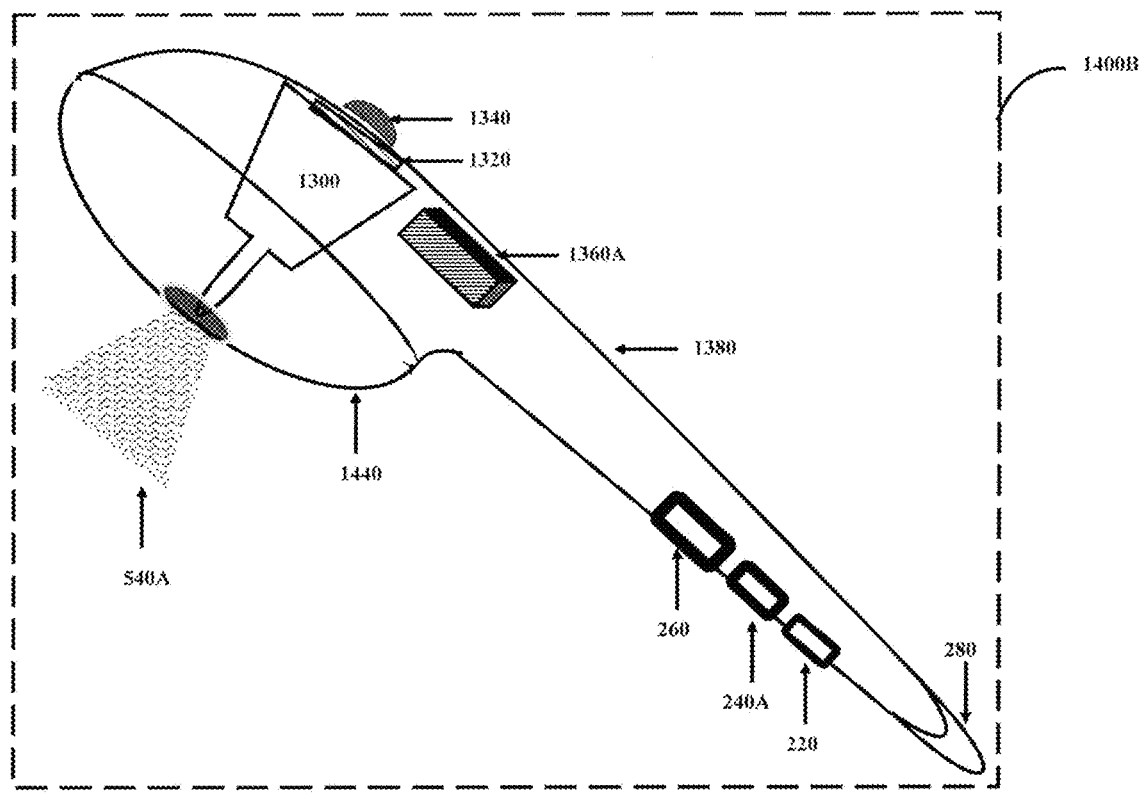
FIG. 8C illustrates an embodiment of a complete mechanical assembly of the detachable spray applicator (based on the ultrasonic wave generator/vibrator) and the detachable cap assembly.

FIG. 8C illustrates a complete mechanical assembly 1400B, which comprises/includes (a) the detachable cap assembly 1440 (as illustrated in FIG. 8B) and (b) the mechanical assembly 1440A (as illustrated in FIG. 8A).

Figure 9A:
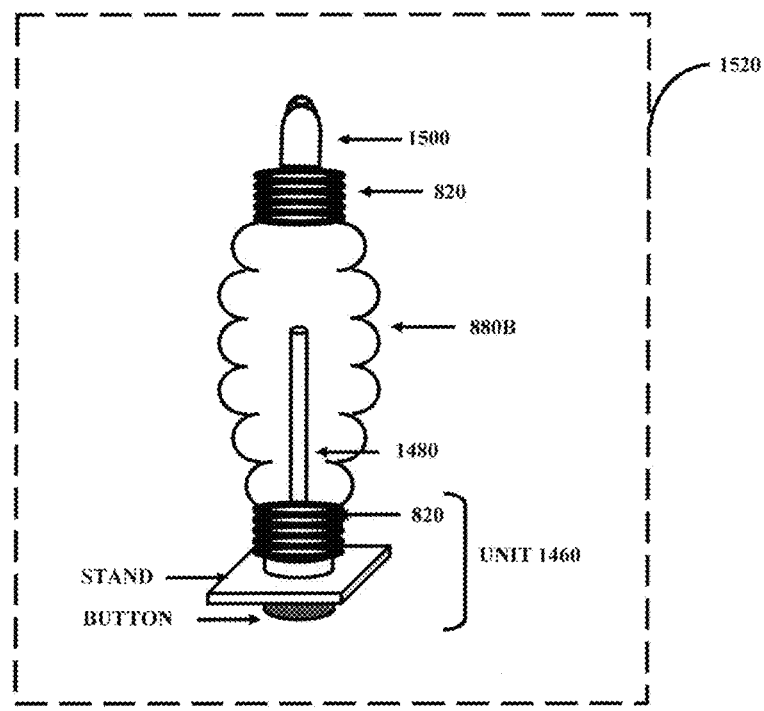
FIG. 9A illustrates an embodiment of a detachable spray applicator (based on a nozzle).

FIG. 9A illustrates another embodiment of a detachable spray applicator (comprising/including a nozzle) 1520, which comprises/includes (a) the top metallic spring contact 820, (b) a flexible liquid container 880B, (c) a unit (for the detachable spray applicator 1520) 1460 and (d) a nozzle 1480. The unit (for the detachable spray applicator 1520) 1460 comprises/includes (a) the bottom metallic spring contact 820, (b) a support structure (which is not labeled, but shown in FIG. 9A) and (c) a button (which is not labeled, but shown in FIG. 9A).

Figure 9B:
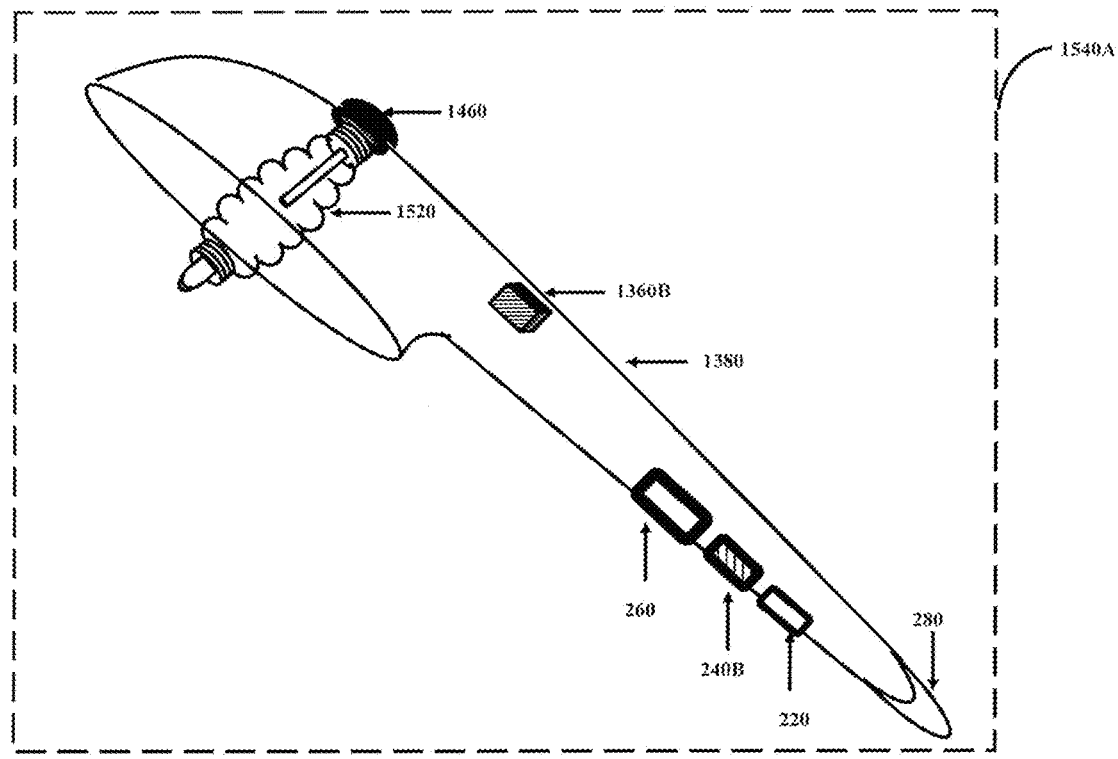
FIG. 9B illustrates a mechanical assembly of the detachable spray applicator (based on the nozzle).

FIG. 9B illustrates a mechanical assembly 1540A, which comprises/includes (a) an electronic subsystem (for the detachable spray applicator 1520) 1360B, (b) the mechanical structure 1380, (c) the unit (for the detachable spray applicator 1520) 1460 and (d) another detachable spray applicator (comprising/including the nozzle) 1520. The other components are (a) the power indicator 220, (b) the vibration (due to the nozzle) intensity indicator 240B, (c) the spray indicator 260 and (d) the bottom electrical contact area 280.

The detachable spray applicator 1520 comprises/includes the nozzle, wherein the detachable spray applicator 1520 is activated or set in motion by the nozzle.

Figure 9C:
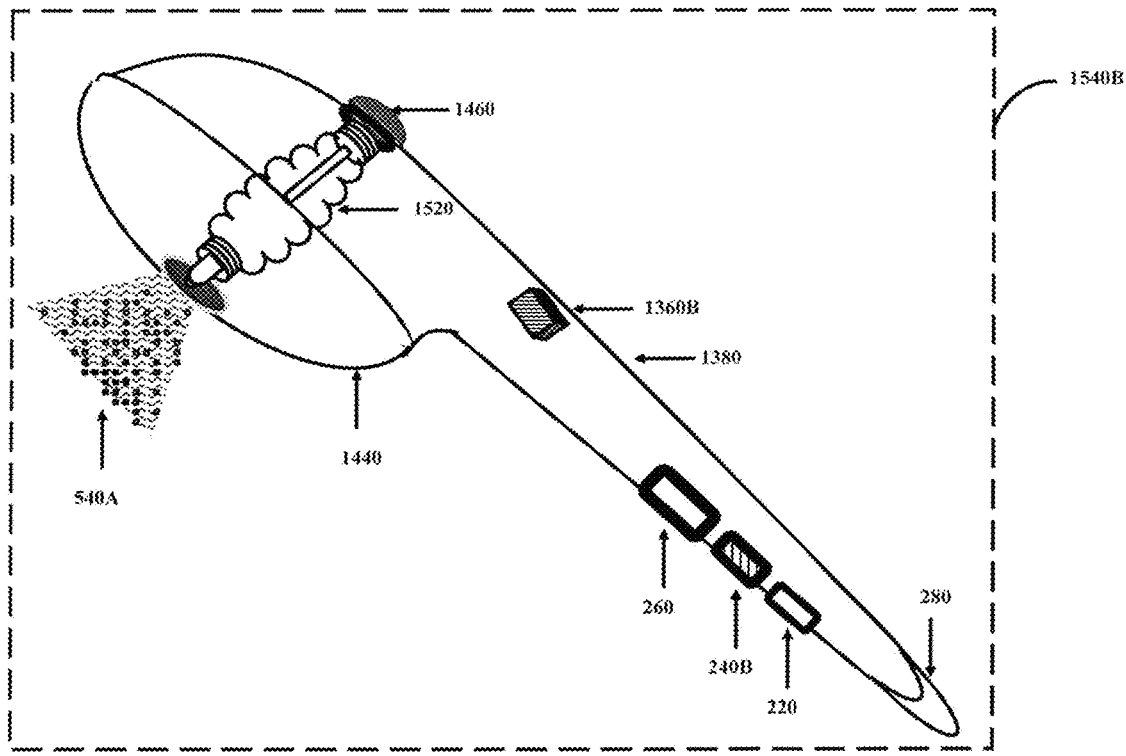
FIG. 9C illustrates another embodiment of a complete mechanical assembly of the detachable spray applicator (based on the nozzle) and the detachable cap assembly.

FIG. 9C illustrates a complete mechanical assembly 1540B, which comprises/includes (a) the detachable cap assembly 1440 (as illustrated in FIG. 8B) and (b) the mechanical assembly 1540A (as illustrated in FIG. 9B).

The detachable spray applicator (comprising/including the ultrasonic wave generator/vibrator) 1300 or the detachable spray applicator (comprising/including the nozzle) 1520 can cause pretreatment liquid molecules or liquid molecules of a bioactive compound/botanical compound/biologically active molecule (including a regulatory protein/growth factor) or a mixture of bioactive compounds/botanical compounds/biologically active molecules (including regulatory proteins/growth factors) 540A to vibrate at an amplitude and frequency-thus generating bubbles of the pretreatment liquid molecules or the said liquid molecules. These bubbles can act like scrubbers for effective cleaning of scalp.

The above bioactive compound/botanical compound/biologically active molecule (including a regulatory protein/growth factor) or the mixture of bioactive compounds/botanical compounds/biologically active molecules (including regulatory proteins/growth factors) 540A can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

FIG. 10A illustrates a mechanical assembly 1560A, which comprises/includes (a) the detachable low intensity light module 1240, (b) the detachable spray applicator (comprising/including the ultrasonic wave generator/vibrator) 1300, (c) the push button (for the detachable spray applicator 1300) 1340, (d) the electronic subsystem (for the detachable spray applicator 1300) 1360A, (e) the electronic subsystem (for the detachable low intensity light module 1240) 1360C and (f) the mechanical structure 1380. The other components are (a) the power indicator 220, (b) a light module indicator (for the detachable low intensity light module 1240) 220A, (c) the vibration (due to the ultrasonic wave generator/vibrator) intensity indicator 240A, (d) the spray indicator 260 and (f) the bottom electrical contact area 280.

The connector (for the detachable spray applicator 1300) 1320 is not shown due to the shadowing of the detachable low intensity light module 1240.

FIG. 10B illustrates a front view of a complete mechanical assembly 1560B, which comprises/includes (a) the detachable cap assembly 1440 (as illustrated in FIG. 8B) and (b) the mechanical assembly 1560A (as illustrated in FIG. 10A).

FIG. 10C illustrates a back view 1560C of the complete mechanical assembly 1560B (as illustrated in FIG. 10B). FIG. 10C illustrates (a) the bottom electrical contact area 280, (b) the detachable low intensity light module 1240, (c) the mechanical structure 1380 and (d) the push button (for the detachable spray applicator 1300) 1340.

FIG. 11A illustrates a mechanical assembly 1580A, which comprises/includes (a) the detachable low intensity light module 1240, (b) the electronic subsystem (for the detachable spray applicator 1520) 1360B, (c) the electronic subsystem (for the detachable low intensity light module 1240)

1360C, (d) the mechanical structure 1380, (e) the unit (for the detachable spray applicator 1520) 1460 and (f) the detachable spray applicator (comprising/including the nozzle) 1520. The other components are (a) the power indicator 220, (b) the light module indicator (for the detachable low intensity light module 1240) 220A, (c) the vibration (due to the nozzle) intensity indicator 240B, (d) the spray indicator 260 and (e) the bottom electrical contact area 280.

FIG. 11B illustrates a front view of a complete mechanical assembly 1580B, which comprises/includes (a) the detachable cap assembly 1440 (as illustrated in FIG. 8B) and (b) the mechanical assembly 1580A (as illustrated in FIG. 11A).

FIG. 11C illustrates a back view 1580C of the complete mechanical assembly 1580B (as illustrated in FIG. 11B). FIG. 11C illustrates (a) the bottom electrical contact area 280, (b) the detachable low intensity light module 1240, (c) the mechanical structure 1380 and (d) the unit (for the detachable spray applicator 1520) 1460.

Figure 12:
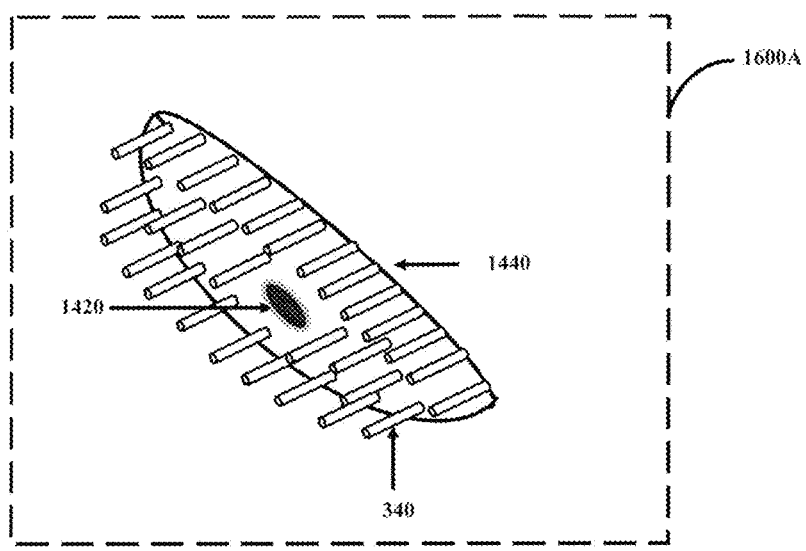
FIG. 12 illustrates an embodiment of a detachable hairbrush unit.

FIG. 12 illustrates a detachable hairbrush unit 1660A, which comprises/includes (a) the bristle 340 and (b) a hairbrush unit frame 1440. The detachable hairbrush unit 1660A has a hole 1420 close to the center of the frame of the detachable hairbrush unit 1660A.

Figure 13A:
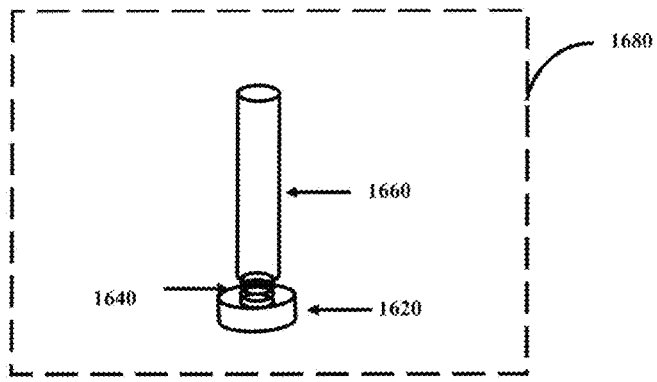
FIG. 13A illustrates another type of bristle, which can enable motion (including clockwise motion/counter clockwise motion/circular motion)/vibration.

FIG. 13A illustrates another type of bristle 1680, which comprises/includes (a) a base 1620, (b) a miniature mechanical spring 1640 for motion (including clockwise motion/counter clockwise motion/circular motion)/vibration and (c) a bristle strand 1660. An electronic subsystem for motion/vibration (utilizing the ultrasonic wave generator or vibrator) can be connected with a general purpose electronic subsystem of a particular embodiment of a device/apparatus. The bristle 1680 can enable motion/vibration (including clockwise motion/counter clockwise motion/circular motion) for massaging hair/scalp.

By way of an example and not by way of any limitation, the base 1620 can comprise/include multiple bristle strands 1660s.

By way of an example and not by way of any limitation, the material for the bristle strands 1660s can be a biocompatible material/biocomposite material/nylon.

Figure 13B:
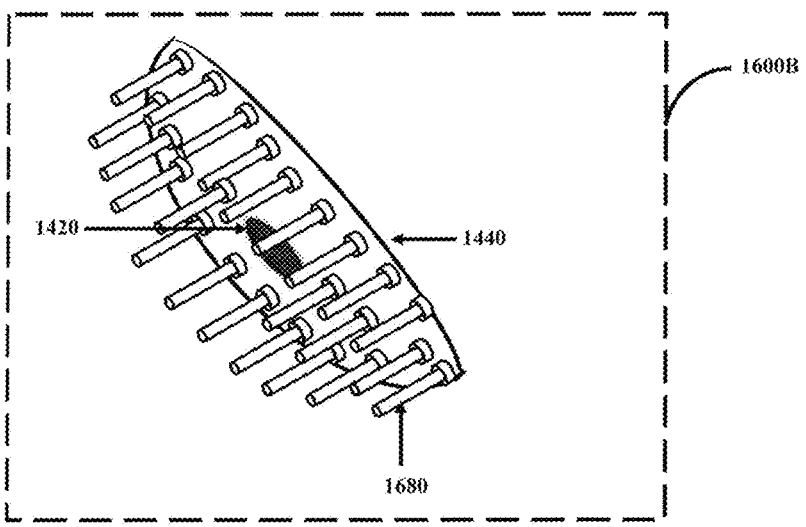
FIG. 13B illustrates another embodiment of a detachable hairbrush unit, utilizing bristles (as illustrated in FIG. 13A).

FIG. 13B illustrates another detachable hairbrush unit 1600B, which comprises/includes (a) the detachable hairbrush unit frame 1440 and (b) the bristle 1680. The detachable hairbrush unit 1660B has a hole 1420 close to the center of the frame of the detachable hairbrush unit 1660B.

Figure 14A:
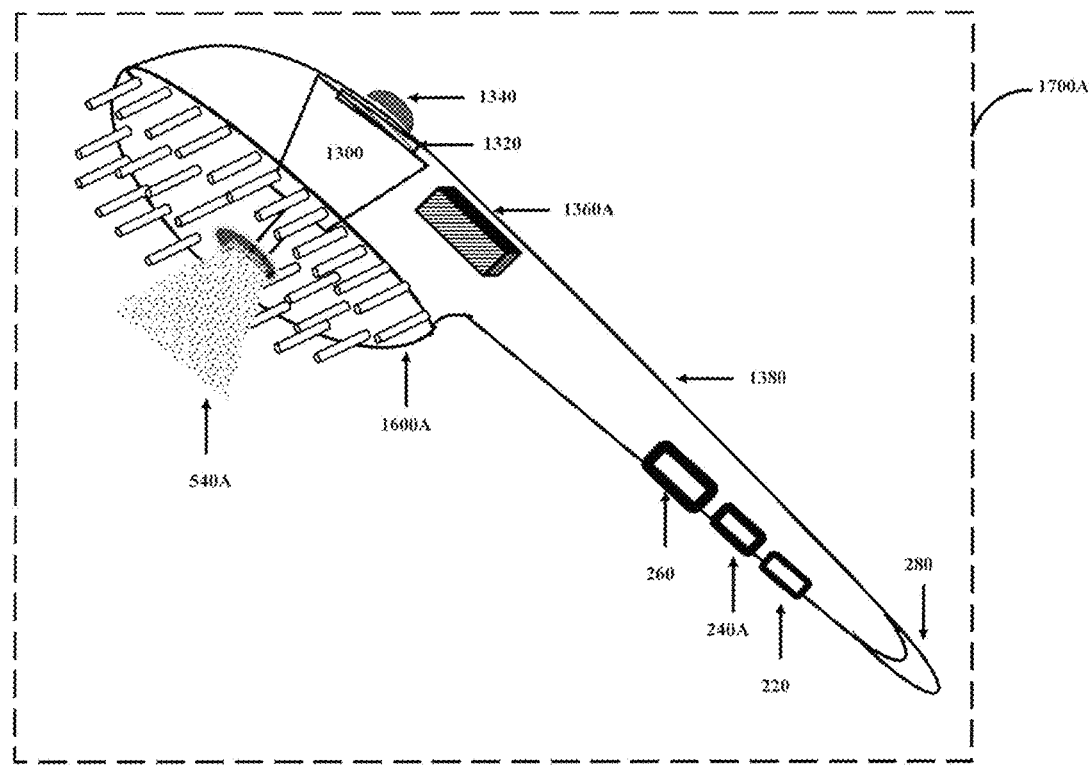
FIG. 14A illustrates an embodiment of a complete mechanical assembly with the detachable spray applicator (based on the ultrasonic wave generator/vibrator) and the detachable hairbrush unit (as illustrated in FIG. 12).

FIG. 14A illustrates a complete mechanical assembly 1700A, which comprises/includes (a) the detachable spray applicator (comprising/including the ultrasonic wave generator/vibrator) 1300, (b) the connector (for the detachable spray applicator 1300) 1320, (c) the push button (for the detachable spray applicator 1300) 1340, (d) the electronic subsystem (for the detachable spray applicator 1300) 1360A, (e) the mechanical structure 1380 and (f) the detachable hairbrush unit 1600A. The other components are (a) the power indicator 220, (b) the vibration (due to the ultrasonic wave generator/vibrator) intensity indicator 240A, (c) the spray indicator 260 and (d) the bottom electrical contact area 280.

Figure 14B:
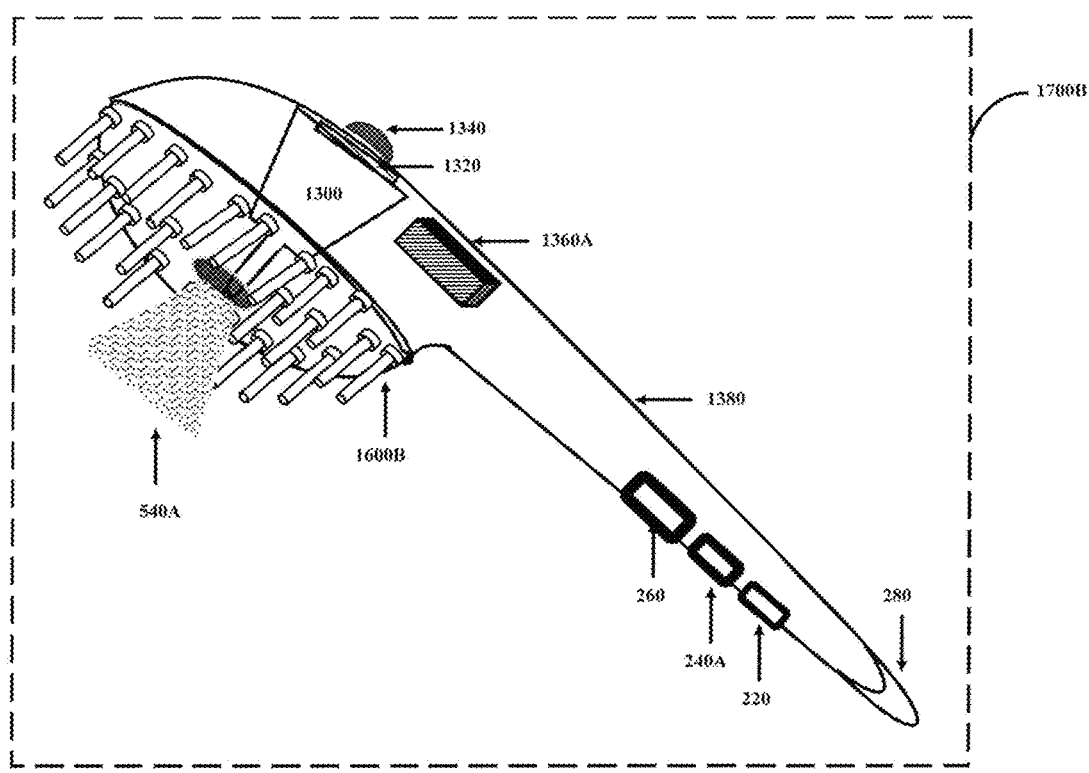
FIG. 14B illustrates another embodiment of a complete mechanical assembly with the detachable spray applicator (based on the ultrasonic wave generator/vibrator) and the detachable hairbrush unit (as illustrated in FIG. 13B).

FIG. 14B is similar to FIG. 14A, except the detachable hairbrush unit 1600A is replaced by the detachable hairbrush unit 1600B.

Figure 15A:
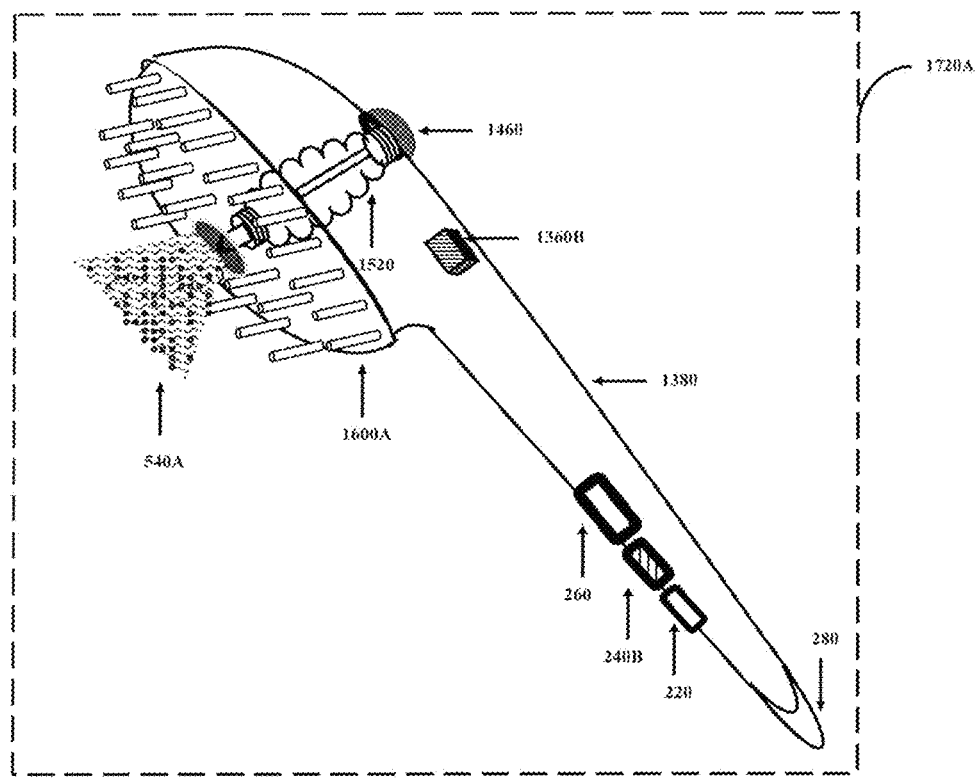
FIG. 15A illustrates an embodiment of a complete mechanical assembly with the detachable spray applicator (based on the nozzle) and the detachable hairbrush unit (as illustrated in FIG. 12).

FIG. 15A illustrates a complete mechanical assembly 1720A, which comprises/includes (a) the electronic subsystem (for the detachable spray applicator 1520) 1360B, (b) the mechanical structure 1380, (c) the unit (for the detachable spray applicator 1520) 1460, (d) the detachable spray applicator (comprising/including the nozzle) 1520 and (e) the detachable hairbrush unit 1600A. Other components are (a) the power indicator 220, (b) the vibration (due to the nozzle) intensity indicator 240B, (c) the spray indicator 260 and (d) the bottom electrical contact area 280.

Figure 15B:
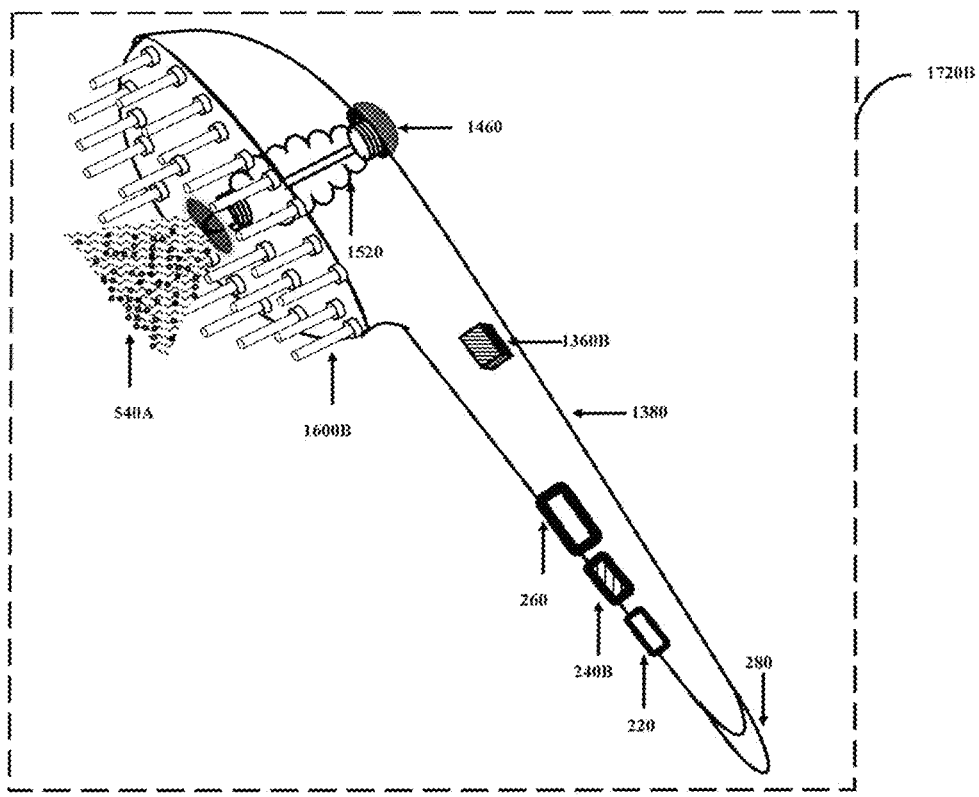
FIG. 15B illustrates another embodiment of a complete mechanical assembly with the detachable spray applicator (based on the nozzle) and the detachable hairbrush unit (as illustrated in FIG. 13B).

FIG. 15B is similar to FIG. 15A, except the detachable hairbrush unit 1600A is replaced by the detachable hairbrush unit 1600B.

Figure 16:
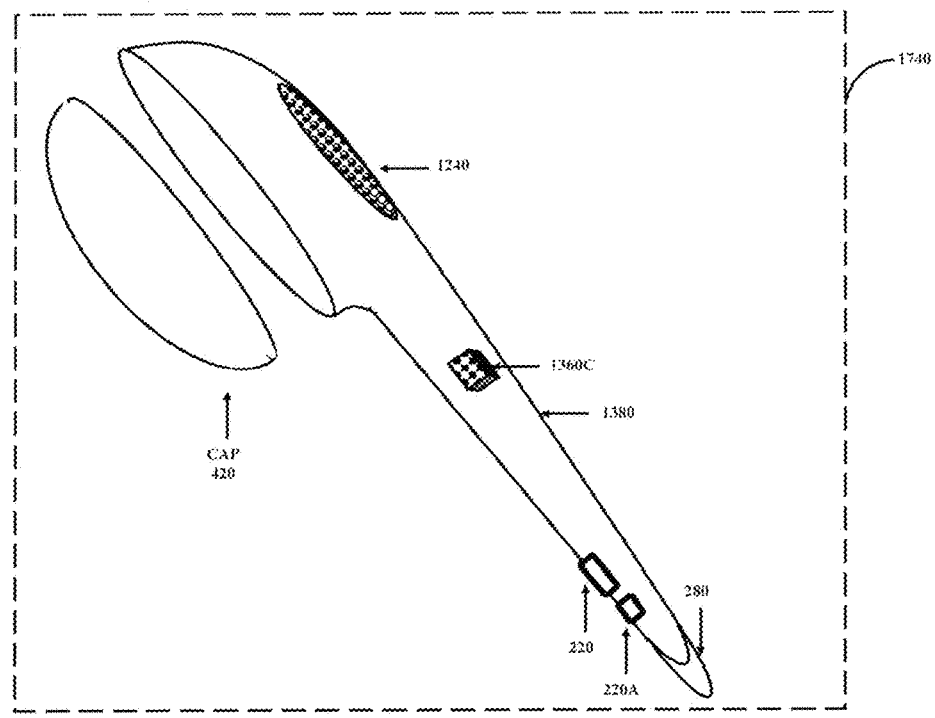
FIG. 16 illustrates an embodiment of a mechanical assembly with the detachable low intensity light module and the detachable cap.

FIG. 16 illustrates a mechanical assembly 1740, which comprises/includes (a) the detachable cap 420, (b) the detachable low intensity light module 1240, (c) the electronic subsystem (for the detachable low intensity light module 1240) 1360C and (d) the mechanical structure 1380. The other components are (a) the power indicator 220, (b) the light module indicator (for the detachable low intensity light module 1240) 220A and (c) the bottom electrical contact area 280.

Figures 17A, 17B:
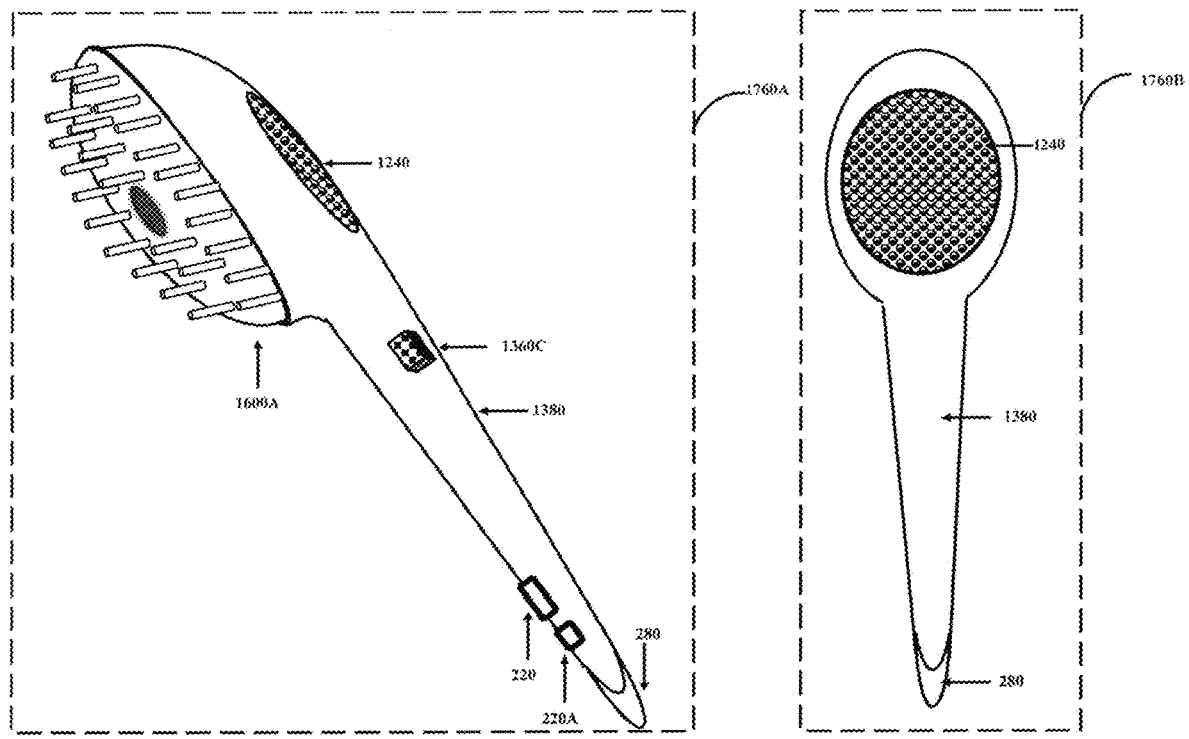
FIG. 17A illustrates an embodiment of a front view of a complete mechanical assembly with the detachable low intensity light module and the detachable hairbrush unit.
FIG. 17B illustrates a back view of the complete mechanical assembly (as illustrated in FIG. 17A).

FIG. 17A illustrates a front view of a complete mechanical assembly 1760A, which comprises/includes (a) the detachable low intensity light module 1240, (b) the electronic subsystem (for the detachable low intensity light module 1240) 1360C, (c) the mechanical structure 1380 and (d) the detachable hairbrush unit 1600A. The other components are (a) the power indicator 220, (b) the light module indicator (for the detachable low intensity light module 1240) 220A and (c) the bottom electrical contact area 280.

FIG. 17B illustrates a back view 1760B of the complete mechanical assembly 1760A (as illustrated in FIG. 17A). FIG. 17B comprises/includes (a) the bottom electrical contact area 280, (b) the detachable low intensity light module 1240 and (c) the mechanical structure 1380.

FIG. 17C illustrates a complete mechanical assembly 1760C, which comprises/includes the complete mechanical assembly (a) the removable/stretchable integrated mesh structured net 560 and (b) the complete mechanical assembly 1760A (as illustrated in FIG. 17A).

FIG. 18A illustrates a front view of a complete mechanical assembly 1780A, which comprises/includes (a) the detachable low intensity light module 1240, (b) the electronic subsystem (for the detachable low intensity light module 1240) 1360C, (c) the mechanical structure 1380 and (d) the detachable hairbrush unit 1600B. The other components are (a) the power indicator 220, (b) the light module indicator (for the detachable low intensity light module 1240) 220A and (c) the bottom electrical contact area 280.

FIG. 18B illustrates a back view 1780B of the complete mechanical assembly 1780A (as illustrated in FIG. 18A). FIG. 18B comprises/includes (a) the bottom electrical contact area 280, (b) the detachable low intensity light module 1240 and (c) the mechanical structure 1380.

FIG. 18C illustrates a complete mechanical assembly 1780C, which comprises/includes (a) the removable/stretchable integrated mesh structured net 560 and (b) the complete mechanical assembly 1780A (as illustrated in FIG. 18A).

FIG. 19A illustrates a front view of a complete mechanical assembly 1800A, which comprises/includes (a) the detachable low intensity light module 1240, (b) the detachable spray applicator (comprising/including the ultrasonic wave generator/vibrator) 1300, (c) the push button (for the detachable spray applicator 1300) 1340, (d) the electronic subsystem (for the detachable spray applicator 1300) 1360A, (e) the electronic subsystem (for the detachable low intensity light module 1240) 1360C, (f) the mechanical structure 1380 and (g) the detachable hairbrush unit 1600A. The other components are (a) the power indicator 220, (b) the light module indicator (for the detachable low intensity light module 1240) 220A, (c) the vibration (due to the ultrasonic wave generator/vibrator) intensity indicator 240A, (d) the spray indicator 260 and (e) the bottom electrical contact area 280.

FIG. 19B illustrates a back view 1800B of the complete mechanical assembly 1800A (as illustrated in FIG. 19A). FIG. 19B comprises/includes (a) the bottom electrical contact area 280, (b) the detachable low intensity light module 1240, (c) the push button (for the detachable spray applicator 1300) 1340 and (d) the mechanical structure 1380.

Figure 20A:
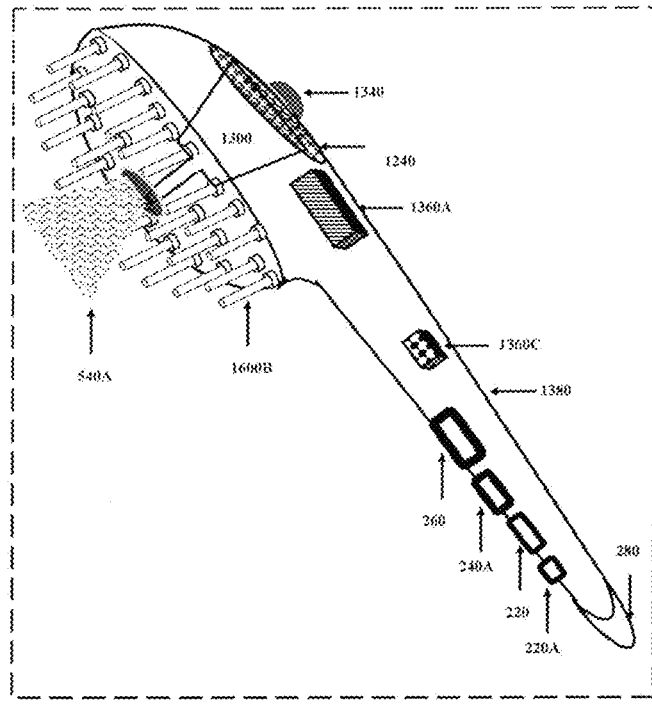
FIGS. 20A-20B are similar to FIGS. 19A-19B, wherein the particular detachable hairbrush unit (in FIGS. 19A-19B) is replaced by another type of detachable hairbrush unit.

FIG. 20A illustrates a front view of a complete mechanical assembly 1820A, which is similar to FIG. 19A, except the detachable hairbrush unit 1600A is replaced by the detachable hairbrush unit 1600B.

Figure 20B:
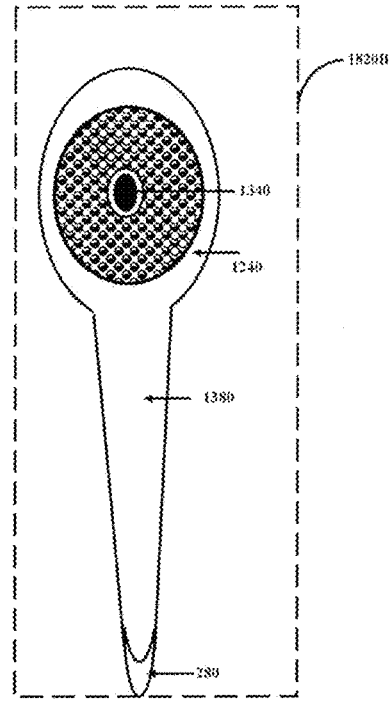

FIG. 20B illustrates a back view 1820B of the complete mechanical assembly 1820A (as illustrated in FIG. 20A). FIG. 20B comprises/includes are (a) the bottom electrical contact area 280, (b) the detachable low intensity light module 1240, (c) the push button (for the detachable spray applicator 1300) 1340 and (d) the mechanical structure 1380.

Figure 21A:
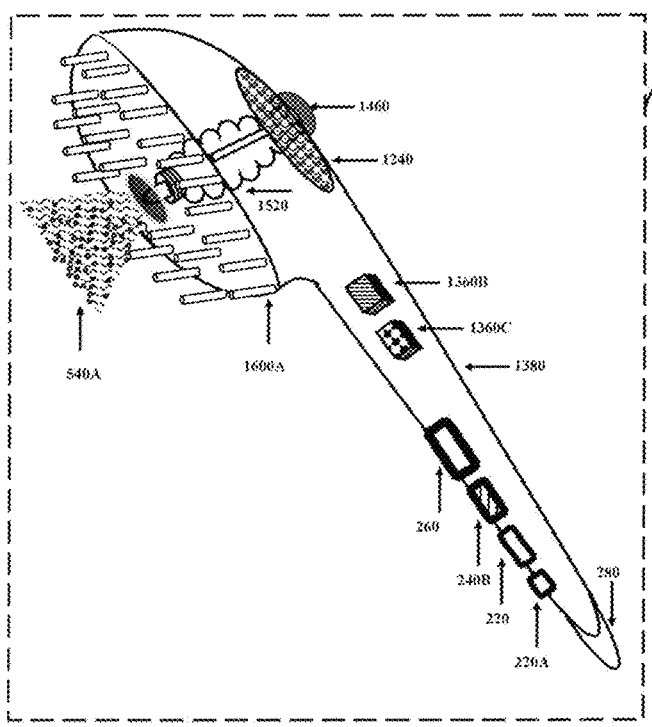
FIG. 21A illustrates an embodiment of a front view of a complete mechanical assembly with the detachable low intensity light module, the detachable spray applicator (based on the nozzle) and the detachable hairbrush unit.

FIG. 21A illustrates a front view of a complete mechanical assembly 1840A, which comprises/includes (a) the detachable low intensity light module 1240, (b) the electronic subsystem (for the detachable spray applicator 1520) 1360B, (c) the electronic subsystem (for the detachable low intensity light module 1240) 1360C, (d) the mechanical structure 1380, (e) the unit (for the detachable spray applicator 1520) 1460, (f) the detachable spray applicator (comprising/including the nozzle) 1520 and (g) the detachable hairbrush unit 1600A. The other components are (a) the power indicator 220, (b) the light module indicator (for the detachable low intensity light module 1240) 220A, (c) the vibration (due to the nozzle) intensity indicator 240B, (c) the spray indicator 260 and (d) the bottom electrical contact area 280.

Figure 21B:
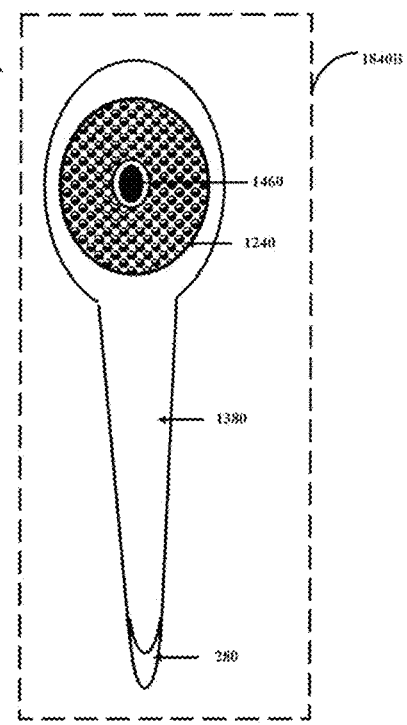
FIG. 21B illustrates a back view of the complete mechanical assembly (as illustrated in FIG. 21A).

FIG. 21B illustrates a back view 1840B of the complete mechanical assembly 1840A (as illustrated in Figure in 21A). FIG. 21B comprises/includes (a) the bottom electrical contact area 280, (b) the detachable low intensity light module 1240, (c) the mechanical structure 1380 and (d) the unit (for the detachable spray applicator 1520) 1460.

Figure 22A:
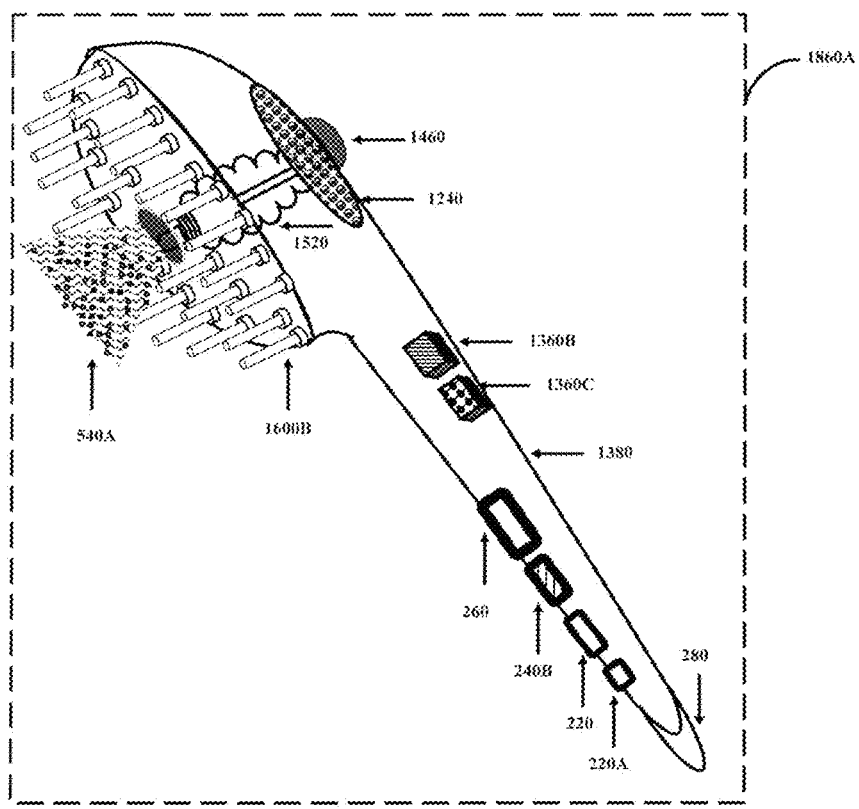
FIGS. 22A-22B are similar to FIGS. 21A-21B, wherein the particular detachable hairbrush unit (in FIGS. 21A-21B) is replaced by another type of detachable hairbrush unit.

FIG. 22A illustrates a front view of a complete mechanical assembly 1860A, which is similar to FIG. 21A, except the detachable hairbrush unit 1600A is replaced by the detachable hairbrush unit 1600B.

Figure 22B:
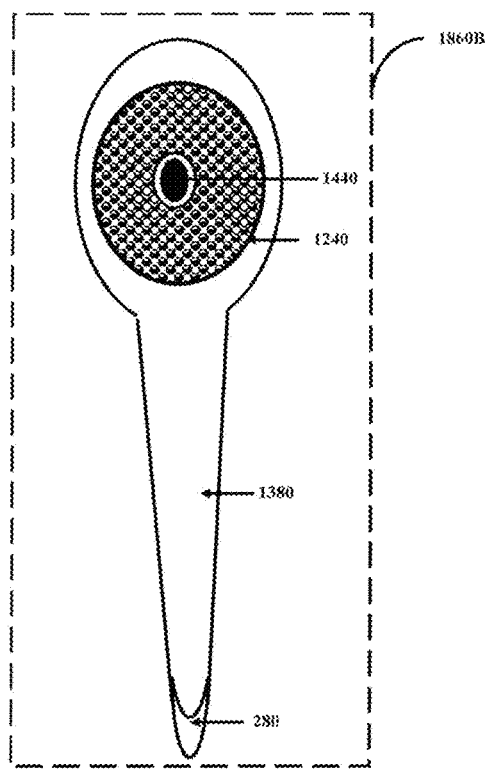

FIG. 22B illustrates a back view 1860B of the complete mechanical assembly 1860A (as illustrated in FIG. 22A). FIG. 22B comprises/includes (a) the bottom electrical contact area 280, (b) the detachable low intensity light module 1240, (c) the mechanical structure 1380 and (d) the unit (for the detachable spray applicator 1520) 1460.

Examples of Composition (Formulation) 540A

By way of an example and not by way of any limitation, an example of a bioactive compound for treatment against lice is *Azadirachta indica/Cinnamomum zeylanicum/Lavendula angustifoli/Melaleuca alternifolia/Mentha piperita/Myristica fragrans/Pimpinella anisum/Pongamia glabra/Syzgium aromaticum* or a mixture of bioactive compounds of about 40 cc *Melaleuca alternifolia*, about 20 cc *Pimpinella anisum* and about 40 cc *Syzgium aromaticum*, wherein the bioactive compound can be in the form of an oil/extract.

By way of an example and not by way of any limitation, an example of a bioactive compound for treatment against dandruff is *Azadirachta indica/Casytha filiformis/Curcuma longa/Eclipta alba/Emblica officinalis, Hibiscus rosa/Nyctanthes arbotristis/Pongamia glabra/Rubia cordifolia/Sesame indicum/Syzygium cumini* or a mixture of bioactive compounds of about 10 cc *Argania spinosa* L, about 10 cc *Calophyllum inophyllum*, about 30 cc *Cocos nucifera*, about 5 cc *Lavendula angustifolia*, about 25 cc *Melaleuca alternifolia*, about 5 cc *Syzgium aromaticum* and about 15 cc Syzygium cumini, wherein the bioactive compound can be in the form of an oil/extract.

By way of an example and not by way of any limitation, an example of a mixture of bioactive compounds for growth and protection of hair is about 10 cc *Camellia sinensis*, about 10 cc *Centella asiatica*, about 10 cc *Cocus nucifera*, about 10 cc *Emblica officinalis*, about 10 cc *Humulus lupulus*, about 20 cc *Pisum sativum* (Pea) sprout, about 10 cc *Salvia officinalis*, about 10 cc *Scutellaria baicelensis* and about 10 cc *Triticum vulgare*, wherein the bioactive compound can be in the form of an oil/extract.

Furthermore, a bioactive compound of about 10 cc *Aloe barbadensis/Argania spinosa/Avena sativa/Citrus paradisi/Glycine max/Olea lancifolia/Oryza sativa/Simmondsia chinensis/Vitis vinifera* (wherein the bioactive compound can be in the form of an oil/extract) can be added to the above mixture, as described in the previous paragraph.

By way of an example and not by way of any limitation, an example of a mixture of bioactive compounds for growth and protection of hair is about 10 cc *Aconiti ciliare* Tuber, about 10 cc *Centella asiatica*, about 20 cc *Emblica officinalis*, about 10 cc *Humulus lupulus*, about 30 cc *Pisum sativum* (Pea) sprout, about 10 cc *Scutellaria baicelensis* and about 10 cc *Triticum vulgare*, wherein the bioactive compound can be in the form of an oil/extract.

By way of an example and not by way of any limitation, an example of a mixture of bioactive compounds for treatment of grey hair is about 10 cc *Azadirachta indica*, about 20 cc *Curcuma longa*, about 10 cc *Eclipta alba*, about 30 cc *Emblica officinalis*, about 10 cc *Hibiscus rosa*, about 10 cc *Pongamia glabra* and about 10 cc *Sesame indicum*, wherein the bioactive compound can be in the form of an oil/extract.

Furthermore, a mixture of extracts or oils, about 10 cc *Aconiti ciliare* Tuber, about 10 cc *Centella asiatica*, about 20 cc *Emblica officinalis*, about 10 cc *Humulus lupulus*, about 30 cc *Pisum sativum* sprout, about 10 cc *Scutellaria baicelensis* and about 10 cc *Triticum vulgare* can be beneficial for growth and protection of hair.

However, the effectiveness of the mixtures, as described in the previous paragraphs can be improved by either an oil-in-oil emulsion/nanoemulsion or oil-in-water emulsion/nanoemulsion. Furthermore, the oil-in-water nanoemulsion can be dried to form nanoparticles.

A bioactive compound minoxidil can be utilized for growth and protection of hair.

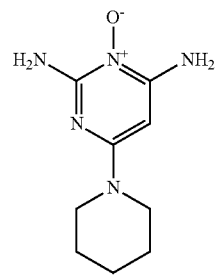 [SMILES: Nc1cc(N2CCCCC2)nc(N)[n+]1[O-]]

Furthermore, minoxidil with a suitable amount of retinoic acid (retin-A) can be utilized to enhance its synergetic effectiveness.

Furthermore, minoxidil with a suitable amount of vitamin A encapsulated or caged within a nanoshell can be utilized to enhance its synergetic effectiveness.

Minoxidil with a suitable amount of niacinamide encapsulated or caged within a nanoshell can be utilized to enhance its synergetic effectiveness.

Minoxidil with a suitable amount of pyrroloquinoline quinone (PQQ) encapsulated or caged within a nanoshell can be utilized to enhance its synergetic effectiveness.

Minoxidil with a suitable amount of resveratrol encapsulated or caged within a nanoshell can be utilized to enhance its synergetic effectiveness.

Minoxidil with suitable amounts of vitamin A and niacinamide encapsulated or caged within a nanoshell can be utilized to enhance its synergetic effectiveness.

Minoxidil with suitable amounts of vitamin A, niacinamide and pyrroloquinoline quinone encapsulated or caged within a nanoshell can be utilized to enhance its synergetic effectiveness.

Minoxidil with suitable amounts of vitamin A, niacinamide, pyrroloquinoline quinone and resveratrol encapsulated or caged within a nanoshell can be utilized to enhance its synergetic effectiveness.

A bioactive compound bimatoprost can be utilized for growth and protection of hair.

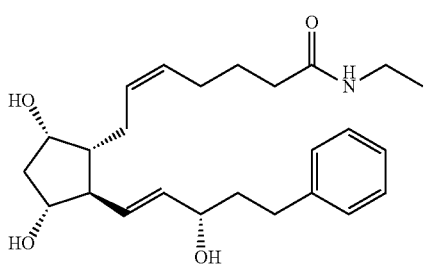 [SMILES: CCNC(=O)CCC/C=C\C[C@@H]1[C@@H](/C=C/[C@@H](O)CCc2ccccc2)[C@H](O)C[C@@H]1O]

Furthermore, bimatoprost with a suitable amount of vitamin A encapsulated or caged within a nanoshell can be utilized to enhance its synergetic effectiveness.

Bimatoprost with a suitable amount of niacinamide encapsulated or caged within a nanoshell can be utilized to enhance its synergetic effectiveness.

Bimatoprost with a suitable amount of pyrroloquinoline quinone encapsulated or caged within a nanoshell can be utilized to enhance its synergetic effectiveness.

Bimatoprost with a suitable amount of resveratrol encapsulated or caged within a nanoshell can be utilized to enhance its synergetic effectiveness.

Bimatoprost with suitable amounts of vitamin A and niacinamide encapsulated or caged within a nanoshell can be utilized to enhance its synergetic effectiveness.

Bimatoprost with suitable amounts of vitamin A, niacinamide and pyrroloquinoline quinone encapsulated or caged within a nanoshell can be utilized to enhance its synergetic effectiveness.

Bimatoprost with suitable amounts of vitamin A, niacinamide, pyrroloquinoline quinone and resveratrol encapsulated or caged within a nanoshell can be utilized to enhance its synergetic effectiveness.

Bimatoprost with suitable amounts of vitamin A, niacinamide, pyrroloquinoline quinine, resveratrol and minoxidil encapsulated or caged within a nanoshell can be utilized to enhance its synergetic effectiveness.

A bioactive compound tofacitinib (tofacitinib citrate) can be utilized for growth and protection of hair.

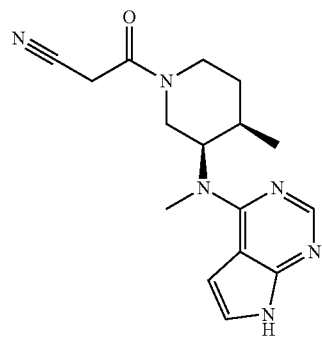 [SMILES: C[C@@H]1CCN(C(=O)CC#N)C[C@@H]1N(C)c1ncnc2[nH]ccc12]

Furthermore, tofacitinib with a suitable amount of vitamin A encapsulated or caged within a nanoshell can be utilized to enhance its synergetic effectiveness.

Tofacitinib with a suitable amount of niacinamide encapsulated or caged within a nanoshell can be utilized to enhance its synergetic effectiveness.

Tofacitinib with a suitable amount of pyrroloquinoline quinone encapsulated or caged within a nanoshell can be utilized to enhance its synergetic effectiveness.

Tofacitinib with a suitable amount of resveratrol encapsulated or caged within a nanoshell can be utilized to enhance its synergetic effectiveness.

Tofacitinib with suitable amounts of vitamin A and niacinamide encapsulated or caged within a nanoshell can be utilized to enhance its synergetic effectiveness.

Tofacitinib with suitable amounts of vitamin A, niacinamide and pyrroloquinoline quinone encapsulated or caged within a nanoshell can be utilized to enhance its synergetic effectiveness.

Tofacitinib with suitable amounts of vitamin A, niacinamide, pyrroloquinoline quinone and resveratrol encapsulated or caged within a nanoshell can be utilized to enhance its synergetic effectiveness.

Tofacitinib with suitable amounts of vitamin A, niacinamide, pyrroloquinoline quinine, resveratrol and minoxidil encapsulated or caged within a nanoshell can be utilized to enhance its synergetic effectiveness.

Tofacitinib with suitable amounts of vitamin A, niacinamide, pyrroloquinoline quinine, resveratrol and bimatoprost encapsulated or caged within a nanoshell can be utilized to enhance its synergetic effectiveness.

A bioactive compound ruxolitinib can be utilized for growth and protection of hair.

[Structure of ruxolitinib shown]

Furthermore, ruxolitinib with a suitable amount of vitamin A encapsulated or caged within a nanoshell can be utilized to enhance its synergetic effectiveness.

Ruxolitinib with a suitable amount of niacinamide encapsulated or caged within a nanoshell can be utilized to enhance its synergetic effectiveness.

Ruxolitinib with a suitable amount of pyrroloquinoline quinone encapsulated or caged within a nanoshell can be utilized to enhance its synergetic effectiveness.

Ruxolitinib with a suitable amount of resveratrol encapsulated or caged within a nanoshell can be utilized to enhance its synergetic effectiveness.

Ruxolitinib with suitable amounts of vitamin A and niacinamide encapsulated or caged within a nanoshell can be utilized to enhance its synergetic effectiveness.

Ruxolitinib with suitable amounts of vitamin A, niacinamide and pyrroloquinoline quinine encapsulated or caged within a nanoshell can be utilized to enhance its synergetic effectiveness.

Ruxolitinib with suitable amounts of vitamin A, niacinamide, pyrroloquinoline quinone and resveratrol encapsulated or caged within a nanoshell can be utilized to enhance its synergetic effectiveness.

Ruxolitinib with suitable amounts of vitamin A, niacinamide, pyrroloquinoline quinine, resveratrol and minoxidil encapsulated or caged within a nanoshell can be utilized to enhance its synergetic effectiveness.

Ruxolitinib with suitable amounts of vitamin A, niacinamide, pyrroloquinoline quinine, resveratrol and bimatoprost encapsulated or caged within a nanoshell can be utilized to enhance its synergetic effectiveness.

Ruxolitinib and tofacitinib with a suitable amount of vitamin A encapsulated or caged within a nanoshell can be utilized to enhance its synergetic effectiveness.

Ruxolitinib and tofacitinib with a suitable amount of niacinamide encapsulated or caged within a nanoshell can be utilized to enhance its synergetic effectiveness.

Ruxolitinib and tofacitinib with a suitable amount of pyrroloquinoline quinone encapsulated or caged within a nanoshell can be utilized to enhance its synergetic effectiveness.

Ruxolitinib and tofacitinib with a suitable amount of resveratrol encapsulated or caged within a nanoshell can be utilized to enhance its synergetic effectiveness.

Ruxolitinib and tofacitinib with suitable amounts of vitamin A and niacinamide encapsulated or caged within a nanoshell can be utilized to enhance its synergetic effectiveness.

Ruxolitinib and tofacitinib with suitable amounts of vitamin A, niacinamide and pyrroloquinoline quinone encapsulated or caged within a nanoshell can be utilized to enhance its synergetic effectiveness.

Ruxolitinib and tofacitinib with suitable amounts of vitamin A, niacinamide, pyrroloquinoline quinone and resveratrol encapsulated or caged within a nanoshell can be utilized to enhance its synergetic effectiveness.

Ruxolitinib and tofacitinib with suitable amounts of vitamin A, niacinamide, pyrroloquinoline quinone, resveratrol and minoxidil encapsulated or caged within a nanoshell can be utilized to enhance its synergetic effectiveness.

Ruxolitinib and tofacitinib with suitable amounts of vitamin A, niacinamide, pyrroloquinoline quinone, resveratrol and bimatoprost encapsulated or caged within a nanoshell can be utilized to enhance its synergetic effectiveness.

A bioactive compound antiandrogen RU 58841 can be utilized for growth and protection of hair.

[Structure of RU58841 shown]

Furthermore, antiandrogen RU 58841 with a suitable amount of vitamin A encapsulated or caged within a nanoshell can be utilized to enhance its synergetic effectiveness.

Antiandrogen RU 58841 with a suitable amount of niacinamide encapsulated or caged within a nanoshell can be utilized to enhance its synergetic effectiveness.

Antiandrogen RU 58841 with a suitable amount of pyrroloquinoline quinone encapsulated or caged within a nanoshell can be utilized to enhance its synergetic effectiveness.

Antiandrogen RU 58841 with a suitable amount of resveratrol encapsulated or caged within a nanoshell can be utilized to enhance its synergetic effectiveness.

Antiandrogen RU 58841 with suitable amounts of vitamin A and niacinamide encapsulated or caged within a nanoshell can be utilized to enhance its synergetic effectiveness.

Antiandrogen RU 58841 with suitable amounts of vitamin A, niacinamide and pyrroloquinoline quinone encapsulated or caged within a nanoshell can be utilized to enhance its synergetic effectiveness.

Antiandrogen RU 58841 with suitable amounts of vitamin A, niacinamide, pyrroloquinoline quinone and resveratrol encapsulated or caged within a nanoshell can be utilized to enhance its synergetic effectiveness.

Antiandrogen RU 58841 with suitable amounts of vitamin A, niacinamide, pyrroloquinoline quinone, resveratrol and minoxidil encapsulated or caged within a nanoshell can be utilized to enhance its synergetic effectiveness.

Antiandrogen RU 58841 with suitable amounts of vitamin A, niacinamide, pyrroloquinoline quinone, resveratrol and bimatoprost encapsulated or caged within a nanoshell can be utilized to enhance its synergetic effectiveness.

Antiandrogen RU 58841 with suitable amounts of vitamin A, niacinamide, pyrroloquinoline quinone, resveratrol and tofacitinib encapsulated or caged within a nanoshell can be utilized to enhance its synergetic effectiveness.

Antiandrogen RU 58841 with suitable amounts of vitamin A, niacinamide, pyrroloquinoline quinone, resveratrol and ruxolitinib encapsulated or caged within a nanoshell can be utilized to enhance its synergetic effectiveness.

Astressin-B peptide can block receptors for corticotropin-releasing factor, involved in the stress response. Thus, Astressin-B peptide can be beneficial for growth and protection of hair.

The Wnt signaling pathways are a group of signal transduction pathways made of proteins that pass signals from outside of a cell through cell surface receptors to the inside of a cell. Activation of Wnt signaling in a safe and controlled way by *Aconiti ciliare* Tuber extract can be beneficial for growth and protection of hair.

A mixture of about 200 mg of catalase (or a chemical derivate or a structural analog of catalase or a pseudocatalase activated via sunlight), about 200 mg of glutathione peroxidase, about 1000 mg of L-methionine, about 100 mg of methionine sulfoxide reductase (MSR), about 200 mcg of selenium amino acid complex (sodium selenite, L-selenomethionin and selenium-methyl L-selenocysteine), about 200 mg superoxide dismutase (SOD), about 15 mg of zinc (L-Opti) and about 200 mg of *Emblica officinalis* extract can be beneficial for growth and protection of hair.

Similarly, a mixture of about 200 mg of catalase (or a chemical derivate or a structural analog of catalase or a pseudocatalase activated via sunlight), about 20 mg of niacin or 100 mg niacinamide, about 20 mg pyrroloquinoline quinone, about 200 mg resveratrol, about 200 mg superoxide dismutase, about 1000 IU vitamin A, about 200 mcg vitamin H and about 15 mg zinc can be beneficial for growth and protection of hair.

It should be noted that niacinamide can be substituted with a suitable amount of niacin.

[For Rejuvenation and Protection of Skin]

FIG. 23A illustrates two detachable skin brush units 1880A/1880B. The detachable skin brush unit 1880A has a fine textured compared to the detachable skin brush unit 1880B. By way of an example and not by way of any limitation, the material for the bristle strands of the detachable skin brush unit 1880A/1880B can be a biocompatible material (e.g., silk fibroin)/biocomposite material/nylon.

FIG. 23B illustrates above two detachable skin brush units 1880C/1880D, each having a hole 1420 close to the center of the frame of each detachable skin brush unit namely 1880C/1880D. The detachable skin brush unit 1880C/1880D can enable motion (including clockwise motion/counter clockwise motion/circular motion)/vibration mechanically within a range of frequencies (e.g., between 40 Hz-100 Hz).

It should be noted that the complete mechanical assembly 1980B can be temperature controlled (via a temperature controller) and coupled with an applicator for heating (e.g., a radiofrequency based heating) and/or cooling on skin.

FIG. 24A illustrates a front surface 1900A and a back surface 1900B of a removable fine textured patch 1920 respectively. The back surface 1900B has an adhesive film.

FIG. 24B illustrates a front surface 1940A and a back surface 1940B of a removable coarse textured patch 1960 respectively. The back surface 1940B has an adhesive film.

Both the removable fine textured patch 1920 and coarse textured patch 1960 can be utilized for microabrasion on skin.

The removable fine textured (less than 50 microns in roughness) patch 1920/coarse textured (more than 50 microns in roughness) patch 1960 can be also infused with a bioactive compound/biologically active molecule (including a regulatory protein/growth factor) or a mixture of bioactive compounds/biologically active molecules (including regulatory proteins/growth factors) 540B for rejuvenation and protection of skin. The bioactive compound/botanical compound/biologically active molecule (including a regulatory protein/growth factor) or the mixture of bioactive compounds/botanical compounds/biologically active molecules (including regulatory proteins/growth factors) 540B can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

The removable fine textured patch 1920/coarse textured patch 1960 can comprise/include a scaffold/microscaffold/nanoscaffold. The scaffold/microscaffold/nanoscaffold can be infused with a bioactive compound/biologically active molecule (including a regulatory protein/growth factor) or a mixture of bioactive compounds/biologically active molecules (including regulatory proteins/growth factors) 540B for rejuvenation and protection of skin. The bioactive compound/botanical compound/biologically active molecule (including a regulatory protein/growth factor) or the mixture of bioactive compounds/botanical compounds/biologically active molecules (including regulatory proteins/growth factors) 540B can be encapsulated within a nanoshell. The nanoshell can comprise/include ligand(s) to bind/chemically couple with specific receptors of a cell. Furthermore, the above bioactive compound/botanical compound or the mixture of bioactive compounds/botanical compounds can be in an emulsion/microemulsion/nanoemulsion.

Furthermore, the removable fine textured patch 1920/coarse textured patch 1960 can be replaced by a scaffold/microscaffold/nanoscaffold. The scaffold/microscaffold/nanoscaffold can be three-dimensionally printed/nano printed.

FIG. 25A illustrates a mechanical assembly 1980A, which comprises/includes (a) an electronic subsystem for motion/vibration (including clockwise motion/counter clockwise motion/circular motion) 1360D, (b) the mechanical structure 1380 and (c) the detachable skin brush unit 1880A/1880B. The other components are (a) the power indicator 220, (b) the mechanical motion/vibration indicator 220B and (c) the bottom electrical contact area 280

FIG. 25B illustrates a complete mechanical assembly 1980B of 1980A (as illustrated in FIG. 25A).

It should be noted that the complete mechanical assembly 1980B can be temperature controlled (via a temperature controller) and coupled with an applicator for heating (e.g., a radiofrequency based heating) and/or cooling on skin.

FIG. 26A illustrates a mechanical assembly 2000A, which comprises/includes (a) the electronic subsystem for motion/vibration (including clockwise motion/counter clockwise motion/circular motion) 1360D, (b) the mechanical structure 1380 and (c) the detachable skin brush unit 1880A, wherein the detachable skin brush unit 1880A comprises/includes the removable fine textured patch 1920/coarse textured patch 1960. The other components are (a) the power indicator 220, (b) the mechanical motion/vibration indicator 220B and (c) the bottom electrical contact area 280.

FIG. 26B illustrates a complete mechanical assembly 2000B of 2000A (as illustrated in FIG. 26A).

FIG. 27A illustrates a mechanical assembly 2020A, which comprises/includes (a) the detachable low intensity light module 1240, (b) the electronic subsystem (for the detachable low intensity light module 1240) 1360C, (c) the electronic subsystem for motion/vibration (including clockwise motion/counter clockwise motion/circular motion) 1360D, (d) the mechanical structure 1380 and (e) the detachable skin brush unit 1880A/1880B. The other components are (a) the power indicator 220, (b) the light module indicator (for the detachable low intensity light module 1240) 220A, (c) the mechanical motion/vibration indicator 220B and (d) the bottom electrical contact area 280.

FIG. 27B illustrates a front view of the complete mechanical assembly 2020B of 2020A (as illustrated in FIG. 27A).

FIG. 27C illustrates a back view 2020C of the complete mechanical assembly 2020B (as illustrated in FIG. 27B). FIG. 27C comprises/includes (a) the bottom contact area 280, (b) the detachable low intensity light module 1240 and (c) the mechanical structure 1380.

FIG. 28A illustrates a mechanical assembly 2040A. FIG. 28A is similar to FIG. 27A with an addition of the removable fine textured patch 1920 or coarse textured patch 1960, but without the detachable skin brush unit 1880B.

FIG. 28B illustrates a front view of a complete mechanical assembly 2040B of 2040A (as illustrated in FIG. 28A).

FIG. 28C illustrates a back view 2040C of the complete mechanical assembly 2040B (as illustrated in FIG. 28B). FIG. 28C comprises/includes (a) the bottom contact area 280, (b) the detachable low intensity light module 1240 and (c) the mechanical structure 1380.

FIG. 29A illustrates a mechanical assembly 2060A, which comprises/includes (a) the detachable spray applicator (comprising/including the ultrasonic wave generator/vibrator) 1300, (b) the connector (for the detachable spray applicator 1300) 1320, (c) the push button (for the detachable spray applicator 1300) 1340, (d) the electronic subsystem (for the detachable spray applicator 1300) 1360A, (e) the electronic subsystem for motion/vibration (including clockwise motion/counter clockwise motion/circular motion) 1360D, (f) the mechanical structure 1380 and (g) the detachable skin brush unit 1880C/1880D. The other components are (a) the power indicator 220, (b) the mechanical motion/vibration indicator 220B, (c) the vibration (due to the ultrasonic wave generator/vibrator) intensity indicator 240A, (d) the spray indicator 260 and (e) the bottom electrical contact area 280.

FIG. 29B illustrates a complete mechanical assembly 2060B of 2060A (as illustrated in FIG. 29A).

FIG. 29C illustrates a complete mechanical assembly 2060C, which comprises/includes the removable fine textured patch 1920 or coarse textured patch 1960 with the complete mechanical assembly 2060B (as illustrated in FIG. 29B), but without the detachable skin brush unit 1880D.

FIG. 30A illustrates a mechanical assembly 2080A, which comprises/includes (a) the electronic subsystem (for the detachable spray applicator 1520) 1360B, (b) the electronic subsystem for motion/vibration (including clockwise motion/counter clockwise motion/circular motion) 1360D, (c) the mechanical structure 1380, (d) the unit (for the detachable spray applicator 1520) 1460, (e) the detachable spray applicator (comprising/including the nozzle) 1520 and (f) the detachable skin brush unit 1880C/1880D. The other components are (a) the power indicator 220, (b) the mechanical motion/vibration indicator 220B, (c) the vibration (due to the nozzle) intensity indicator 240B, (d) the spray indicator 260 and (e) the bottom electrical contact area 280.

FIG. 30B illustrates a complete mechanical assembly 2080B of 2080A (as illustrated in FIG. 30A).

FIG. 30C illustrates a complete mechanical assembly 2080C. FIG. 30C is similar to FIG. 30B with an addition of the removable fine textured patch 1920 or coarse textured patch 1960, but without the detachable skin brush unit 1880D FIG. 31A illustrates a front view of a mechanical assembly 2100A, which comprises/includes (a) the detachable cap 420, (b) the detachable low intensity light module 1240, (c) the detachable spray applicator (comprising/including the ultrasonic wave generator/vibrator) 1300, (d) the push button (for the detachable spray applicator 1300) 1340, (e) the electronic subsystem (for the detachable spray applicator 1300) 1360A, (f) the electronic subsystem (for the detachable low intensity light module 1240) 1360C and (g) the mechanical structure 1380. The other components are (a) the power indicator 220, (b) the light module indicator (for the detachable low intensity light module 1240) 220A, (c) the vibration (due to the ultrasonic wave generator/vibrator) intensity indicator 240A, (d) the spray indicator 260 and (e) the bottom electrical contact area 280. The connector (for the detachable spray applicator 1300) 1320 is not shown due to the shadow of the detachable low intensity light module 1240.

FIG. 31B illustrates a back view 2100B of the mechanical assembly 2100A (as illustrated in FIG. 31A). FIG. 31B comprises/includes (a) the bottom contact area 280, (b) the detachable low intensity light module 1240, (c) the push button (for the detachable spray applicator 1300) 1340 and (d) the mechanical structure 1380.

FIG. 32A illustrates a front view of a mechanical assembly 2120A, which comprises/includes (a) the detachable cap 420, (b) the detachable low intensity light module 1240, (c) the electronic subsystem (for the detachable spray applicator 1520) 1360B, (d) the electronic subsystem (for the detachable low intensity light module 1240) 1360C, (e) the mechanical structure 1380, (f) the unit (for the detachable spray applicator 1520) 1460 and (g) the detachable spray applicator (comprising/including the nozzle) 1520. The other components are (a) the power indicator 220, (b) the light module indicator (for the detachable low intensity light module 1240) 220A, (c) the vibration (due to the nozzle) intensity indicator 240B, (d) the spray indicator 260 and (e) the bottom electrical contact area 280.

FIG. 32B illustrates a back view 2120B of the mechanical assembly 2120A (as illustrated in FIG. 32A). FIG. 32B comprises/includes (a) the bottom electrical contact area 280, (b) the detachable low intensity light module 1240, (c) the mechanical structure 1380 and (d) the unit (for the detachable spray applicator 1520) 1460.

FIG. 33A illustrates a mechanical assembly 2140A, which comprises/includes (a) the detachable low intensity light module 1240, (b) the detachable spray applicator (comprising/including the ultrasonic wave generator/vibrator) 1300, (c) the push button (for the detachable spray applicator 1300) 1340, (d) the electronic subsystem (for the detachable spray applicator 1300) 1360A, (e) the electronic subsystem (for the detachable low intensity light module 1240) 1360C, (f) the electronic subsystem for motion/vibration (including clockwise motion/counter clockwise motion/circular motion) 1360D, (g) the mechanical structure 1380 and (h) the detachable skin brush unit 1880C/1880D. The other components are (a) the power indicator 220, (b) the light module indicator (for the detachable low intensity light module 1240) 220A, (c) the mechanical motion/vibration indicator 220B, (d) the vibration (due to the ultrasonic wave generator/vibrator) intensity indicator 240A, (e) the spray indicator 260 and (f) the bottom electrical contact area 280. The connector (for the detachable spray applicator 1300) 1320 is not shown due to the shadow of the detachable low intensity light module 1240.

FIG. 33B illustrates a front view 2140B of the complete mechanical assembly 2140A (as illustrated in FIG. 33A).

FIG. 33C illustrates a back view 2140C of the complete mechanical assembly 2140B (as illustrated in FIG. 33B). FIG. 33C comprises/includes (a) the bottom contact area 280, (b) the detachable low intensity light module 1240, (c) the push button (for the detachable spray applicator 1300) 1340 and (d) the mechanical structure 1380.

FIG. 34A illustrates a complete mechanical assembly 2160A. FIG. 34A is similar to FIG. 33B, with an addition of the removable fine textured patch 1920 or coarse textured patch 1960, but without the detachable skin brush unit 1880D.

FIG. 34B illustrates a back view 2160B of the complete mechanical assembly of 2160A (as illustrated in FIG. 34A). FIG. 34B comprises/includes (a) the bottom contact area 280, (b) the detachable low intensity light module 1240, (c) the push button (for the detachable spray applicator 1300) 1340 and (d) the mechanical structure 1380.

FIG. 35A illustrates a front view of a mechanical assembly 2180A, which comprises/includes (a) the detachable low intensity light module 1240, (b) the electronic subsystem (for the detachable spray applicator 1520) 1360B, (c) the electronic subsystem (for the detachable low intensity light module 1240) 1360C, (d) the electronic subsystem for motion/vibration (including clockwise motion/counter clockwise motion/circular motion) 1360D, (e) the mechanical structure 1380, (f) the unit (for the detachable spray applicator 1520) 1460, (g) the detachable spray applicator (comprising/including the nozzle) 1520 and (h) the detachable skin brush unit 1880C/1880D. The other components are (a) the power indicator 220, (b) the light module indicator (for the detachable low intensity light module 1240) 220A, (c) the mechanical motion/vibration indicator 220B, (d) the vibration (due to the nozzle) intensity indicator 240B, (e) the spray indicator 260 and (f) the bottom electrical contact area 280.

The connector (for the detachable spray applicator 1300) 1320 is not shown due to the shadow of the detachable low intensity light module 1240.

FIG. 35B illustrates a front view of a complete mechanical assembly 2180B of 2180A (as illustrated in FIG. 35A).

FIG. 35C illustrates a back view of the complete mechanical assembly 2180C of 2180B (as illustrated in FIG. 35B). FIG. 35C comprises/includes (a) the bottom contact area 280, (b) the detachable low intensity light module 1240, (c) the mechanical structure 1380 and (d) the unit (for the detachable spray applicator 1520) 1460.

FIG. 36A illustrates a front view of a mechanical assembly 2200A, which is similar to FIG. 35A with an addition of the removable fine textured patch 1920 or coarse textured patch 1960, but without the detachable brush 1880D.

FIG. 36B illustrates a back view 2200B of the mechanical assembly 2200A (as illustrated in FIG. 36A). FIG. 36B comprises/includes the bottom contact area 280, the detachable low intensity light module 1240, the mechanical structure 1380 and the unit (for the detachable spray applicator 1520) 1460.

It should be noted that the detachable spray applicator 1300/1520 with the detachable brush 1880D can be utilized for other personal care devices (e.g., a toothbrush). Such devices can be co-packaged or integrated with the detachable light intensity module 1240.

It should be noted that all above embodiments can be coupled with an augmented reality (AR) application (app) based mirror (e.g., a mirror superimposing a real image and a computer generated image) to enhance rejuvenation and/or protection of skin, by matching to relevant skincare products.

Details of Augmented Reality have been described/disclosed in U.S. Non-Provisional patent application Ser. No. 14/120,835 entitled "AUGMENTED REALITY PERSONAL ASSISTANT APPARATUS", filed on Jul. 1, 2014, (which resulted in a U.S. Pat. No. 9,823,737, issued on Nov. 21, 2017).

Furthermore, the augmented reality application based mirror can be coupled with an artificial intelligence (AI) algorithm or an artificial neural network (ANN) algorithm based three-dimensional simulation(s) to enhance rejuvenation and/or protection of skin (e.g., via a chatbot).

The three-dimensional simulation(s) can generally utilize a user's selfie and questionnaires as the input data.

The three-dimensional simulation(s) can be in real-time.

The artificial intelligence or artificial neural network algorithm can reside in a cloud based server.

Details of Artificial Intelligence have been described/disclosed in U.S. Non-Provisional patent application Ser. No. 13/448,378 entitled "SYSTEM & METHOD FOR MACHINE LEARNING BASED USER APPLICATION", filed on Apr. 16, 2012, (which resulted in a U.S. Pat. No. 9,697,556, issued on Jul. 4, 2017).

Furthermore, the three-dimensional simulation(s) can enable three-dimensionally printed artificial skin (details of three-dimensional printing are described in later paragraphs) embedding a bioactive compound/botanical compound/biologically active molecule (including a regulatory protein/growth factor) or a mixture of bioactive compounds/botanical compounds/biologically active molecules (including regulatory proteins/growth factors, as in Table 8). The biologically active molecule can include an equivalent (either structurally (chemical) equivalent and/or functionally) molecule mimicking a molecule released by a stem cell for protection of skin. The biologically active molecule can also include a molecule for the protection of a stem cell for skin.

By way of an example and not by way of any limitation, FIG. 37A illustrates various nanooptical elements 2220A (therein after represented by a generalized infinity ∞ symbol), which can be a coreshell/sphere/triangle/disk/rod/bowtie/circular hole surrounding by concentric grooves/C aperture/L aperture/designed based on a biological system (e.g., a light harvesting protein in photosynthesis). The material for the nanooptical element can be semiconductor (e.g., silicon)/ceramic (e.g., titanium nitride)/metal (e.g., aluminum/gold/silver/magnesium)/transparent conducting oxide (e.g., zinc oxide)/two-dimensional material (e.g., graphene).

Furthermore, the generalized nanooptical elements 2220A can be coated with a layer of a two-dimensional material (e.g., graphene).

The nanooptical element can be fabricated/constructed by electron-beam lithography and/or focused ion-beam milling.

FIG. 37B illustrates the generalized nanooptical elements 2220A, functionalized (with a cationic lipid layer e.g., a phospholipid bilayer) generalized nanooptical elements 2220B and functionalized generalized nanooptical elements 2220C, which can be further chemically coupled with an engineered riboswitch/notch molecule/siRNA/siRNA oligos/siRNAmod/optical CRISPR/Cas9 system. siRNA oligos has small size of 21-23 oligos. siRNA can be chemically modified as siRNAMod to enhance enhanced activity, serum stability and reduced less off-targets/immunological activation. An optical CRISPR/Cas9 system is a genetically encoded light (optically) activated Cas9. Additionally, an engineered riboswitch may require an adhesive molecule for binding with a specific gene.

FIG. 37C illustrates generalized (biocompatible/biodissolvable) nanooptical elements 2220A1, functionalized generalized (biocompatible/biodissolvable) nanooptical elements 2220B1 and functionalized generalized (biocompatible/biodissolvable) nanooptical elements 2220C1, which can be further chemically coupled with an engineered riboswitch/notch molecule/siRNA/siRNA oligos/siRNAmod/optical CRISPR/Cas9 system.

A biocompatible/biodissolvable nanooptical element can be realized by fabricating the generalized nanooptical elements 2220A1/2220B1/2220C1 with a biocompatible/biodissolvable material (e.g., magnesium/zinc oxide).

The maximum dimension of each nanooptical element of the generalized nanooptical elements 2220A/2220B/2220C or each nanooptical element of the generalized (biocompatible/biodissolvable) nanooptical elements 2220A1/2220B1/2220C1 is less than 250 nanometers.

FIG. 38A illustrates a nanocarrier 2240A, which can encapsulate 540B and/or the generalized nanooptical elements 2220A/2220B/2220C and/or generalized (biocompatible/biodissolvable) nanooptical elements 2220A1/2220B1/2220C1. The nanocarrier 2240A has only one type of ligands to chemically bind with one type of receptors on a cell.

FIG. 38B illustrates a nanocarrier 2240B, which can encapsulate 540B and/or the generalized nanooptical elements 2220A/2220B/2220C and/or generalized (biocompatible/biodissolvable) nanooptical elements 2220A1/2220B1/2220C1. The nanocarrier 2240B has two types of ligands to chemically bind with two types of receptors on a cell-thus enhancing specificity of delivery of the generalized nanooptical elements 2220A/2220B/2220C or generalized (biocompatible/biodissolvable) nanooptical elements 2220A1/2220B1/2220C1.

The maximum dimension (e.g., diameter) of the nanocarrier 2240A/2240B is less than 500 nanometers.

It should be noted that 540B or engineered riboswitch/notch molecule/siRNA/siRNA oligos/siRNAmod/optical CRISPR/Cas9 system can be encapsulated within the nanocarrier 2240A/2240B without even chemically coupling with the functionalized generalized nanooptical elements 2220C or generalized (biocompatible/biodissolvable) nanooptical elements 2220C1.

In an example, 540B can be luric acid and/or an isolated active protein from *Propionibacterium acnes* phages for treatment against acne. Furthermore, luric acid and/or an isolated active protein from *Propionibacterium acnes* phages can be encapsulated within the nanocarrier 2240A/2240B (or the nanoshell) or said nanocarrier 2240A/2240B (or the nanoshell) can also be infused in the patch 1920/1960 for delivery of 540B.

In another example, 540B can be 2-(4-morpholinoanilino)-6-cyclohexylaminopurine or Lomaiviticin A (or its chemical/structural analogue), which can induce death of skin cancer cells/cancer cells, by cleaving skin cancer cell's/cancer cell's DNA structure. A chemical structure of Lomaiviticin A is given below.

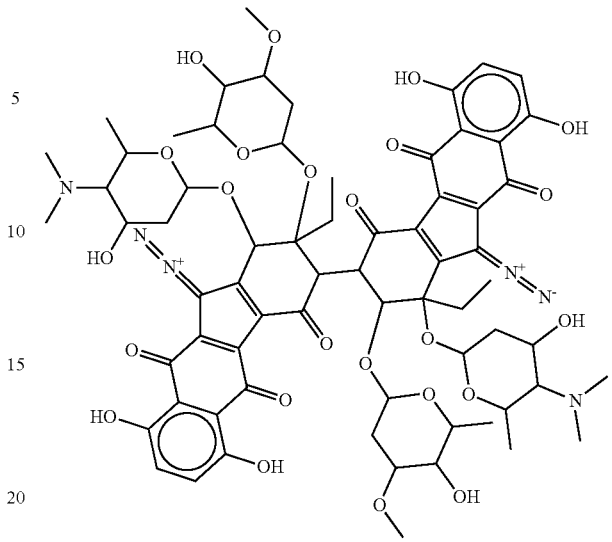

Furthermore, both lipid and cyclodextrin based nanocarrier can be utilized for siRNA/siRNA oligos/siRNAmod.

The outer surface of the nanocarrier 2240A/2240B can be coated with an immune shielding functional surface to protect from a human body's inherent immune surveillance. A polymer membrane (e.g., polyethylene glycol (PEG) polymer/water-like polymer) can be utilized as an immune shielding functional surface. Polyethylene glycol (PEG) membrane is a low-toxicity polymer and it can shield against hydrophobic and/or electrostatic interactions. Alternatively, a natural red blood/artificial red blood cell/three-dimensionally printed blood cell membrane can be also utilized as an immune shielding functional surface.

FIG. 39A illustrates delivery of the 540B and/or generalized nanooptical elements 2220A/2220B/2220C and/or generalized (biocompatible/biodissolvable) nanooptical elements 2220A1/2220B1/2220C1 into a cell via the nanocarrier 2240A (decorated with one ligand) and subsequent release of an engineered riboswitch/notch molecule/siRNA/siRNA oligos/siRNAmod/optical CRISPR/Cas9 system from the generalized nanooptical elements 2220C or generalized (biocompatible/biodissolvable) nanooptical elements 2220C1 upon exposure to light at a plasmon resonance wavelength.

FIG. 39B illustrates delivery of the 540B and/or generalized nanooptical elements 2220A/2220B/2220C and/or generalized (biocompatible/biodissolvable) nanooptical elements 2220A1/2220B1/2220C1 into a cell via the nanocarrier 2240B (decorated with two ligands) and subsequent release of an engineered riboswitch/notch molecule/siRNA/siRNA oligos/siRNAmod/optical CRISPR/Cas9 system from the generalized nanooptical elements 2220C or generalized (biocompatible/biodissolvable) nanooptical elements 2220C1 upon exposure to light at a plasmon resonance wavelength.

FIG. 39C illustrates binding/chemical coupling of an engineered riboswitch/notch molecule/siRNA/siRNA oligos/siRNAmod/optical CRISPR/Cas9 onto a specific gene. It should be noted that an engineered riboswitch may require an adhesive molecule for binding/chemical coupling with a specific gene.

FIG. 39D illustrates a flow chart method to control/chemically couple/edit of a gene, utilizing an engineered riboswitch/notch molecule/siRNA/siRNA oligos/siR- NAmod/optical CRISPR/Cas9 into a cell. In step 10 select a gene/gene circuit/signaling circuit to control/chemically couple/edit. In step 11, select an engineered riboswitch/notch molecule/siRNA/optical CRISPR/Cas9 to control/chemically couple/edit the gene/gene circuit/signaling circuit as in step 10. In step 12, design and fabricate/construct the generalized nanooptical elements 2220C or generalized (biocompatible/biodissolvable) nanooptical elements 2220C1 (functionalized with an engineered riboswitch/notch molecule/siRNA/siRNA oligos/siRNAmod/optical CRISPR/Cas9) at a defined plasmonic resonance. In step 13, encapsulate generalized nanooptical elements 2220C or generalized (biocompatible/biodissolvable) nanooptical elements 2220C1 into the nanocarrier 2240A/2240B. The outer surface of the nanocarrier 2240A/2240B can be decorated with an immune shielding functional surface to protect from a human body's inherent immune surveillance, as described in the previous paragraph. In step 14, introduce generalized nanooptical elements 2220C or generalized (biocompatible/biodissolvable) nanooptical elements 2220C1 (functionalized with an engineered riboswitch/notch molecule/siRNA/siRNA oligos/siRNAmod/optical CRISPR/Cas9) into a cell. In step 15, release an engineered riboswitch/notch molecule/siRNA/siRNA oligos/siRNAmod/optical CRISPR/Cas9 from the generalized nanooptical elements 2220C or generalized (biocompatible/biodissolvable) nanooptical elements 2220C1 (functionalized with an engineered riboswitch/notch molecule/siRNA/siRNA oligos/siRNAmod/optical CRISPR/Cas9) into a cell for controlling/chemically coupling/editing. It should be noted that the optical CRISPR/Cas9 will require an additional photo excitation from a light source (e.g., a laser). In step 16, evaluate the control/chemically couple/edit of the gene/gene circuit/signaling circuit (according to the step 10). For in vivo therapeutic applications, generalized (biocompatible/biodissolvable) nanooptical elements 2220C1 should be utilized.

Sebum production is partly regulated by androgen. Androgen receptors are located within the basal layer of sebaceous glands. In the presence of excess sebum, acne-causing bacteria such as *Propionibacterium acnes* and *Staphylococcus epidermis* colonize skin surface in increasing numbers. These bacteria disrupt the pH balance of skin-further increasing sebum production and abnormal cycle of inflammation which produces the inflammatory lesions (observed during moderate and severe breakouts of acne pimples).

FIG. 40A illustrates a liquid mixed with the generalized nanooptical elements 2220A/2220B/2220C or generalized (biocompatible/biodissolvable) nanooptical elements 2220A1/2220B1/2220C1 on acne pimples. The generalized nanooptical elements 2220A/2220B/2220C or generalized (biocompatible/biodissolvable) nanooptical elements 2220A1/2220B1/2220C1 can be decorated with a ligand(s) to bind with one or more types of specific receptors on acne pimples (e.g. androgen receptors). Ultrasound wave beam 2260 can be utilized first to drive the generalized nanooptical elements 2220A/2220B/2220C or generalized (biocompatible/biodissolvable) nanooptical elements 2220A1/2220B1/2220C1 into acne pimples and then followed by a pulsed laser excitation 2280 at a plasmonic resonance to treat acne pimples.

FIG. 40B illustrates a semi-rigid/flexible/conformal substrate 2300A, which comprises/includes the generalized nanooptical elements 2220A/2220B/2220C or generalized (biocompatible/biodissolvable) nanooptical elements 2220A1/2220B1/2220C1 placed on acne pimples. The nanooptical generalized elements 2220A/2220B/2220C or generalized (biocompatible/biodissolvable) nanooptical elements 2220A1/2220B1/2220C1 can be decorated with a ligand(s) to bind with one or more types of receptors on acne pimples. Ultrasound wave beam 2260 can be utilized to drive the generalized nanooptical elements 2220A/2220B/2220C or generalized (biocompatible/biodissolvable) nanooptical elements 2220A1/2220B1/2220C1 into acne pimples and then followed by a pulsed laser excitation 2280 at a plasmonic resonance to treat acne pimples.

FIG. 40C is similar to FIG. 40B, except the semi-rigid/flexible/conformal substrate 2300A can be replaced by the biocompatible/biodissolvable semi-rigid/flexible/conformal (e.g., a pure silk substrate) 2300B on acne pimples.

FIG. 40D illustrates an accumulation of the generalized nanooptical elements 2220A/2220B/2220C or generalized (biocompatible/biodissolvable) nanooptical elements 2220A1/2220B1/2220C1 at a root of an acne pimple. The above nanooptical elements can be excited by an ultrasound wave beam 2260 and/or a pulsed laser excitation 2280 for treating acne pimples.

Similarly, 40E illustrates an accumulation of the generalized nanooptical elements 2220A/2220B/2220C or generalized (biocompatible/biodissolvable) nanooptical elements 2220A1/2220B1/2220C1 at a root of an unwanted hair. The above nanooptical elements can be excited by an ultrasound wave beam 2260 and/or a pulsed laser excitation 2280 for removal of an unwanted hair.

It should be noted that a different pulsed laser excitation with a different duty cycle/laser intensity/laser pulse width/laser wavelength may be needed in the case of hair removal, when compared with acne treatment.

Gold nanooptical element shaped as Swiss-crosses (wherein each cross is about 30 nanometers thick with horizontal and vertical arm lengths of 150 and 100 nanometers respectively) can convert sub-picosecond pulses of laser light at a plasmonic resonance into ultrahigh frequency sound waves.

FIG. 40F illustrates a nanosystem 2240C, which comprises/includes a nanoshell A, nanoshell B and nanoshell C. The nanoshell A can be a polyethylene-glycol based polymer decorated with a small peptide to bind with specific receptor of a cell. The nanoshell A with a polyethylene-glycol based polymer can evade human immune system. The nanoshell A can encapsulate/cage a cancer drug(s) (e.g., doxorubicin and/or nitrobenzaldehyde and/or Lomaiviticin A) and/or a photosensitizer (e.g., aminolevulinic acid and/or a vitamin E analog mitocan) and/or an RNAi molecule(s) and/or p53 protein. A specific group of mitocan, the vitamin E analog can act on mitochondria to increase reactive oxygen species (ROS) production. The nanoshell A can also act as a photosensitizer. The nanoshell A can be chemically coupled with a near-infrared fluorescent polymer to visualize its accumulation at cancer cells. It should be noted that an ultraviolet wavelength laser may be required for photoactivating nitrobenzaldehyde. The photosensitizer can release reactive oxygen species upon activated/stimulated by a (continuous wave/pulsed) laser light of a suitable wavelength and a suitable intensity/dose. The nanoshell B is an upconverting nanoshell which converts a (continuous wave/pulsed) laser light of near-infrared wavelength into a (continuous wave/pulsed) laser light of visible wavelength. The nanoshell C is a cerium fluoride nanoparticle. Cerium fluoride can also release reactive oxygen species upon activated/stimulated by x-ray of a suitable dose.

FIG. 40G illustrates destruction of acne pimples/skin cancer cells/cancer cells, when the nanosystem 2240C is taken up by acne pimples/skin cancer cells/cancer cells, upon activated/stimulated by a near-infrared (continuous wave/pulsed) laser light of a suitable intensity/dose and x-ray of a suitable dose. Furthermore, extra copies of p53 protein can condemn skin cancer cells/cancer cells to death. Any leftover nanocomponents of the nanosystem 2240C can be filtered out by the kidney.

FIG. 40H illustrates a nanosystem 2240D, which comprises/includes a tube shaped nanoscaled DNA cargo/metal (e.g., gold) rod (which is about 35 nm long and about 10 nm in width). The nanosystem 2240D can be coated with lipid oleate and DOTAP to enhance its interaction and penetration into cells. The tube shaped DNA cargo/metal rod can be coupled/chemically coupled with a heat shock protein and/or TRAIL protein. The tube shaped DNA cargo/metal rod can be further coupled/chemically coupled with the nanoshell A, nanoshell B, nanoshell C by strands of biological material (e.g., apatmers/DNAs/RNAs). Furthermore, the tube shaped DNA cargo/metal rod can be coupled/chemically coupled with metal (e.g., gold) spheres by strands of biological material. The nanoshell A, nanoshell B, nanoshell C and metal spheres can be decorated with immune evading surface, as described in the previous paragraph. In case of the tube shaped nanoscaled DNA cargo, the tube shaped DNA cargo can encapsulate/cage a cancer drug(s) and/or a photosensitizer and/or an RNAi molecule(s) and/or extra copies of p53 protein. The nanoshell A can be a polyethylene-glycol based polymer, which may evade human immune system. The nanoshell A can encapsulate/cage a cancer drug(s) and/or a photosensitizer and/or an RNAi molecule(s) and/or extra copies of p53 protein. A specific group of mitocan, the vitamin E analog can act on mitochondria to increase reactive oxygen species production. The nanoshell A can also act as a photosensitizer. The nanoshell A can be chemically coupled with a near-infrared fluorescent polymer to visualize its accumulation at cancer cells. It should be noted that an ultraviolet wavelength laser may be required for photoactivating nitrobenzaldehyde. The photosensitizer can release reactive oxygen species upon activated/stimulated by a (continuous wave/pulsed) laser light of a suitable wavelength and a suitable intensity/dose. The nanoshell B is an upconverting nanoshell which converts a (continuous wave/pulsed) laser light of near-infrared wavelength into a (continuous wave/pulsed) laser light of visible wavelength. The nanoshell C is a cerium fluoride nanoparticle. Cerium fluoride can release reactive oxygen species upon activated/stimulated by x-ray of a suitable dose. The strands of the biological material can also comprise/include a cancer drug(s) and/or a photosensitizer and/or an RNAi molecule(s) and/or extra copies of p53 protein. It should be noted that about 15 nanoshells can be integrated with the tube shaped nanoscaled DNA cargo/gold rod.

Furthermore, a conversion of near-infrared (continuous wave/pulsed) laser light to visible (continuous wave/pulsed) laser light can be also realized by a four-wave mixing method.

FIG. 40I illustrates entry of the nanosystem 2240D to skin cancer cells/cancer cells.

FIG. 40J illustrates destruction of acne pimples/skin cancer cells/cancer cells, when the nanosystem 2240D is taken up by acne pimples/skin cancer cells/cancer cells, upon activated/stimulated by near-infrared (continuous wave/pulsed) laser light of a suitable intensity/dose and x-ray of a suitable dose. Furthermore, extra copies of p53 protein can condemn skin cancer cells/cancer cells to death. Any leftover nanocomponents of the nanosystem 2240D can be filtered out by the kidney.

In some cases, the near-infrared (continuous wave/pulsed) laser light may be guided by a fiber optic system (e.g., a fiber optic bronchoscope). The near-infrared (continuous wave/pulsed) laser light exiting from the fiber optic system can be focused at below the diffraction limited spot, by integrating a nanofocussing element (e.g., the nanofocussing element 2540B, as illustrated in FIG. 42A/42B) with the fiber optic system. An ultraviolet nanoimprint lithography method can be also utilized to print the nanofocusing device 2540B at the exit of an optical fiber of the fiber optic system.

Examples of Topical/Non-Topical Composition (Formulation) 540B

TABLE 5

TOPICAL COMPOSITION (FORMULATION) (540B)

| | Unit | +/−50% | WT % |
|---|---|---|---|
| Botanical | | | |
| Camellia sinensis (Green Tea) Extract | Mg | 200 | 4.87% |
| Daucus carota Extract | Mg | 200 | 4.87% |
| Emblica officinalis Extract | Mg | 200 | 4.87% |
| Hippophae rhamnoides Oil | Mg | 200 | 4.87% |
| Macrocystis pyrifera Extract | Mg | 200 | 4.87% |
| Prunus amygdalus dulcis (Sweet Almond) Oil | Mg | 200 | 4.87% |
| Solanum lycopersicum | Mg | 200 | 4.87% |
| Chemical | | | |
| Acetyl Hexapeptide | Mg | 200 | 4.87% |
| Arbutin | Mg | 200 | 4.87% |
| Caffeine | Mg | 20 | 0.49% |
| Elastatropin | Mg | 200 | 4.87% |
| Haloxyl | Mg | 200 | 4.87% |
| Hyaluronic Acid | Mg | 200 | 4.87% |
| Hydroxytyrosol | Mg | 200 | 4.87% |
| Hydrolyzed Wheat Protein | Mg | 200 | 4.87% |
| Palmitoyl Pentapeptide-4 | Mg | 200 | 4.87% |
| Quercetin (Nanoformulated) | Mg | 200 | 4.87% |
| Resveratrol (Nanoformulated) | Mg | 200 | 4.87% |
| Superoxide Dismutase (SOD) (Nanoformulated) | Mg | 200 | 4.87% |
| Vitamin | | | |
| Pyrroloquinoline Quinone | Mg | 20 | 0.49% |
| Vitamin $B_5$ | Mg | 200 | 4.87% |
| Vitamin E | IU | 400 | 6.49% |
| Total Weight | G | 4.11 | 100.00% |

About 200 mg of Argan oil or about 200 mg of Coconut (preferably mature coconut) oil or about 200 mg of Marula oil or about 200 mg Pomegranate (*Punica granatum*) seed oil or about 200 mg of Red Raspberry seed oil or about 600 mg of Turmeric oil or 600 mg of Winter Rose oil can be added with the topical composition (formulation) in Table 5. About 200 mg of Aloe vera extract or about 200 mg of *Glycyrrhiza glabra* extract or about 200 mg of pine bark extract can be added with the topical composition (formulation) in Table 5. About 100 mg of caviar extract or about 200 mg of silk fibroin can be added with the topical composition (formulation) in Table 5.

About 200 mg of extract of stem cells of leaves of *Lycopersicon esculentum* or about 200 mg of extract of stem cells of *Malus domestica* can be added with the topical composition (formulation) in Table 5.

Regulatory proteins, called growth factors are biologically active molecules. Suitable amounts of growth factors (from stem cells) can be added. These growth factors can also be nanoformulated/nanoencapsulated (for repairing damaged skin). Fibroblasts are a type of cell found in the connective tissue, where fibroblasts produce proteins such as collagen, elastin and GAG, which are all critical to repairing skin density and the overall look/quality of the skin. Suitable amounts of fibroblasts can be added with the topical composition (formulation) in Table 5.

Furthermore, activators of fibroblasts such as 1,3 beta glucan, *chlorella*, EGF, GHK-copper peptides, niacinamide, R-lipoic acid and retinaldehyde and/or the synergistic combination(s) of the above activators of fibroblasts can activate fibroblasts and supply nutrients to fibroblasts. Suitable amounts of activators of fibroblasts can be added with the topical composition (formulation) in Table 5. Furthermore, the above activators of fibroblasts can be nanoformulated/nanoencapsulated. Fibroblast growth factors are critical for repairing damaged skin. Fibroblast growth factors can induce expression of Nrf2, which regulates the expression of proteins involved in the detoxification of reactive oxygen species. Suitable amounts of fibroblast growth factors can be also added with the topical composition (formulation) in Table 5.

About 0.5% by weight of ebselen, a broad spectrum antioxidant can be added with the topical composition (formulation) in Table 5. The chemical structure of ebselen is given below.

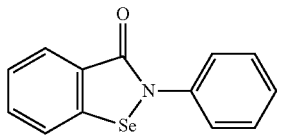 [SMILES: O=c1c2ccccc2[se]n1-c1ccccc1]

A suitable amount of selenohydantoin, an antioxidant and anticancer compound can be added with the topical composition (formulation) in Table 5. Furthermore, a chemical derivative/structural analogue of selenohydantoin can also be utilized. The chemical structure of selenohydantoin is given below.

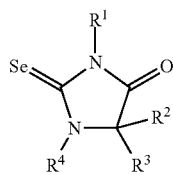

Zinc finger technology (ZFT) can be utilized to repair DNA damage and assist in the production of proteins and antioxidants within skin cells. A suitable amount of zinc finger technology (ZFT) can be added with the topical composition (formulation) in Table 5.

Additionally, a nanoemulsion system/biodegradable substrate (e.g., silk)/silicone-based polymer substrate with a high degree of stability can be utilized for transdermal delivery (via a patch) of the topical composition (formulation) in Table 5.

TABLE 6

TOPICAL COMPOSITION (FORMULATION) (540B)

|  | Unit | +/−50% | WT % |
| --- | --- | --- | --- |
| Botanical | | | |
| Liquorice Extract | Mg | 4 | 1.07% |
| Paper Mulberry Extract | Mg | 4 | 1.07% |
| *Phyllanthus emblica* Extract | Mg | 40 | 10.74% |
| Saffron | Mg | 4 | 1.07% |
| Turmeric | Mg | 40 | 10.74% |
| Chemical | | | |
| Alpha Arbutin | Mg | 20 | 5.37% |
| Alpha Hydroxy Acid (Glycolic Acid/Lactic Acid) | Mg | 20 | 5.37% |
| Gigawhite | Mg | 40 | 10.74% |
| Kojic acid | Mg | 40 | 10.74% |
| Kuraridin | Mg | 0.5 | 0.13% |
| N-acetyl glucosamine (NAG) | Mg | 20 | 5.37% |
| Niacinamide | Mg | 100 | 26.84% |
| Oxyresveratrol (2,4,3',5'-tetrahydroxy-trans-stilbene) | Mg | 10 | 2.68% |
| Pyrroloquinoline Quinone | Mg | 20 | 5.37% |
| Quercetin | Mg | 10 | 2.68% |
| Vitamin K | Mg | 0.1 | 0.03% |
| Total Weight | G | 0.37 | 100.00% |

Suitable amounts of acetyl hexapeptide-3 and/or ceramide 2 and/or L-ascorbic acid/magnesium ascorbyl phosphate/sodium ascorbyl phosphate can be added with the topical composition (formulation) in Table 6.

About 0.5% by weight of ebselen, a broad spectrum antioxidant can be added with the topical composition (formulation) in Table 6.

Additionally, a nanoemulsion system/biodegradable substrate (e.g., silk)/silicone-based polymer substrate with a high degree of stability can be utilized for transdermal delivery (via a patch) of the topical composition (formulation) in Table 6.

TABLE 7

TOPICAL COMPOSITION (FORMULATION) (540B)

| Stem Cells | Unit | +/−50% | WT % |
| --- | --- | --- | --- |
| Stem Cells Of *Malus domestica* | Mg | 250 | 50% |
| Stem Cells Of *Solanum lycopersicum* Leaves | Mg | 250 | 50% |
| Total Weight | G | 0.5 | 100.00% |

TABLE 8

TOPICAL COMPOSITION (FORMULATION) (540B)

| Growth Factors | Unit | +/−50% | WT % |
| --- | --- | --- | --- |
| Elastin | Mg | 50 | 10% |
| GAG | Mg | 50 | 10% |
| Hepatocyte Growth Factor (HGF) | Mg | 50 | 10% |
| Interleukins (IL-6, IL-7, IL-8) | Mg | 50 | 10% |
| Keratinocyte Growth Factor (KGF) | Mg | 50 | 10% |
| Soluble Collagen | Mg | 150 | 30% |
| Transforming Growth Factor Beta (TGF-B) | Mg | 50 | 10% |
| Vascular Endothelial Growth Factor (VEGF) | Mg | 50 | 10% |
| Total Weight | G | 0.5 | 100.00% |

TABLE 9

NON-TOPICAL COMPOSITION (FORMULATION) (540B)

| CHEMICAL | Unit | +/−50% | WT % |
|---|---|---|---|
| Withaferin A (or a chemical derivative/structural analog of withaferin A) | Mg | 400 | 40.00% |
| Nicotinamide Riboside | Mg | 200 | 20.00% |
| Phosphatidylserine | Mg | 200 | 20.00% |
| Quercetin | Mg | 200 | 20.00% |
| Total Weight | G | 1.00 | 100.00% |

About 200 mg of Bisdemethoxycurcumin and/or about 200 mg of Curcumin and/or about 200 mg of Cycloastragenol and/or about 20 Mg of Dasatinib and/or about 200 mg of Metformine and/or about 200 mg of *Momordica charantia* and/or about 200 mg of Withanolides (or a chemical derivative/structural analog of Withanolides) and/or about 200 mg of Withanosides (or a chemical derivative/structural analog of Withanosides) and/or 0.06 mg of Vitamin D3 (Cholecalciferol) can be added to the non-topical composition (formulation) in Table 7. The non-topical composition (formulation) in Table 7 with or without addition of a bioactive compound(s) in the previous paragraph can be beneficial to protect against ageing by suppressing/inhibiting mTOR.

Fast Three-Dimensional Printer

The three-dimensional printing is an additive process, which means that a three-dimensional solid object can be formed by adding material in layers. This is in sharp contrast to current subtractive process, through which an object is formed by cutting/machining material into a desired shape. After a computer aided design (CAD) file is sent to a three-dimensional printer, one can choose a set of specific materials (e.g., composites, metals and plastics). In the three-dimensional printing, the materials are usually sprayed, squeezed or otherwise transferred from the three-dimensional printer onto a platform and then the three-dimensional printer makes passes (like an inkjet printer) over the platform, depositing a material layer on top of a material layer to print a product. The average thickness of a three-dimensionally printed layer is about 15 microns to 100 microns.

FIG. 41A illustrates a fast three-dimensional printer 2560A for realizing a printed device (e.g., the multifunctional hairbrush device 101A). A high power (100 watts to 1000 watts) master oscillator power amplifier (MOPA) based short pulse fiber laser 2380A comprises/includes (a) a 980 nm pump laser module 2320, (b) a master oscillator power amplifier module 2340 and (c) an actively doped fiber 2360. The high power laser beam is expanded by an optical laser beam expander 2400 and the laser beam is divided by a beam splitter 2420. The laser beam is preciously positioned by a scanning stage 2440 onto a material tray (utilizing a roller and a larger diameter input nozzle) 2460A. Fast three-dimensional printing is enabled by (a) larger diameter nozzle (about 0.20 inch in diameter instead of currently utilized 0.020 inch in diameter) and (b) higher power pulsed fiber laser. Larger diameter nozzle can enable to lay down more material and higher power pulsed fiber laser (or a higher power pulse laser, amplified in plasma) can print more material layer-thus, resulting in a fast three-dimensional printer. Backward propagated laser beam from the beam splitter 2420 can be imaged by a CCD camera 2480 for in-situ process inspection. The laser beam from the master oscillator power amplifier based short pulse fiber laser 2380A and the scanning stage 2440 are controlled by a controller 2500. Furthermore, the computer aided design file can be verified and authenticated (against any misuse of intellectual property rights) by a centralized database stored in a cloud based computer 2520.

Three-Dimensional Micro/Nanoprinter

FIG. 41B illustrates a two-photon based three-dimensional printer 2560B for printing a micro/nanostructure. In many aspects, a two-photon based three-dimensional micro/nanoprinter 2560B is similar to the three-dimensional printer 2560A. The two-photon based three-dimensional printer 2560B utilizes a super high resolution femtosecond laser 2380B, a microscope objective 2540A/nanofocusing device 2540B and a tray 2460B for (biocompatible) photosensitive material (e.g., a positive-tone/negative-tone photoresist/inorganic-organic hybrid polymer/ormocer). Molecules in the (biocompatible) photosensitive material can harden to form a micro/nanostructure (e.g., a micro/nanoscaffold), when photosensitive molecules absorb two photons from the super high resolution femtosecond laser 2380B. The average thickness of a three-dimensionally nanoprinted layer is about 100 nm.

FIGS. 42A-42B illustrate two embodiments of a nanofocusing device 2540B.

FIG. 42A illustrates a tapered waveguide to focus the laser light below the Abbey's diffraction limit. The waveguide comprises/includes an ultrathin (about 100 nanometers) layer of silicon dioxide sandwiched between two ultrathin (about 30 nanometers) layers of gold. The waveguide can be tapered adiabatically (over 150 nanometers) in three dimensions to a singular point.

FIG. 42B illustrates a pattern of nanoscaled holes in ultrathin (100 nanometers) metal layer (supported by a transparent substrate) to focus the laser light below the Abbey's diffraction limit. The pattern comprises/includes about 20,000 nanoscaled holes, each hole having about 150 nanometers in diameter.

Preferred Embodiments & Scope of the Invention

In the above disclosed specifications "/" has been used to indicate an "or" and real-time means near real-time in practice.

In the above disclosed specifications "waveguide" has been used to indicate an "optical waveguide"

As used in this patent application and in the claims, the singular forms "a", "an", and "the" include also the plural forms, unless the context clearly dictates otherwise.

The term "includes" means "comprises". The term "including" means "comprising".

The term "couples" or "coupled" does not exclude the presence of an intermediate element(s) between the coupled items.

Any example in the above disclosed specifications is by way of an example only and not by way of any limitation. Having described and illustrated the principles of the disclosed technology with reference to the illustrated embodiments, it will be recognized that the illustrated embodiments can be modified in any arrangement and detail with departing from such principles. The technologies from any example can be combined in any arrangement with the technologies described in any one or more of the other examples. Alternatives specifically addressed in this patent application are merely exemplary and do not constitute all possible examples. Claimed invention is disclosed as one of several possibilities or as useful separately or in various combinations. See *Novozymes A/S* v. *DuPont Nutrition Biosciences APS,* 723 F.3d 1336, 1347.

The best mode requirement "requires an inventor(s) to disclose the best mode contemplated by him/her, as of the time he/she executes the patent application, of carrying out the invention." " . . . [T]he existence of a best mode is a purely subjective matter depending upon what the inventor(s) actually believed at the time the (patent) application was filed." See *Bayer AG* v. *Schein Pharmaceuticals, Inc.* The best mode requirement still exists under the America Invents Act (AIA). At the time of the invention, the inventor(s) described preferred best mode embodiments of the present invention. The sole purpose of the best mode requirement is to restrain the inventor(s) from applying for a patent, while at the same time concealing from the public preferred embodiments of their inventions, which they have in fact conceived. The best mode inquiry focuses on the inventor(s)' state of mind at the time he/she filed the patent application, raising a subjective factual question. The specificity of disclosure required to comply with the best mode requirement must be determined by the knowledge of facts within the possession of the inventor(s) at the time of filing the patent application. See *Glaxo. Inc.* v. *Novopharm Ltd.,* 52 F.3d 1043, 1050 (Fed. Cir. 1995).

The above disclosed specifications are the preferred best mode embodiments of the present invention. However, they are not intended to be limited only to the preferred best mode embodiments of the present invention. Numerous variations and/or modifications are possible within the scope of the present invention. Accordingly, the disclosed preferred best mode embodiments are to be construed as illustrative only. Those who are skilled in the art can make various variations and/or modifications without departing from the scope and spirit of this invention. It should be apparent that features of one embodiment can be combined with one or more features of another embodiment to form a plurality of embodiments. The inventor(s) of the present invention is not required to describe each and every conceivable and possible future embodiment in the preferred best mode embodiments of the present invention. See *SRI Int'l* v. *Matsushita Elec. Corp. of America,* 775F.2d 1107, 1121, 227 U.S.P.Q. (BNA) 577, 585 (Fed. Cir. 1985) (enbanc).

The scope and spirit of this invention shall be defined by the claims and the equivalents of the claims only. The exclusive use of all variations and/or modifications within the scope of the claims is reserved. The general presumption is that claim terms should be interpreted using their plain and ordinary meaning. See *Oxford Immunotec Ltd.* v. *Qiagen, Inc. et al.,* Action No. 15-cv-13124-NMG. Unless a claim term is specifically defined in the preferred best mode embodiments, then a claim term has an ordinary meaning, as understood by a person with an ordinary skill in the art, at the time of the present invention. Plain claim language will not be narrowed, unless the inventor(s) of the present invention clearly and explicitly disclaims broader claim scope. See *Sumitomo Dainippon Pharma Co.* v. *Emcure Pharm. Ltd.,* Case Nos. 17-1798; -1799; -1800 (Fed. Cir. Apr. 16, 2018) (Stoll, J). As noted long ago: "Specifications teach. Claims claim". See *Rexnord Corp.* v. *Laitram Corp.,* 274 F.3d 1336, 1344 (Fed. Cir. 2001). The rights of claims (and rights of the equivalents of the claims) under the Doctrine of Equivalents-meeting the "Triple Identity Test" (a) performing substantially the same function, (b) in substantially the same way and (c) yielding substantially the same result. See *Crown Packaging Tech., Inc.* v. *Rexam Beverage Can Co.,* 559 F.3d 1308, 1312 (Fed. Cir. 2009)) of the present invention are not narrowed or limited by the selective imports of the specifications (of the preferred embodiments of the present invention) into the claims.

While "absolute precision is unattainable" in patented claims, the definiteness requirement "mandates clarity." See *Nautilus, Inc.* v. *Biosig Instruments, Inc.,* 527 U.S., 134 S. Ct. 2120, 2129, 110 USPQ2d 1688, 1693 (2014). Definiteness of claim language must be analyzed NOT in a vacuum, but in light of:

(a) The content of the particular patent application disclosure,
(b) The teachings of any prior art, and
(c) The claim interpretation that would be given by one possessing the ordinary level of skill in the pertinent art at the time the invention was made. (Id.).

See *Orthokinetics, Inc.* v. *Safety Travel Chairs, Inc.,* 806 F.2d 1565, 1 USPQ2d 1081 (Fed. Cir. 1986)

There are number of ways the written description requirement is satisfied. Applicant(s) does not need to describe every claim element exactly, because there is no such requirement (MPEP § 2163). Rather to satisfy the written description requirement, all that is required is "reasonable clarity" (MPEP § 2163.02). An adequate description may be made in anyway through express, implicit or even inherent disclosures in the patent application, including word, structures, figures, diagrams and/or equations (MPEP §§ 2163(1), 2163.02). The set of claims in this invention generally covers a set of sufficient number of embodiments to conform to written description and enablement doctrine. See *Ariad Pharm., Inc.* v. *Eli Lilly & Co.,* 598 F.3d 1336, 1355 (Fed. Cir. 2010), *Regents of the University of California* v. *Eli Lilly & Co.,* 119 F.3d 1559 (Fed. Cir. 1997) & *Amgen Inc.* v. *Chugai Pharmaceutical Co.* 927 F.2d 1200 (Fed. Cir. 1991).

Drawings under 37 C.F.R. § 1.83(a): In particular, as outlined in MPEP 608.02 Drawing [R-07.2015], the statutory requirement for showing the claimed invention only requires that the "applicant shall furnish a drawing where necessary for the understanding of the subject matter to be patented . . . " (See 35 U.S.C. § 113, See also 37 CFR § 1.81(a), which states "[t]he applicant for a patent is required to furnish a drawing of the invention where necessary for the understanding of the subject matter sought to be patented . . . ").

Furthermore, *Amgen Inc.* v. *Chugai Pharmaceutical Co.* exemplifies Federal Circuit's strict enablement requirements. Additionally, the set of claims in this invention is intended to inform the scope of this invention with "reasonable certainty". See *Interval Licensing, LLC* v. *AOL Inc.* (Fed. Cir. Sep. 10, 2014). A. key aspect of the enablement requirement is that it only requires that others will not have to perform "undue experimentation" to reproduce it. Enablement is not precluded by the necessity of some experimentation, "[t]he key word is 'undue', not experimentation." Enablement is generally considered to be the most important factor for determining the scope of claim protection allowed. However, enablement does not require that an inventor disclose every possible embodiment of his invention. The scope of enablement must be commensurate with the scope of the claims. The scope of the claims must be less than or equal to the scope of enablement. See *Promega* v. *Life Technologies* Fed. Cir., December 2014, *Magsil* v. *Hitachi Global Storage* Fed. Cir. August 2012.

The term "means" was not used nor intended nor implied in the disclosed preferred best mode embodiments of the present invention. Thus, the inventor(s) has not limited the scope of the claims as mean plus function.

An apparatus claim with functional language is not an impermissible "hybrid" claim; instead, it is simply an apparatus claim including functional limitations. Additionally, "apparatus claims are not necessarily indefinite for using functional language . . . [f]unctional language may also be employed to limit the claims without using the means-plus-function format." See *National Presto Industries, Inc.* v. *The West Bend Co.,* 76 F. 3d 1185 (Fed. Cir. 1996), *R.A.C.C. Indus.* v. *Stun-Tech, Inc.,* 178 F.3d 1309 (Fed. Cir. 1998) (unpublished), *Microprocessor Enhancement Corp.* v. *Texas Instruments Inc,* & *Williamson* v. *Citrix Online, LLC,* 792 F.3d 1339 (2015).

I claim:

1. An apparatus comprising:
 (a) a massaging device for skin;
 wherein the massaging device for skin comprises bristles,
 wherein the massaging device for skin, or the bristles are mechanically rotated in a clockwise motion, or in a counter clockwise motion, or in a circular motion,
 wherein the massaging device for skin, or the bristles are further mechanically vibrated within a range of frequencies between 40 Hz and 100 Hz,
 (b) a light source;
 wherein the light source activates, or photoactivates a bioactive compound, or a botanical compound, or a biologically active molecule, or a liquid for rejuvenation, or protection of skin,
 wherein the light source has
 (i) a first optical dose in the range from 0.5 J/cm$^2$ to 10 J/cm$^2$ in 600 nm-700 nm wavelength range,
 or,
 (ii) a second optical dose in the range from 0.5 J/cm$^2$ to 50 J/cm$^2$ in 700 nm-2000 nm wavelength range,
 (c) (i) an applicator, or (ii) a device for heating, and/or cooling of skin; and
 wherein the applicator comprises one or more first mechanical components,
 wherein the device for heating, and/or cooling of skin comprises one or more second mechanical components,
 (d) a temperature controller,
 wherein the temperature controller comprises one or more electronic components,
 wherein the apparatus is coupled with a mirror,
 wherein the apparatus is further coupled with an augmented reality (AR) application (app).

2. The apparatus according to claim 1, is further coupled with an artificial intelligence (AI) based instruction, or an artificial neural network (ANN) based instruction.

3. The apparatus according to claim 1, is further coupled with an artificial intelligence (AI) instruction based chatbot, or an artificial neural network (ANN) instruction based chatbot.

4. The apparatus according to claim 1, is further coupled with an input data comprising a selfie and questionnaires of a user.

5. The apparatus according to claim 1, further comprising a printed artificial skin, wherein the printed artificial skin comprises the bioactive compound, or the botanical compound, or the biologically active molecule for rejuvenation, or protection of skin.

6. The apparatus according to claim 5, wherein the biologically active molecule comprises a molecule released by a stem cell for protection of skin.

7. The apparatus according to claim 5, wherein the biologically active molecule comprises a molecule for protection of a stem cell of skin.

8. The apparatus according to claim 1, further comprising a patch, or a scaffold, wherein the patch, or the scaffold comprises the bioactive compound, or the botanical compound, or the biologically active molecule, or the liquid for rejuvenation, or protection of skin.

9. The apparatus according to claim 1, further comprising an electromagnetically coupled wireless charger, wherein the electromagnetically coupled wireless charger comprises a power harvesting circuit.

10. An apparatus comprising:
 (a) a massaging device for skin;
 wherein the massaging device for skin comprises bristles,
 wherein the bristles comprise a biocompatible material, or a biocomposite material, or nylon,
 wherein the massaging device for skin, or the bristles are mechanically rotated in a clockwise motion, or in a counter clockwise motion, or in a circular motion,
 wherein the massaging device for skin, or the bristles are further mechanically vibrated within a range of frequencies between 40 Hz and 100 Hz,
 (b) a light source;
 wherein the light source activates, or photoactivates a bioactive compound, or a botanical compound, or a biologically active molecule, or a liquid for rejuvenation, or protection of skin,
 wherein the light source has
 (i) a first optical dose in the range from 0.5 J/cm$^2$ to 10 J/cm$^2$ in 600 nm-700 nm wavelength range,
 or,
 (ii) a second optical dose in the range from 0.5 J/cm$^2$ to 50 J/cm$^2$ in 700 nm-2000 nm wavelength range,
 (c) (i) an applicator, or (ii) a device for heating, and/or cooling of skin; and
 wherein the applicator comprises one or more first mechanical components,
 wherein the device for heating, and/or cooling of skin comprises one or more second mechanical components,
 (d) a temperature controller,
 wherein the temperature controller comprises one or more electronic components,
 wherein the apparatus is coupled with a mirror,
 wherein the apparatus is further coupled with an augmented reality (AR) application (app).

11. The apparatus according to claim 10, is further coupled with an artificial intelligence (AI) based instruction, or an artificial neural network (ANN) based instruction.

12. The apparatus according to claim 10, is further coupled with an artificial intelligence (AI) instruction based chatbot, or an artificial neural network (ANN) instruction based chatbot.

13. The apparatus according to claim 10, is further coupled with an input data comprising a selfie and questionnaires of a user.

14. The apparatus according to claim 10, further comprising a printed artificial skin, wherein the printed artificial skin comprises the bioactive compound, or the botanical compound, or the biologically active molecule for rejuvenation, or protection of skin.

15. The apparatus according to claim 10, wherein the biologically active molecule comprises a molecule released by a stem cell for protection of skin.

16. The apparatus according to claim 10, wherein the biologically active molecule comprises a molecule for protection of a stem cell of skin.

17. The apparatus according to claim 10, further comprising a patch, or a scaffold, wherein the patch, or the scaffold comprises the bioactive compound, or the botanical compound, or the biologically active molecule, or the liquid for rejuvenation, or protection of skin.

18. The apparatus according to claim 10, further comprising an electromagnetically coupled wireless charger, wherein the electromagnetically coupled wireless charger comprises a power harvesting circuit.

19. An apparatus comprising:

(a) a massaging device for skin;

wherein the massaging device for skin comprises bristles, wherein the bristles comprise a biocompatible material, or a biocomposite material, or nylon, wherein the massaging device for skin, or the bristles are mechanically rotated in a clockwise motion, or in a counter clockwise motion, or in a circular motion, (b) a light source;

wherein the light source activates, or photoactivates a bioactive compound, or a botanical compound, or a biologically active molecule, or a liquid for rejuvenation, or protection of skin, wherein the light source has (i) a first optical dose in the range from 0.5 $J/cm^2$ to 10 $J/cm^2$ in 600 nm-700 nm wavelength range, or, (ii) a second optical dose in the range from 0.5 $J/cm^2$ to 50 $J/cm^2$ in 700 nm-2000 nm wavelength range, (c) (i) an applicator, or (ii) a device for heating, and/or cooling of skin; and wherein the applicator comprises one or more first mechanical components, wherein the device for heating, and/or cooling of skin comprises one or more second mechanical components, (d) a temperature controller;

wherein the temperature controller comprises one or more electronic components, wherein the apparatus is coupled with a mirror, wherein the apparatus is further coupled with an augmented reality (AR) application (app).

20. The apparatus according to claim 19, is further coupled with an artificial intelligence (AI) based instruction, or an artificial neural network (ANN) based instruction.

21. The apparatus according to claim 19, is further coupled with an artificial intelligence (AI) instruction based chatbot, or an artificial neural network (ANN) instruction based chatbot.

22. The apparatus according to claim 19, is further coupled with an input data comprising a selfie and questionnaires of a user.

23. The apparatus according to claim 19, further comprising a printed artificial skin, wherein the printed artificial skin comprises the bioactive compound, or the botanical compound, or the biologically active molecule for rejuvenation, or protection of skin.

24. The apparatus according to claim 23, wherein the biologically active molecule comprises a molecule released by a stem cell for protection of skin.

25. The apparatus according to claim 23, wherein the biologically active molecule comprises a molecule for protection of a stem cell of skin.

26. The apparatus according to claim 19, further comprising a patch, or a scaffold, wherein the patch, or the scaffold comprises the bioactive compound, or the botanical compound, or the biologically active molecule, or the liquid for rejuvenation, or protection of skin.

27. The apparatus according to claim 19, further comprising an electromagnetically coupled wireless charger, wherein the electromagnetically coupled wireless charger comprises a power harvesting circuit.

* * * * *